(12) United States Patent
Moyle et al.

(10) Patent No.: US 6,756,211 B1
(45) Date of Patent: Jun. 29, 2004

(54) NEUTROPOHIL INHIBITORS

(75) Inventors: Matthew Moyle, Escondido, CA (US); David L. Foster, San Diego, CA (US); George P. Vlasuk, Carlsbad, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 08/060,433

(22) Filed: May 11, 1993

Related U.S. Application Data

(63) Continuation-in-part of application No. 07/881,721, filed on May 11, 1992, now abandoned, and a continuation-in-part of application No. 07/996,972, filed on Dec. 24, 1992, now abandoned.

(51) Int. Cl.$^7$ .......................... C07H 21/04; C12N 15/00; C12N 15/85; C12P 21/00; C07K 14/00
(52) U.S. Cl. ..................... 435/69.1; 435/320; 435/325; 435/358; 536/23.1; 536/24.1; 530/300; 530/324; 530/326; 530/328; 530/350
(58) Field of Search ............................... 435/69.1, 320, 435/325, 358, 69.2; 536/23.1, 24.1; 530/300, 324, 326, 328, 350, 351, 395; 424/85.1, 522, 527; 514/2, 8

(56) References Cited

U.S. PATENT DOCUMENTS

| | | | | |
|---|---|---|---|---|
| 4,431,739 A | * | 2/1984 | Riggs .......................... | 435/69.1 |
| 4,438,032 A | * | 3/1984 | Golde et al. ................. | 260/112 |
| 5,019,648 A | | 5/1991 | Schlossman et al. ........ | 530/387 |
| 5,314,992 A | * | 5/1994 | Guyre et al. ................. | 530/350 |
| 5,484,711 A | * | 1/1996 | Wallner et al. .............. | 435/69.2 |

OTHER PUBLICATIONS

Wallner et al. Cloning and expression of human lipocortin, a phospholipase A2 inhibitor with potential anti–inflammatory activity. Nature. Mar. 6–12, 1986; 320(6057):77–81.*
Alberts et al., Molecular Biology of the Cell, Jan. 1994, Garland Publishing, Inc., New York, NY, pp. G–10, Jan. 1994.*
Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495.*
Meinkoth et al. Hybridization of nucleic acids immobilized on solid supports. Anal Biochem May 1, 1984;138(2):267–284.*
Sambrook et al., Molecular Cloning: A Laboratory Manual Second Edition vols. 1, 2 and 3. Cold Spring Harbor Laboratory Press: Cold Spring Harbor, New York, U.S.A. Nov., 1989, p. 10.13.*
Pritchard D I. The survival strategies of hookworms. Parasitology Today, vol. 11, No. 7, 1995.*
Sambrook J; Fritsch E F; Maniatis T. Molecular Cloning a Laboratory Manual Second Edition vols. 1 2 and 3. Cold Spring Harbor Laboratory Press: Cold Spring Harbor, New York, U.S.A. Nov. 1989.*
Wallace et al. Methods in Enzymology, vol. 152, Guide to Molecular Cloning Techniques, Berger et al, ed. Academic Press, New York, NY. 1987, Chapter 47, pp. 432–443.*
Alberts et al., Molecular Biology of the Cell, 1994, Garland Publishing, Inc., New York, NY, p. 119.*
Carlos et al., Immunological Reviews, vol. 114, issued 1990, pp. 5–28.
Savin et al., Molecular and Biochemical Parasitology, vol. 41, issued 1990, pp. 167–176.
Gasbarre et al., Infection and Immunity, vol. 48, No. 2, issued May 1985, pp. 540–545.
E.J.L. Soulsby, Immunol. Letters, vol. 16, issued 1987, pp. 315–320.
Monroy et al., Internat. Jour. Parsit., vol. 19, No. 1, issued 1989, pp. 125–127.
Madden, K., "A peptide derived from neutrophil inhibitory factor (NIF) blocks neutrophil adherence to endothelial cells", *Inflammation Research* 46 (1997) 216–223.

* cited by examiner

*Primary Examiner*—David S. Romeo
(74) *Attorney, Agent, or Firm*—Suzanne L. Biggs; Pillsbury Winthrop LLP

(57) ABSTRACT

Compositions enriched for Neutrophil Inhibitory Factor which inhibit neutrophil activity including adhesion to vascular endothelial cells are provided. Such compositions may comprise a glycoprotein isolated from nematodes. These compositions are useful in the therapy of conditions which involve abnormal or undesired inflammatory responses.

34 Claims, 13 Drawing Sheets

FIG. 7

TRYPSIN FRAGMENTS:

| | |
|---|---|
| T-24 | Ser Ala Phe Glu Leu Asp Ile Thr Asn Asn Gly Asn Gly Val Leu Met Arg |
| T-20 | Leu Ala Ile Leu Gly Trp Ala Arg |
| T-22-10 | Leu Phe Asp Arg Phe Pro Glu Lys |
| T-13 | Leu Glu Met Asp Cys Glu Ala Glu Lys |
| T-15-6 | Val Gly Thr Pro Cys Gly Asp Cys Ser Asn Tyr Thr Lys |

AspN FRAGMENTS:

| | |
|---|---|
| D-53 | Asp Glu Asn Ile Tyr Ile Phe Glu Asn Ser |
| D-54 | Asp Glu Asn Ile Tyr Ile Phe Glu Asn (Glu/his) |
| D-61 | Asp Ile (His/gln) Val Tyr Phe Ile Gly Gln (Arg/gly) (Ala/tyr) |
| D-67 | Asp Phe Ala Pro Arg Ala Ser Lys Met Arg Tyr Leu Glu Tyr |
| D-83 | Asp Tyr Ile Tyr Tyr Gln Leu Tyr Pro (Phe/Ala) Pro Met Ala His Lys Met Arg Tyr Leu |
| D-85 | Asp Xxx Met Gly Leu Gln Phe Leu Xxx Met His Asn Gly Xxx Arg |
| D-94 | Asp Ala Met Arg Leu Gln Phe Leu Ala (Met/gln/asn) Xxx Asn Gly Tyr Xxx Gly |
| D-96 | Asp Ile Ser Asn Phe Ala Asn Leu Ala Trp Asp |
| D-102 | Asp Glu Asn Lys Tyr Ile Phe Glu Asn Ser Asn Ile Ser Glu Ala Ala Leu Lys Ala Met Ile Ser Gly Ala Lys Gly Ala Phe Asn |

LysC FRAGMENTS:

| | |
|---|---|
| K-34A | Ala Met Ile Ser Trp Ala Lys |
| K-46B | Xxx Ala Tyr Ala Val Val Asn Leu Pro Leu Gly Glu Ile Ala Pro Glu Ala Ile |
| K-48 | Xxx Phe Tyr Xxx Phe Arg Glu (Leu/ile) |
| K-50A | Gly Ala Phe Asn Leu Asn Leu Thr Glu Gly Gly Glu Gly Val Leu Tyr Xxx Xxx Asn Xxx Asp Ile Ser Asn Phe Ala Asn Leu Ala Trp Asp |
| K-58A | Xxx Xxx Xxx Gly Val Leu Tyr Arg Xxx Xxx Leu Thr Ile Ser Asn Phe Ala Asn Leu Ala |

```
         10          20          30          40
         |           |           |           |
ATG GAG GCC TAT CTT GTG GTC TTA ATT GCC ATT GCT GGC ATA GCT
Met Glu Ala Tyr Leu Val Val Leu Ile Ala Ile Ala Gly Ile Ala 50          60          70          80          90
     |           |           |           |           |
CAT TCC AAT GAA CAC AAC CTG AGG TGC CCG CAG AAT GGA ACA GAA
His Ser Asn Glu His Asn Leu Arg Cys Pro Gln Asn Gly Thr Glu 100         110         120         130
         |           |           |           |
ATG CCC GGT TTC AAC GAC TCG ATT AGG CTT CAA TTT TTA GCA ATG
Met Pro Gly Phe Asn Asp Ser Ile Arg Leu Gln Phe Leu Ala Met 140         150         160         170         180
     |           |           |           |           |
CAC AAT GGT TAC AGA TCA AAA CTT GCG CTA GGT CAC ATC AGC ATA
His Asn Gly Tyr Arg Ser Lys Leu Ala Leu Gly His Ile Ser Ile 190         200         210         220
         |           |           |           |
ACT GAA GAA TCC GAA AGT GAC GAT GAT GAC GAT TTC GGT TTT TTA
Thr Glu Glu Ser Glu Ser Asp Asp Asp Asp Asp Phe Gly Phe Leu 230         240         250         260         270
     |           |           |           |           |
CCC GAT TTC GCT CCA AGG GCA TCG AAA ATG AGA TAT CTG GAA TAT
Pro Asp Phe Ala Pro Arg Ala Ser Lys Met Arg Tyr Leu Glu Tyr 280         290         300         310
         |           |           |           |
GAC TGT GAA GCT GAA AAA AGC GCC TAC ATG TCG GCT AGA AAT TGC
Asp Cys Glu Ala Glu Lys Ser Ala Tyr Met Ser Ala Arg Asn Cys
```

FIG. 8A

```
        320             330             340             350             360
         |               |               |               |               |
TCG GAC AGT TCT TCT CCA CCA GAG GGC TAC GAT GAA AAC AAG TAT
Ser Asp Ser Ser Ser Pro Pro Glu Gly Tyr Asp Glu Asn Lys Tyr 370             380             390             400
                 |               |               |               |
ATT TTC GAA AAC TCA AAC AAT ATC AGT GAA GCT GCT CTG AAG GCC
Ile Phe Glu Asn Ser Asn Asn Ile Ser Glu Ala Ala Leu Lys Ala 410             420             430             440             450
         |               |               |               |               |
ATG ATC TCG TGG GCA AAA GAG GCT TTC AAC CTA AAT AAA ACA AAA
Met Ile Ser Trp Ala Lys Glu Ala Phe Asn Leu Asn Lys Thr Lys 460             470             480             490
                 |               |               |               |
GAA GGA GAA GGA GTT CTG TAC CGG TCG AAC CAC GAC ATA TCA AAC
Glu Gly Glu Gly Val Leu Tyr Arg Ser Asn His Asp Ile Ser Asn 500             510             520             530             540
         |               |               |               |               |
TTC GCT AAT CTG GCT TGG GAC GCG CGT GAA AAG TTT GGT TGC GCA
Phe Ala Asn Leu Ala Trp Asp Ala Arg Glu Lys Phe Gly Cys Ala 550             560             570             580
                 |               |               |               |
GTT GTT AAC TGC CCT TTG GGA GAA ATC GAT GAT GAA ACC AAC CAT
Val Val Asn Cys Pro Leu Gly Glu Ile Asp Asp Glu Thr Asn His 590             600             610             620             630
         |               |               |               |               |
GAT GGA GAA ACC TAT GCA ACA ACC ATC CAT GTA GTC TGC CAC TAC
Asp Gly Glu Thr Tyr Ala Thr Thr Ile His Val Val Cys His Tyr
```

FIG. 8B

```
             640           650           660           670
              |             |             |             |
CCG AAA ATA AAC AAA ACT GAA GGA CAG CCG ATT TAC AAG GTA GGG
Pro Lys Ile Asn Lys Thr Glu Gly Gln Pro Ile Tyr Lys Val Gly 680           690           700           710           720
        |             |             |             |             |
ACA CCA TGC GAC GAT TGC AGT GAA TAC ACA AAA AAA GCA GAC AAT
Thr Pro Cys Asp Asp Cys Ser Glu Tyr Thr Lys Lys Ala Asp Asn 730           740           750           760
              |             |             |             |
ACC ACG TCT GCG GAT CCG GTG TGT ATT CCG GAT GAC GGA GTC TGC
Thr Thr Ser Ala Asp Pro Val Cys Ile Pro Asp Asp Gly Val Cys 770           780           790           800           810
        |             |             |             |             |
TTT ATT GGC TCG AAA GCC GAT TAC GAT AGC AAG GAG TTT TAT CGA
Phe Ile Gly Ser Lys Ala Asp Tyr Asp Ser Lys Glu Phe Tyr Arg

820
              |
TTC CGA GAG TTA TGA
Phe Arg Glu Leu ---
```

FIG. 8C

| | | | | | | | | | | | | | | |
|---|---|---|---|---|---|---|---|---|---|---|---|---|---|---|
| Met | Glu | Ala | Tyr | — | — | — | — | — | — | — | — | — | — | 1FL |
| Met | . | Leu | Leu | Leu | Arg | Lys | Phe | Leu | Leu | Leu | Trp | Leu | Ser Gly | 3P |
| Met | Lys | Ser | Tyr | — | — | — | — | — | — | — | — | — | — | 4FL |
| Met | Arg | Leu | Leu | Arg | Glu | Ala | Tyr | — | — | — | — | — | — | 6FL |

| | | | | | | | | | | | | |
|---|---|---|---|---|---|---|---|---|---|---|---|---|
| — | — | — | — | — | — | — | Leu | Val | Val | Leu | Ile Ala Ile Ala | 1FL |
| Thr | Phe | Lys | Arg | Gly | Arg | Arg | . | . | . | . | Ala . . . | 3P |
| | | | | | | | | | | . | Leu Leu Ser Ser | 2FL |
| | | | | | | | | . | . | . | . . . . | 3FL |
| — | — | — | — | — | — | — | . | Met | . | . | Ala . Val . | 4FL |
| — | — | — | — | — | — | — | . | . | . | . | Val . . . | 6FL |

| | | | | | | | | | | | | | |
|---|---|---|---|---|---|---|---|---|---|---|---|---|---|
| Gly | Ile | Ala | His | Ser | Asn | Glu | His | Asn | Leu | Arg | Cys | Pro Gln Asn | 1FL |
| . | . | . | . | Ala | . | . | . | Asp | Pro | Thr | . | . . . | 3P |
| Ser | Ala | . | . | . | . | . | . | . | Pro | Ile | . | Ser . . | 2FL |
| . | . | . | . | . | . | . | . | . | . | Thr | . | . . . | 3FL |
| . | . | . | . | Ala | . | . | . | Asp | . | Ile | . | . His . | 4FL |
| . | . | . | . | . | . | . | . | . | . | Thr | . | . . . | 6FL |

| | | | | | | | | | | | | |
|---|---|---|---|---|---|---|---|---|---|---|---|---|
| Gly | Thr | Glu | Met | Pro | — | Gly | Phe | Asn | Asp | Ser | Ile | Arg Leu Gln 1FL |
| . | Glu | Lys | . | Glu | Lys | . | . | Asp | . | Ala | . | . . Lys 3P |
| . | . | Gly | . | Phe | — | . | . | . | . | . | Met | . . Lys 2FL |
| . | . | . | . | . | — | . | . | . | . | . | . | . . . 3FL |
| Glu | Gly | . | . | Glu | Lys | . | . | Asp | . | Ala | Met | . . Lys 4FL |
| . | . | . | . | . | — | Asp | . | Ser | . | . | . | . . . 6FL |

| | | | | | | | | | | | | |
|---|---|---|---|---|---|---|---|---|---|---|---|---|
| Phe | Leu | Ala | Met | His | Asn | Gly | Tyr | Arg | Ser | Lys | Leu Ala Leu Gly | 1FL |
| . | . | . | . | . | . | . | . | . | . | Arg | . . . . | 3P |
| . | . | Glu | . | . | . | . | . | . | . | Arg | . . . . | 2FL |
| . | . | . | . | . | . | . | . | . | . | . | . . . . | 3FL |
| . | . | . | . | Leu | . | . | . | . | . | Arg | . . . . | 4FL |
| . | . | . | . | . | . | . | . | . | . | Asn | . . . . | 6FL |

FIG. 9A

```
His Ile Ser Ile Thr Glu Glu Ser Glu Ser  ---  Asp Asp Asp Asp 1FL
 .  Val  .   .   .   .   .   .   .  Asp Tyr  .  Leu ---  Tyr 3P
 .   .   .   .   .   .   .   .   .   .  ---   .   .   .  Tyr 1P
 .   .   .   .   .   .  Pro  .   .  Tyr  .    .   .   .   .  2FL
 .   .   .   .   .  Asp  .   .   .   .  --- Glu Ser  .   .  3FL
 .  Val  .   .   .   .   .   .   .  Asp Tyr  .  Leu ---  Tyr 4FL
 .   .  Gly  .  Ser Lys  .   .  Ile Gly Asp  .  Tyr  .   .  6FL

Asp Phe Gly Phe Leu Pro Asp --- Phe Ala Pro Arg Ala Ser Lys 1FL
 .  --- --- Leu  .  --- --- --- Tyr  .   .   .   .   .   .  3P
Glu Tyr  .   .   .   .   .  --- .   .   .   .   .   .   .  1P
 .  Tyr  .  Tyr Ser Glu Val Leu Tyr  .   .  Ser  .   .   .  2FL
Glu Tyr Asp Tyr Trp Tyr Ala Pro Thr  .   .  Thr  .   .   .  3FL
 .  --- --- Leu Ser --- --- --- Tyr  .   .  Thr  .   .   .  4FL
 .  Tyr Tyr Tyr Phe Tyr Ser Ser Tyr  .   .  Met  .   .   .  6FL

Met Arg Tyr Leu Glu Tyr Asp Cys Glu Ala Glu Lys Ser Ala Tyr 1FL
 .   .   .   .  Lys  .   .   .   .   .   .   .   .   .   .  3P
 .   .   .   .   .   .   .   .   .   .   .   .   .   .   .  1P
 .   .   .  Met  .   .   .   .   .   .   .   .   .   .   .  2FL
 .   .   .   .   .   .   .   .   .   .   .   .   .   .   .  3FL
 .   .   .   .  Lys  .   .   .   .   .   .   .   .   .   .  4FL
 .   .   .   .   .   .   .   .  Asp Ser  .  Arg  .   .   .  6FL

Met Ser Ala Arg Asn Cys Ser Asp Ser Ser Ser Pro Pro Glu Gly 1FL
Glu  .   .  Lys Lys  .  Gln Thr Thr Ala  .  Ser Trp  .  Lys 3P
Val  .   .  Ser  .   .  Asn Ile  .   .   .   .   .   .   .  1P
Lys  .   .  Ser Ser  .   .   .   .   .  Ser  .   .   .   .  2FL
 .   .   .   .   .   .   .   .   .   .   .   .   .   .   .  3FL
Glu  .   .  Lys Lys  .  Gln Thr Thr Ala  .  Ser Ser Thr Lys 4FL
 .   .   .  Ser  .   .   .   .   .   .   .   .   .   .   .  6FL
```

FIG. 9B

| | | | | | | | | | | | | | |
|---|---|---|---|---|---|---|---|---|---|---|---|---|---|
| Tyr | Asp | Glu | Asn | Lys | Tyr | Ile | Phe | Glu | Asn | Ser | Asn | Asn | Ile | Ser | 1FL |
| . | . | . | . | Leu | Gln | Val | Ile | . | Asp | Pro | Lys | Asp | . | Asn | 3P |
| . | . | . | . | . | . | . | . | . | . | . | . | . | . | . | 1P |
| . | . | . | . | . | . | . | Leu | . | . | . | Ser | . | . | . | 2FL |
| --- | . | . | . | . | . | . | . | . | . | . | . | . | . | . | 3FL |
| . | . | . | . | Leu | Gln | Val | Ile | . | Asp | Pro | Arg | Asp | . | Asn | 4FL |
| . | . | . | . | . | . | . | Leu | . | . | . | Ser | . | . | Asn | 6FL |

| | | | | | | | | | | | | |
|---|---|---|---|---|---|---|---|---|---|---|---|---|
| Glu | Ala | Ala | Leu | Lys | Ala | Met | Ile | Ser | Trp | Ala | Lys | Glu | Ala | Phe | 1FL |
| His | . | . | . | . | . | Ile | . | . | . | Thr | . | . | . | . | 3P |
| . | . | . | . | . | . | . | . | . | . | . | . | . | . | . | 1P |
| . | . | . | Arg | Leu | . | Ile | Leu | . | . | . | . | . | . | . | 2FL |
| . | . | . | . | . | . | . | . | . | . | . | . | . | . | . | 3FL |
| His | . | . | . | . | . | Thr | . | . | . | Thr | . | . | . | . | 4FL |
| . | . | . | Arg | Leu | . | Ile | . | . | . | Gly | . | . | . | . | 6FL |

| | | | | | | | | | | | | |
|---|---|---|---|---|---|---|---|---|---|---|---|---|
| Asn | Leu | Asn | Lys | Thr | Lys | Glu | Gly | Glu | Gly | Val | Leu | Tyr | Arg | Ser | 1FL |
| . | . | . | . | . | . | --- | --- | . | . | . | Val | . | . | . | 3P |
| . | . | . | . | . | . | --- | --- | . | . | . | . | . | . | . | 1P |
| Asp | . | . | . | . | --- | --- | . | . | . | . | . | . | . | . | 2FL |
| . | . | . | . | . | . | Glu | . | . | . | . | . | . | . | . | 3FL |
| . | . | . | . | . | . | . | . | . | . | . | . | . | . | . | 4FL |
| . | . | . | Glu | . | --- | --- | . | . | . | . | . | . | . | . | 6FL |

| | | | | | | | | | | | | |
|---|---|---|---|---|---|---|---|---|---|---|---|---|
| Asn | His | Asp | Ile | Ser | Asn | Phe | Ala | Asn | Leu | Ala | Trp | Asp | Ala | Arg | 1FL |
| Ile | Leu | . | . | . | . | . | . | . | . | . | . | . | Thr | . | 3P |
| . | Leu | Thr | . | . | . | . | . | . | . | . | . | . | Thr | . | 1P |
| . | Leu | Thr | . | . | . | . | . | . | . | . | . | . | Thr | . | 2FL |
| . | . | . | . | . | . | . | . | . | . | . | . | . | Thr | . | 3FL |
| . | Leu | Thr | . | . | . | . | . | . | . | . | . | . | Thr | . | 6FL |

FIG. 9C

```
Glu Lys Phe Gly Cys Ala Val Val Asn Cys Pro Leu Gly Glu Ile  1FL
 .   .  Val  .   .   .   .   .  Lys  .  --- --- --- --- ---  3P
 .   .   .   .   .   .   .   .   .   .   .   .   .  Lys Pro  1P
 .   .   .   .   .   .   .  Ala Lys  .   .   .  ---  .  ---  2FL
 .   .   .   .   .   .   .   .   .   .   .   .   .   .   .   3FL
 .   .   .   .   .   .   .   .  Lys  .   .   .   .   .   .   6FL

Asp Asp Glu Thr Asn His Asp Gly Glu Thr Tyr Ala Thr Thr Ile  1FL
--- --- --- --- --- --- --- --- --- Ser --- Pro Arg  .  Thr  3P
 .  Ala Ile Ile Thr Asp  .  Glu  .  Asn  .   .   .  Ala  .   1P
 .  --- ---  .  --- --- --- --- --- Ser ---  .   .   .   .   2FL
 .  Gly Thr  .  Ile  .   .   .   .   .   .   .   .   .   .   3FL

His Val Val Cys His Tyr Pro Lys Ile Asn Lys Thr Glu Gly ---  1FL
 .   .   .   .   .   .   .   .  --- ---  .  Ser --- Arg Arg  3P
 .   .   .   .   .   .   .   .   .   .   .   .   .   .  ---  1P
 .   .   .   .   .   .   .   .   .  Glu Gly Glu  .  Lys Glu  2FL
 .   .   .   .   .   .   .   .  Met  .   .   .   .   .  ---  3FL

--- --- Gln Pro Ile Tyr Lys Val Gly Thr Pro Cys Asp Asp Cys  1FL
Lys Glu Asn  .   .   .  Thr Thr  .  Asn Arg  .  Gly Gly  .   3P
--- ---  .   .   .   .   .   .   .   .   .   .   .   .   .   1P
Gly Lys Gln ---  .   .   .   .   .   .   .   .  Gly  .   .   2FL
--- ---  .   .   .   .   .   .   .  Lys  .   .   .   .   .   3FL

Ser Glu Tyr Thr Lys Lys Ala Asp Asn Thr Thr Ser Ala Asp Pro  1FL
 .  Asp  .   .   .   .   .   .   .   .   .   .   .   .   .   3P
 .   .   .   .   .   .   .   .   .   .   .   .   .   .   .   1P
 .   .   .   .   .   .   .   .   .   .   .  Thr  .   .   .   2FL

Val Cys Ile Pro Asp Asp Gly Val Cys Phe Ile Gly Ser Lys Ala  1FL
Gln  .  His  .   .  Ile  .   .   .   .   .   .   .   .  Gly  1P

Asp Tyr Asp Ser Lys Glu Phe Tyr Arg Phe Arg Glu Leu  *        1FL
 .   .   .   .   .   .   .   .   .   .   .   .   .   *        1P
```

FIG. 9D

NEUTROPOHIL INHIBITORS

CROSS REFERENCE TO RELATED APPLICATIONS

This application is a continuation-in-part of U.S. Ser. No. 07/881,721 filed May 11, 1992 now abandoned and U.S. Ser. No. 07/996,972 now abandoned filed Dec. 24, 1992, the disclosures of which are incorporated herein by reference.

FIELD OF THE INVENTION

This invention relates to factors which inhibit neutrophil activity, including inhibition of neutrophil activation and adhesion of neutrophils to vascular endothelial cells.

BACKGROUND AND INTRODUCTION TO THE INVENTION

Neutrophils are a class of white blood cells (leukocytes) that comprise an essential component of the host defense system against microbial invasion. In response to soluble inflammatory mediators released by cells at the site of injury, neutrophils migrate into tissue from the bloodstream by crossing the blood vessel wall. At the site of injury, activated neutrophils kill foreign cells by phagocytosis and by the release of cytotoxic compounds, such as oxidants, proteases and cytokines. Despite their importance in fighting infection, neutrophils themselves can promote tissue damage. During an abnormal inflammatory response, neutrophils can cause significant tissue damage by releasing toxic substances at the vascular wall or in uninjured tissue. Alternatively, neutrophils that stick to the capillary wall or clump in venules may produce tissue damage by ischemia. Such abnormal inflammatory responses have been implicated in the pathogenesis of a variety of clinical disorders including adult respiratory distress syndrome (ARDS); ischemia-reperfusion injury following myocardial infarction, shock, stroke, and organ transplantation; acute and chronic allograft rejection; vasculitis; sepsis; rheumatoid arthritis; and inflammatory skin diseases (Harlan et al., 1990 Immunol. Rev. 114, 5).

Neutrophil adhesion at the site of inflammation involves at least two discrete cell-cell interactive events. Initially, vascular endothelium adjacent to inflamed tissue becomes sticky for neutrophils; neutrophils interact with the endothelium via low affinity adhesive mechanisms in a process known as "rolling". In the second adhesive step, rolling neutrophils bind more tightly to vascular endothelial cells and migrate from the blood vessel into the tissue. Neutrophil rolling along affected vascular segments and other initial low affinity contacts between neutrophils and the endothelium are mediated by a group of monomeric, integral membrane glycoproteins termed selectins. All three of the s-electins so far identified, that is L-selectin (LECAM-1, LAM-1) present on the surface of neutrophils, E-selectin (endothelial leukocyte adhesion molecule-1; ELAM-1) present on endothelial cells and P-selectin (granule membrane protein-140, GMP-140; platelet activation-dependent granule-external membrane protein, PADGEM; CD62) expressed on endothelial cells, have been implicated in neutrophil adhesion to the vascular endothelium (Jutila et al., 1989 J. Immunol 143, 3318; Watson et al., 1991 Nature 349, 164; Mulligan et al., J. Clin. Invest. 88, 1396; Gundel et al., 1991 J. Clin. Invest. 88, 1407; Geng et al., 1990 Nature 343, 757; Patel et al., 1991 J. Cell Biol. 112, 749). The counter-receptor for E-selectin is reported to be the sialylated Lewis X antigen (sialyl-Lewis$^x$) that is present on cell-surface glycoproteins (Phillips et al., 1990 Science 250, 1130; Walz et al., 1990 Science 250, 1132; Tiemeyer et al., 1991 Proc. Natl. Acad. Sci. (USA) 88, 1138; Lowe et al., 1990 Cell 63, 475). Receptors for the other selectins are also thought to be carbohydrate in nature but remain to be elucidated.

The more stable secondary contacts between neutrophils and endothelial cells are mediated by a class of cell adhesion molecules known as integrins. Integrins comprise a broad range of evolutionarily conserved heterodimeric transmembrane glycoprotein complexes that are present on virtually all cell types. Members of the leukocyte-specific CD18 ($\beta_2$) family of integrins, which include CD11a/CD18 (LFA-1) and CD11b/CD18 (Mac-1; Mo-1; CR3) have been reported to mediate neutrophil adhesion to the endothelium (reviewed in Larson and Springer, 1990 Immunol Rev. 114, 181). Endothelial cell counter-receptors for these integrins are the intercellular cell adhesion molecules ICAM-1 and ICAM-2 for CD11a/CD18 and ICAM-1 for CD11b/CD18, respectively (Rothlein et al., 1986 J. Immunol. 137, 1270; Staunton et al., 1988 Cell 52, 925; Staunton et al., 1989 Nature 339, 61). The ICAMs are monomeric transmembrane proteins that are members of the immunoglobulin superfamily.

The activation of endothelial cells and neutrophils represents an important component of neutrophil-mediated inflammation. Factors that induce cell activation are termed agonists. Endothelial cell agonists, which include small regulatory proteins such as tumor necrosis factor (TNFα) and interleukin-1 (IL-1α), are released by cells at the site of injury. Activation of endothelial cells results in the increased surface expression of ICAM-1 (Staunton et al., 1988 Cell 52, 925) and ELAM-1 (Bevilacqua et al., 1987 Proc. Natl. Acad. Sci. (USA) 84, 9238). Raised levels of expression of these adhesive molecules on the surface of activated endothelial cells leads to the observed increased adhesivity of neutrophils for the vascular endothelium near sites of injury.

Activation of the neutrophil results in profound changes to its physiological state, including shape change, ability to phagocytose foreign bodies and release of cytotoxic substances from intracellular granules. Moreover, activation greatly increases the affinity of adhesive contacts between neutrophils and the vascular endothelium, perhaps through a conformational change in the CD11b/CD18 integrin complex on the neutrophil surface (Vedder and Harlan, 1988 J. Clin. Invest. 81, 676; Buyon et al., 1988 J. Immunol. 140, 3156). Factors that have been reported to induce neutrophil activation include IL-1α, GM-CSF, G-CSF, MIP-1, IL-8 (IL-8=interleukin-8, GM-CSF=granulocyte/monocyte-colony stimulating factor, G-CSF=granulocyte-colony stimulating factor), and TNFα, the complement fragment C5a, the microbe-derived peptide formyl-Met-Leu-Phe and the lipid-like molecules leukotriene B4 (LTB$_4$) and platelet activating factor (Fuortes and Nathan, 1992, in *Molecular Basis of Oxidative Damage by Leukocytes* Eds Jesaitis, A. J. and Dratz, E. A. (CRC Press) pp. 81–90). In addition, phorbol esters (e.g., phorbol 12-myristate 13-acetate; PMA) represent a potent class of synthetic lipid-like neutrophil agonists. With the exception of PMA, these agonists have been reported to activate neutrophils by binding receptors on their surface. Receptors that are occupied by agonist molecules initiate within the neutrophil a cascade of events that ultimately results in the physiological changes that accompany neutrophil activation. This process is known as signal transduction. The lipid-like PMA likely effects neutrophil activation by passing through the plasma membrane at the cell surface and directly interacting with intracellular components (i.e., protein kinase) of the signal transduction machinery.

There exist two general classes of compounds that have been reported to down regulate the function of neutrophils, and these compounds have been reported to mitigate inflammation. One group of anti-inflammatory compounds is said to function as inhibitors of neutrophil activation, and presumably adhesion, by acting on components of the signal transduction machinery. A second class of anti-inflammatory compounds is said to block neutrophil infiltration into inflammatory foci by acting as direct inhibitors of the adhesive receptors that mediate contact between neutrophils and the vascular endothelium.

Many of the anti-inflammatory compounds currently used as therapeutics, including prostaglandins, catecholamines, and a group of agents known as non-steroidal anti-inflammatory drugs (NSAIDs), are believed to fall into the first category (Showell and Williams, 1989, in *Immunopharmacology*, eds. Gilman, S. C. and Rogers, T. J. [Telford Press, NJ] pp 23–63). For example, the enhanced adhesiveness observed for TNFa-activated neutrophils has been associated with decreased levels of a mediator of signal transduction, cyclic AMP (cAMP; Nathan and Sanchez, 1990 JCB 111, 2171). Exposure of neutrophils to prostaglandins and catecholamines has been correlated with elevated levels of intracellular cyclic AMP (cAMP; Showell and Williams, 1989). While the signal transduction inhibitors have been used extensively as anti-inflammatory therapeutic agents, they have several disadvantages including poor efficacy in acute inflammatory conditions, lack of specificity and undesirable side-effects such as gastric or intestinal ulceration, disturbances in platelet and central nervous system function and changes in renal function (Insel, 1990 in *The Pharmacological Basis of Therapeutics*, eds. Gilman, A. G., Rall, T. W., Nies, A. S., and Taylor, P. [Pergamon, N.Y.], 8th Ed., pp. 638–681).

Glucocorticoids have long been recognized for their anti-inflammatory properties. Steroid-induced inhibition of neutrophils has been reported for several neutrophil functions, including adherence (Clark et al., 1979 Blood 53, 633–641; MacGregor, 1977 Ann. Intern. Med. 86, 35–39). The mechanisms by which glucocorticoids modulate neutrophil function are not well understood, but they are generally believed to involve the amplification or suppression of new proteins in treated neutrophils that play a key role in the inflammatory process (Knudsen et al., 1987 J. Immunol. 139, 4129). In particular, a group of proteins known as lipocortins, whose expression is induced in neutrophils by glucocorticoids, has been associated with anti-inflammatory properties (Flower, 1989 Br. J. Pharmacol. 94, 987–1015). Lipocortins may exert anti-neutrophil effects by interacting with sites on the neutrophil surface (Camussi et al., 1990 J. Exp. Med. 171, 913–927), but there is no evidence to suggest that the lipocortins act by directly blocking adhesive proteins on the neutrophil. Apart from their beneficial anti-inflammatory properties, glucocorticoids have been associated with significant side-effects. These include suppression of pituitary-adrenal function, fluid and electrolyte disturbances, hypertension, hyperglycemia, glycosuria, susceptibility to infection, ulcers, osteoporosis, myopathy, arrest of growth and behavioral disturbances (Insel, 1990).

A second class of anti-inflammatory compounds which are reported as direct inhibitors of neutrophil adhesion to the vascular endothelium have been described recently. Monoclonal antibodies that recognize and block ligand-binding functions of some of these adhesive molecules have proved to be effective in vivo inhibitors of neutrophil-mediated inflammation. In particular, monoclonal antibodies to the CD18 subunit of the CD18 integrin complexes (i.e., CD11a/CD18, CD11b/CD18 and CD11c/CD18) on the surface of neutrophils have been shown to prevent a variety of neutrophil-mediated tissue injury in animal models, including pulmonary edema induced by reperfusion (Horgan et al, 1990 Am. J. Physiol. 259, L315–L319), organ injury induced by hemorrhagic shock (Mileski et al, 1990 Surgery 108, 206–212), myocardial damage following ischemia/reperfusion (Winquist et al, 1990 Circulation III-701), edema and tissue damage following ischemia/reperfusion of the ear (Vedder et al, 1990 Proc. Natl. Acad. Sci. (USA) 87, 2643–2646), brain edema and death produced by bacterial meningitis (Tuomanen et al, 1989 J. Exp. Med. 170, 959–968), vascular injury and death in endotoxic shock (Thomas et al, 1991 FASEB J. 5, A509) and indomethacin-induced gastric injury (Wallace et al, 1991 Gastroenterology 100, 878–883).

Monoclonal antibodies directed to the CD11b subunit have been described. See, e.g:, Todd, R. F. et al., U.S. Pat. No. 4,840,793 (Jun. 20, 1989), Todd, R. F. et al., U.S. Pat. No. 4,935,234 (Jun. 19, 1990), Schlossman, S. F. et al., U.S. Pat. No. 5,019,648 (May 28, 1991) and Rusche, J. R. et al., International Application No. WO 92/11870 (Jul. 23, 1992). Monoclonal antibodies directed to CD18 subunit have been described. See, e.g., Arfors, K. E., U.S. Pat. No. 4,797,277 (Jan. 10, 1989), Wright, S. D. et al., European Patent Application No. 346,078 (Dec. 13, 1989), Law, M. et al., European Patent Application No. 438,312 (Jul. 24, 1991), Law, M. et al., European Patent Application No. 440,351 (Aug. 7, 1991), Wright, S. D. et al., U.S. Pat. No. 5,147,637 (Sep. 15, 1992) and Wegner, C. D. et al., European Patent Application No. 507,187 (Oct. 7, 1992).

Antibodies to other adhesive molecules have also been reported to have anti-inflammatory properties. Monoclonal antibodies that recognize the counter-receptor of CD11a/CD18 and CD11b/CD18, ICAM-1 have been reported to prolong cardiac allograft survival (Flavin et al, 1991 Transplant. Proc. 23, 533–534) and prevent chemically induced lung inflammation (Barton et al, 1989 J. Immunol. 143, 1278–1282). Furthermore, anti-selectin monoclonal antibodies have also been reported as efficacious in animal models of neutrophil-mediated inflammation. Monoclonal antibodies to L-selectin are reported to prevent neutrophil emigration into inflamed skin (Lewinshon et al., 1987 J. Immunol. 138, 4313) and inflamed ascites (Jutila et al., 1989 J. Immunol. 143, 3318; Watson et al., 1991 Nature 349, 164). Reports have also described inhibition of neutrophil influx into inflamed lung tissue by anti E-selectin monoclonal antibodies (Mulligan et al., 1991 J. Clin. Invest. 88, 1396; Gundel et al., 1991 J. Clin. Invest. 88, 1407). While the reports concerning activities of monoclonal antibodies to adhesive proteins are said to demonstrate the feasibility of using neutrophil adhesion inhibitors as anti-inflammatory agents, the utility of such monoclonal antibodies as therapeutics needs further evaluation.

Soluble adhesive receptors obtained by genetic engineering have been advanced as a further alternative approach as anti-inflammatory compounds. Soluble receptors, in which the transmembrane and intracellular domains have been deleted by recombinant DNA technology, have been reported to inhibit neutrophil adhesion to endothelial cells. The functional use of recombinant soluble adhesive molecules has been reported using CD11b/CD18 (Dana et al., 1991 Proc. Natl. Acad. Sci.(USA) 88, 3106–3110) and L-selectin (Watson et al., 1991, Nature 349:164–167).

Recently, a new class of anti-leukocyte compounds collectively termed leumedins has been reported. These compounds have been reported to block the recruitment in vivo of T lymphocytes and neutrophils into inflammatory lesions. The mechanism of action of the leumedins is unclear, but there is evidence that they do not function by blocking neutrophil activation (Burch et al., 1991 Proc. Natl. Acad. Sci. (USA) 88, 355). It remains to be determined if leumedins block neutrophil infiltration by direct interference with adhesive molecules.

It has been suggested that parasites survive in their host by modulating host immunity and inflammatory response though the mechanisms by which this occurs remains unclear (Leid, W. S., 1987, Veterinary Parasitology, 25: 147). In this regard, parasite-induced immunosuppression has been reported using certain rodent models (Soulsby et al., 1987, Immunol Lett. 16, 315–320).

Certain effects on neutrophils caused by materials isolated from parasites have been reported. For example, a protein isolated from the cestode, *Taenia taeniaeformis,* has been reported to inhibit chemotaxis and chemokinesis of equine neutrophils, as well as inhibit neutrophil aggregation (c. Suquet et al., 1984, Int'l J. Parasitol., 14: 165; Leid, R. W. et al., 1987, Parasite Immunology, 9: 195; and Leid, R. W. et al., 1987, Int'l J. Parasitol., 17: 1349). Peritoneal neutrophils from mice infected with the cestode, *Echinococcus multiocularis,* have been reported to lose their ability to migrate toward parasite antigens and nonspecific chemoattractants with increasing time of infection (Alkarmi, T. et al., Exptl. Parasitol., 1989, 69: 16). The nematode, *Trichinella spiralis,* has been reported to either excrete and/or secrete factors which inhibit chemotaxis and p-nitroblue tetrazolium reduction (i.e., release of oxidative metabolites) but enhance chemokinesis of human neutrophils (Bruschi, F. et al., 1989, Wiadomosci Parazytologiczne, 35: 391). The sera of humans infected with the nematode, *Trichinella spiralis,* has been reported to inhibit leukocyte chemotaxis and phagocytosis (Bruschi, F. et al., 1990, J. Parasitol., 76: 577). The saliva of the tick, *Ixodes dammini,* has been reported to inhibit neutrophil function (Ribeiro et al, 1990, Exp. Parasitol., 70, 382). A protein secreted by the cestode, *Echinococcus granulosus,* has been reported to inhibit human neutrophil chemotaxis (Shepard, J. C. et al., 1991, Mol. Biochem. Parasitol., 44: 81).

SUMMARY OF THE INVENTION

The present invention is directed to a neutrophil inhibitory factor ("Neutrophil Inhibitory Factor" or "NIF") and to enriched compositions comprising Neutrophil Inhibitory Factor. Neutrophil Inhibitory Factor is a protein which is neither an antibody, a member of the integrin or selectin families nor a member of the immunoglobulin superfamily of adhesive proteins and which when isolated from a parasitic worm is a glycoprotein. Recombinant NIF's produced by certain expression systems are not glycosylated. However, such non-glycosylated NIFs are considered to be within the scope of the present invention. A Neutrophil Inhibitory Factor of the present invention exhibits neutrophil inhibitory activity. Such neutrophil inhibitory activity may be demonstrated by its inhibition of at least one biological response in mammalian cells induced by activated neutrophils in an in vitro assay. Suitable assays for determining neutrophil inhibitory activity include those where inhibition of neutrophil activity is demonstrated by an assay which determines adhesion of neutrophils to vascular endothelial cells, release of hydrogen peroxide from neutrophils, homotypic neutrophil aggregation or adhesion of neutrophils to plastic surfaces. In a preferred aspect the Neutrophil Inhibitory Factor comprises a protein present in and isolated from or substantially similar to a compound present in a parasitic worm, preferably canine hookworms, that inhibits neutrophil activity, particularly neutrophil adhesion to vascular endothelial cells. It is believed that certain isoforms of NIF are produced by the canine hookworm *Ancylostoma caninum.* This protein appears to act, at least in part, by inhibiting the process of neutrophil activation. A NIF has been demonstrated to be present in another parasitic worm, *Toxocara canis.*

In view of the myriad conditions associated with undesired and/or abnormal inflammatory conditions which appear to be associated with neutrophil activity, there remains a need for potent, highly specific inhibitors of neutrophil function, in particular, adhesion to vascular endothelium, as a treatment for abnormal neutrophil-mediated inflammation. The present invention describes a potent and specific inhibitor of neutrophil activity, in particular the adhesion of neutrophils to vascular endothelial cells, derived from the hookworm (*Ancylostoma caninum*) and related species.

Among other factors, the present invention is based on our finding that the Neutrophil Inhibitory Factor of the present invention represents a pioneering step toward the development of a new generation of anti-inflammatory therapeutic products. This discovery will enable the first therapy for inflammatory disease based entirely on specific inhibition of the inflammatory response. The therapeutic advantages of this novel approach are realized through the specificity of Neutrophil Inhibitory Factor compared to current clinical treatment modalities such as steroids, catecholamines, prostaglandins, and nonsteroidal anti-inflammatory agents. The currently used class of therapeutic agents demonstrates poor efficacy and multiple adverse reactions due to generalized systemic effects that non-specifically target numerous biological processes in addition to the inflammatory process. Nonetheless, the existence of this extensive panel of anti-inflammatory agents, although suboptimal, and the total funds expended by the pharmaceutical industry in research in this area point to significant medical needs and suggests that the discovery of this novel and highly specific Neutrophil Inhibitory Factor will have important applications.

The inflammatory response results in clinical syndromes ranging from debilitating arthritis and asthma to life threatening shock. In view of the severity of these disorders, the vast number of afflicted individuals and the lack of suitable therapeutic intervention, the need for a breakthrough therapy represents a long felt need which has not been met. The Neutrophil Inhibitory Factor of the present invention represents such a breakthrough and provides the potential for a lifesaving therapy which is currently being sought throughout the international medical and pharmaceutical research communities.

The Neutrophil Inhibitory Factor can be isolated by preparing a soluble extract of the worm and fractionating it by chromatography on immobilized Concanavalin A, a molecular sieving matrix, and ceramic hydroxylapatite, and optionally, C4 reverse phase silica. Thus, according to another aspect, the present invention is directed to methods of isolating enriched compositions comprising Neutrophil Inhibitory Factor and the enriched compositions isolated by those methods. The factor can also be partially purified by preparative isoelectric focusing and chromatography on anion exchange media.

In one aspect, the present invention is directed to a composition enriched for Neutrophil Inhibitory Factor comprising a glycoprotein wherein the factor is isolated from a parasitic worm.

In another aspect, the present invention provides a composition enriched for Neutrophil Inhibitory Factor. In one preferred embodiment, the composition is isolated from a parasitic worm. Preferably the composition is enriched at least 200-fold for neutrophil inhibitory activity. Preferably the enriched composition is at least about 90% pure, more preferably, it is chromatographically pure.

According to one embodiment, the glycoprotein or Neutrophil Inhibitory Factor of the present invention is preferably acidic as determined by isoelectric focusing, having an isoelectric point of about 4.5, and preferably has a molecular weight in the range of about 38,000 to about 44,000 daltons as determined by laser-desorption time-of-flight mass-spectroscopy.

Preferably, the parasitic worm is a species selected from the phyla Platyhelminthes, Nematoda, Nematomorpha and Acanthocephala, more preferably Nematoda, and especially is isolated from a hookworm species such as those of the super family Ancylostomatidae.

The neutrophil inhibitory activity of the Neutrophil Inhibitory Factor of the present invention may be conveniently demonstrated by its inhibition of at least one biological response in mammalian cells induced by activated neutrophils in an in vitro assay. Suitable assays include those which determine adhesion of neutrophils to vascular endothelial cells or to plastic surfaces, release of hydrogen peroxide by neutrophils or homotypic neutrophil aggregation. Suitable Neutrophil Inhibitory Factors exhibit an $IC_{50}$ of about 500 nM or less, more preferably less than 100 nM.

According to a further aspect of the present invention, methods of preparing biologically active Neutrophil Inhibitory Factor are provided. These methods comprise culturing host cells containing an expression vector which encodes a gene for a glycoprotein having neutrophil inhibitory activity isolated from a hookworm, preferably a canine hookworm, which has apparent molecular weight of about 38,000 to about 44,000 daltons as determined by laser-desorption time-of-flight mass spectrometry, and to the recombinant Neutrophil Inhibitory Factor produced according to those methods.

Also encompassed within the scope of the invention are isolated nucleic acid molecules, preferably DNA, which code for Neutrophil Inhibitory Factor, vectors, (including cloning and expression vectors) which contain the nucleic acid molecule and host cells transformed with such vectors.

The present invention also provides methods of preparing recombinant Neutrophil Inhibitory Factor using a nucleic acid molecule encoding the Neutrophil Inhibitory Factor. The nucleic acid molecule is expressed in a cultured host cell transformed with a vector containing the nucleic acid molecule operably linked to control sequences recognized by the host cell.

In a further aspect, the present invention is directed to antibodies against Neutrophil Inhibitory Factor, including monoclonal antibodies and hybridomas which produce the monoclonal antibodies, and to immunoassays using the antibodies.

The invention is also directed to pharmaceutical compositions comprising a therapeutically effective amount of Neutrophil Inhibitory Factor and a pharmaceutically acceptable carrier, and the methods of using these pharmaceutical compositions to treat inflammatory conditions, especially to prevent or decrease inflammatory responses. In particular, such pharmaceutical compositions may comprise Neutrophil Inhibitory Factor and a pharmaceutically acceptable carrier, wherein the Neutrophil Inhibitory Factor interacts with neutrophils to inhibit their activity and prevents and/or decreases inflammatory responses in a mammalian host caused by neutrophils when a therapeutically effective amount of Neutrophil Inhibitory Factor is administered.

According to a further aspect, the present invention is directed to methods of isolating NIF-like proteins and to NIF-like proteins so isolated. These NIF-like proteins may be isolated by preparing a genomic or cDNA library from a source, whether animal, bacterial, fungal or viral, which is suspected of containing Neutrophil Inhibitory Factor, hybridizing oligonucleotide probes sufficiently complementary to hybridize to a nucleic acid encoding a NIF to the library and isolating nucleic acid sequences which hybridize to the probes. The nucleic acid sequence can then be cloned and expressed. Alternatively NIF-like proteins may be isolated which include a protein which is encoded by a nucleic acid sequence which is sufficiently complementary to hybridize to a probe having at least about 12 nucleotides which is complementary to a portion of nucleic acid sequence encoding a NIF, in one preferred aspect the sequence of FIG. 8.

Other features and advantages of the invention will be apparent from the following descriptions of the preferred embodiments and from the claims.

BRIEF DESCRIPTION OF THE DRAWINGS

FIG. 7 depicts the amino acid sequence of proteolytic fragments prepared from Neutrophil Inhibitory Factor isolated from canine hookworm [SEQ. ID. NOS. 13 to 31].

FIG. 8 depicts the nucleotide sequence of the coding region of Neutrophil Inhibitory Factor cDNA (clone 1FL) [SEQ. ID. NO:32] and its predicted amino acid sequences [SEQ. ID. NO. 33].

FIG. 9 depicts the alignment of the predicted amino acid sequences of several Neutrophil Inhibitory Factor isoform clones [SEQ. ID. NOS. 33 to 39].

DETAILED DESCRIPTION OF THE INVENTION

Neutrophil Inhibitory Factor

Figure 1:
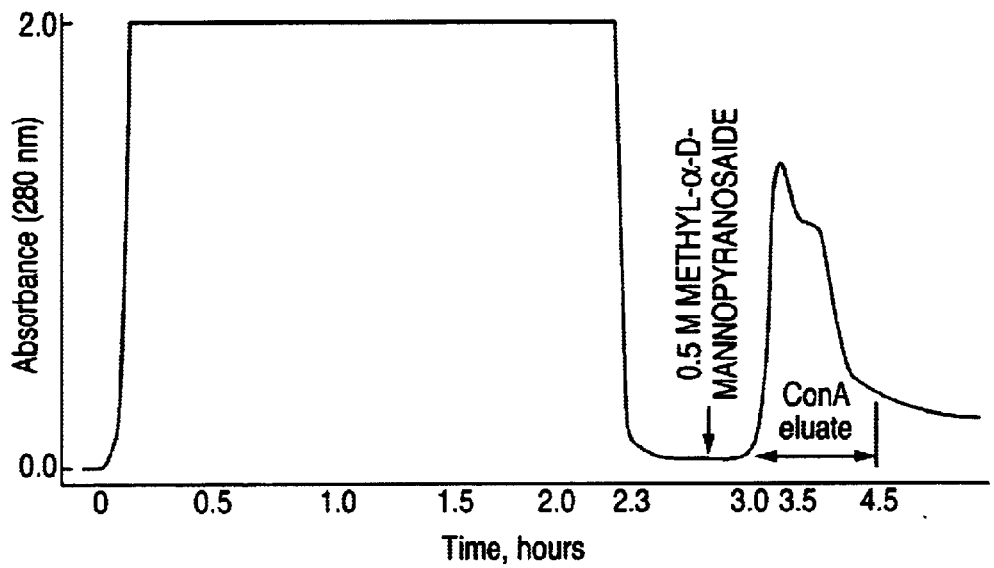
FIG. 1 depicts a chromatogram of hookworm lysate obtained as described in the Example 2(A) run on the Example 2(B) Concanavalin A Sepharose column.

In one aspect, the present invention is directed to compositions which are enriched for Neutrophil Inhibitory Factor, a protein that inhibits neutrophil activity and which is not an antibody, an integrin, a selectin or a member of the immunoglobulin superfamily of adhesive proteins and which when isolated from a parasitic worm is a glycoprotein. Recombinant NIFs produced by certain expression systems are not glycosylated. Such non-glycosylated NIFs are considered to be within the scope of the invention. This neutrophil inhibitory activity includes but is not limited to inhibition of one or more of the following activities by neutrophils: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis. Certain NIFs (see Example 14(3)) bind to Mac-1.

According to a preferred embodiment, the Neutrophil Inhibitory Factor comprises a glycoprotein derived from or isolated from a parasitic worm, preferably a nematode, and more preferably a hookworm species, especially canine hookworm species or, alternatively, a Toxocara species, or a compound, preferably a protein, which is substantially similar to said glycoprotein. It is believed that certain isoforms of said glycoprotein are produced by the canine hookworm *Ancylostoma caninum*. By substantially similar is meant that the compound exhibits selective neutrophil inhibitory activity similar to that of the glycoprotein, and, preferably has an $IC_{50}$ of about 500 nM or less, more preferably less than 100 nM, as measured by neutrophil activity assays such as those described herein and does not substantially inhibit platelet aggregation at the neutrophil inhibitory concentrations.

These enriched compositions are enriched for Neutrophil Inhibitory Factor using techniques which include chromatography on Concanavalin A Sepharose, hydroxyapatite or an anion exchange column, gel filtration chromatography preferably using Superdex 200, C4 reverse phase HPLC, isoelectric focusing or a combination of those methods or equivalent methods used for separating proteins or proteinaceous factors. For example, in place of Concanavalin A, other immobilized lectins may be used. In place of Superdex 200, other acrylamide- or agarose-based gel filtration media which fractionate proteins in the appropriate molecular weight range may be used; these include those sold under the tradenames Sephacryl and Superose (Pharmacia). Examples of methods of preparing the enriched compositions of the present invention are described in Examples 2 to 5.

In another aspect of the present invention, methods of preparing enriched compositions comprising Neutrophil Inhibitory Factor are provided. Preferably these enriched compositions are at least about 50% pure, that is, they contain at least about 50% Neutrophil Inhibitory Factor. Preferably, the composition is enriched at least about 200-fold. According to another preferred embodiment, substantially pure Neutrophil Inhibitory Factor is prepared. By "substantially pure" is meant at least about 90 percent pure. More preferably the Neutrophil Inhibitory Factor so prepared is chromatographically pure. According to a preferred aspect, methods of preparing compositions enriched for Neutrophil Inhibitory Factor are provided which comprise subjecting a lysate from a parasitic worm to the following isolation steps (a) chromatography on Concavalin-A Sepharose, and (b) gel filtration on Superdex 200, and (c) chromatography on ceramic hydroxyapatite. The Neutrophil Inhibitory Factor may be then subjected to the further isolation step of reverse phase high performance liquid chromatography (HPLC) using a C4 column.

The Neutrophil Inhibitory Factor of the present invention preferably comprises a purified glycoprotein. This may be determined by evaluating binding to Concanavalin A Sepharose (see Example 2(B)) and by positive testing as a glycoprotein in GlycoTrack™ diagnostic assay for the presence of carbohydrate groups (see Example 7).

One glycoprotein having neutrophil inhibitory activity which has been isolated has the following characteristics: This glycoprotein is acidic and exhibits an isoelectric point of about 4.5 as determined by isoelectric focusing (see Example 3). It has an observed molecular weight of about 41,000 daltons (±3,000) as determined by laser-desorption time-of-flight mass spectrometry (see Example 6). Its behavior when subjected to SDS-polyacrylamide gel electrophoresis indicated that it contained multiple disulfide bonds, since the reduced glycoprotein migrated on the gel at a significantly higher apparent molecular weight (see Example 5). The glycoprotein was demonstrated to specifically inhibit neutrophil activity and not to act as a general cytotoxin in another cell adhesion assay. This glycoprotein was demonstrated to inhibit neutrophil adhesion to vascular endothelial cells and homotypic neutrophil aggregation; one such enriched composition (see Example 2(D)) exhibited an $IC_{50}$ of about 10 nM. An $IC_{50}$ is that concentration of inhibitor giving 50% inhibition of the measured activity (see Example 1). This glycoprotein was demonstrated to inhibit peritoneal inflammatory response when administered intraperitoneally or intravenously in an animal model of acute inflammation. (See Example 16.) This enriched composition was demonstrated to inhibit hydrogen peroxide release from neutrophils and neutrophil adhesion/spreading on plastic. The Example 2(D) preparation had an $IC_{50}$ of about 10 nM. An enriched composition of the neutrophil function inhibitory factor was shown to have no inhibitory effect on platelet aggregation (see Example 13).

A second glycoprotein having neutrophil inhibitory activity has been isolated. This glycoprotein has an observed molecular weight of about 20,000 daltons as determined by molecular sieve chromatography. This glycoprotein was demonstrated to inhibit neutrophil adhesion to vascular endothelial cells and neutrophil adhesion/spreading on plastic.

According to a preferred aspect, the Neutrophil Inhibitory Factor comprises a glycoprotein which is a isolated from a parasitic worm, preferably a nematode. Suitable parasitic worms include those selected from species of the phyla Platyhelminthes, Nematoda, Nematomorpha and Acanthocephala. An especially preferred source are endoparasitic hookworm species, such as those found to infect canines. It is believed that certain isoforms of NIF are produced by canine hookworm Ancylostoma species such as *Ancylostoma caninum*. Another suitable source is the endoparasitic worm species *Toxocara canis*. Substantially similar compounds may be isolated from other nematode species, as well as from other endoparasites of other phyla. Preferred sources include parasites, including parasitic worms, particularly endoparasitic nematodes and especially hookworm species, including *Ancylostoma braziliense, Ancylostoma caninum, Ancylostoma ceylanicum, Ancylostoma duodenale, Ancylostoma japonica, Ancylostoma malayanum, Ancylostoma tubaeforme, Bunostomum phlebotomum, Cyclodontostomum purvisi, Necator americanus, Necator araentinus, Necator suillus,* and *Uncinaria stenocephala*.

According to a preferred aspect of the present invention, the Neutrophil Inhibitory Factor is a protein which includes one or more of the following peptide sequences:
 (1) His-Asn-Gly-Tyr-Arg-Ser-$X_1$-Leu-Ala-Leu-Gly-His-$X_2$-$X_3$-Ile-$X_4$ [SEQ. ID. NO. 1], wherein $X_1$ is Arg, Lys, or Asn; $X_2$ is Ile or Val; $X_3$ is Ser or Gly; and $X_4$ is Thr or Ser;
 (2) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr [SEQ. ID. NO. 2], wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lys or Arg;
 (3) Gly-Glu-Gly-Val-Leu-Tyr-Arg-Ser [SEQ. ID. NO. 3];
 (4) Ile-Ser-Asn-Phe-Ala-Asn-Leu-Ala-Trp-Asp-Arg-$X_{12}$-Glu-Lys-$X_{13}$-Gly-Cys-Ala-Val-$X_{14}$ [SEQ. ID. NO. 4], where in $X_{12}$ is Thr or Ala, $X_{13}$ is Phe or Val; and $X_{13}$ is Val or Ala; and
 (5) His-Val-Val-Cys-His-Tyr-Pro-Lys [SEQ. ID. NO. 5].
Preferably these sequences appear in the following order in the protein (from amino terminal end to carboxy terminal end): (1), (2), (3), (4), (5). Additional amino acid residues or peptide sequences may be interspersed between the above sequences or may be at the amino terminal and/or carboxy terminal end of he protein. (See, e.g., FIG. 7 [SEQ. ID. NOS. 13 to 31].) Since it is believed that a NIF isolated from a particular source may include multiple isoforms, such isoforms are considered to be within the ambit of the present invention. The term "isoform" refers to a family of related proteins from a single organism having homologous sequences of amino acid residues interspersed with variable sequences. According to an especially preferred aspect, the NIF Protein has the amino acid sequence depicted in FIG. 8 [SEQ ID. NO. 32] [SEQ. ID. NO. 33].

Isolation of DNA Sequences That Encode Neutrophil Inhibitory Factor

As described above, one example of Neutrophil Inhibitory Factor ("NIF") of this invention which comprises a glycoprotein has been isolated in substantially pure form. Using reported procedures, those of ordinary skill in the art can use this protein to derive its amino acid sequence. For example, the protein may be analyzed to determine an N-terminal sequence, or fragments of the protein can be produced by enzymatic or other specific digestion procedures and the sequence of the terminal amino acids of those fragments determined. Such amino acid sequences, even if only between five and six contiguous amino acids in length, will provide sufficient information to determine potential DNA sequences of a gene encoding this protein.

If two or three such amino acid fragments are sequenced a plurality of appropriate oligonucleotides can be synthesized using standard procedure, and can be used to probe a genomic or cDNA library from hookworm (or other source) to isolate the gene or fragments thereof encoding the sequenced protein. Those in the art will recognize that these oligonucleotides can be designed using standard parameters such that the oligonucleotide is chosen to encode the chosen acid sequence. For example, it is common to use a mixture of oligonucleotides as a probe for any particular sequence of amino acids, with each oligonucleotide having the same nucleotide base sequence except at specific bases which are varied to take into account the various redundant codons that might code for any particular amino acid. It is of course desirable to choose an amino acid sequence which is encoded by as few oligonucleotides as possible. In addition, the various redundant codons may be specifically selected to represent those codons that are most preferred in, for example, hookworm nucleic acid.

In addition, the above-described isolated pure protein can be used to form antibodies by standard procedures. Such antibodies may include monoclonal or polyclonal antibodies and can be used to screen bacteriophage λgt11 expression libraries containing other source (e.g., hookworm) DNA. In this manner, any particular clone which includes nucleic acid encoding the Neutrophil Inhibitory Factor can be readily identified using standard procedures.

Genomic DNA libraries of a hookworm, for example, can be formed using standard procedure to isolate the genomic DNA of the hookworm, fractionating that DNA using either a random procedure, such as sonication, or a specific procedure such as restriction endonuclease digestion and ligation of those fragments into an appropriate vector, such as a bacteriophage lambda (λ), plasmid or cosmid vector. Such a library can be screened for useful clones by nucleic acid hybridization using the oligonucleotide mixtures described above. More preferably, however, a cDNA library can be constructed by isolation of total hookworm RNA, passage of that RNA over an oligo-dT column to purify the poly(A)-containing RNA (ie., messenger RNA), and reverse transcription of such RNA to produce DNA fragments representative of the RNA (i.e., cDNA). These cDNA fragments can be inserted using standard procedures into any desired vector, for example, an expression vector such as a commercially available *E. coli* expression vector such as bacteriophage λgt11 (for expression in *E. coli*), or into a plasmid pcDNA-1 which can be expressed in mammalian COS7 cells.

The biological activity of the protein expressed in each clone of the plasmid expression library can be readily assayed using the neutrophil inhibitory activity assays described herein or other suitable assays. Alternatively, the antibodies described above can be used to probe for immunoreactive protein expressed from clones in the bacteriophage expression libraries (e.g., λgt11). It is particularly preferred to screen various libraries in sub-pools, for example, of 999 clones at a time to determine which of those sub-pools includes a positive clone. When a positive clone is isolated a grid of the 999 colonies can be formed on a 33×33 plate and each of the 33 clones in each row and column in the plate assayed simultaneously (i.e., in 66 preparations) to identify the desired clone.

Once the desired clone is isolated, its structure is analyzed by standard procedures, for example, by DNA sequencing to determine whether it encodes the whole of the desired protein. If it does not, that clone can be used to screen further cDNA or genomic libraries for other full-length clones, or the DNA can be used to hybrid select RNA present in the hookworm, or other source, and more selective cDNA libraries formed from that RNA using procedures described above.

It should be apparent to those skilled in the art that the oligonucleotide primers can be used in the polymerase chain reaction (PCR) to generate complementary DNA probes. These probes can be used to identify NIF-related proteins from other sources. Preferred are animal, fungal, bacterial or viral sources. In PCR cloning method, single stranded DNA primers of 20–100 nucleotides are derived from the sequence of Ancylostoma NIF. More preferably, primers have the following characteristics: limited degeneracy; adherence to codon usage preferences of the particular species from which the library is constructed and primers that target sequences which are conserved among the seven Ancylostoma NIF isoforms. Each PCR reaction utilizes two primers: a 5-primer that corresponds to the sense strand and a 3'-primer that corresponds to the antisense strand of the NIF coding sequence.

Single stranded cDNA template is generated using poly (A)+ or total RNA prepared from cells of the tissue or organism to be screened. RNA is primed with either random hexanucleotides or oligo d(T) and extended with reverse transcriptase. This reaction product is amplified using an appropriate DNA polymerase (e.g., Taq polymerase), with a sense and antisense primer, on an appropriate thermocycler.

A wide variety of polymerase chain reaction conditions are employed, but initial experiments preferably involve relatively low stringency annealing and elongation steps. Preferred conditions are: cycles 1–3, denaturation at 94° C. for 1 minute, annealing at 37° C. for 1 minute and elongation at 72° C. for two minutes. The ramp time between annealing and elongation steps is extended to at least 2 minutes for these cycles; cycles 4–40, denaturation at 94° C. for 1 minute, annealing at 45° C. for 1 minute and elongation at 72° C. for two minutes. In subsequent experiments, annealing temperature is increased until a single product results from amplification with each primer pair.

Amplification products from individual amplification reactions are used as hybridization probes to screen genomic DNA or cDNA libraries constructed from the tissue from which PCR was effected. DNA or cDNA from any recombinant plaque or colony that hybridized to these amplification products is selected for further analyses.

NIF-related complementary DNAs isolated using the techniques described above are subjected to nucleotide sequence analysis using the procedure of dideoxy sequencing (Sanger et al, 1977, Proc. Natl. Acad. Sci USA 74:5463–5467).

NIF-related cDNA isolates containing open reading frames (i.e., initiating with a methionine and terminating with a TAA, TGA or TAG stop codon) are inserted into suitable vectors for protein expression in either bacterial, yeast, insect or mammalian cells. Expression systems comprise vectors designed to secrete recombinant protein (i.e., fusion of cDNA isolate open reading frame with a known secretion signal sequence for that cell type) into the culture medium. Vectors lacking a homologous secretion signal sequence are also used for expression. Either conditioned media or cell lysate, depending on the expression system used, is tested for inhibitory activity using one or more of the following criteria for neutrophil activation: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis.

As discussed above and as described in Example 10, oligonucleotide probes derived from the peptide sequences of NIF (isolated from the hookworm, *Ancylostoma caninum*) were used in conjunction with the polymerase chain reaction to amplify NIF cDNA sequences. These NIF sequences were used in turn to probe a hookworm cDNA library. Six partial clone isoforms of NIF were isolated in addition to the protypical NIF-1FL full-length clone [SEQ. ID. NOS. 33 to 39]. This example illustrates the utility of this technique for isolation of sequences that are structurally related to NIF.

Applicants note that by using techniques such as those described above, as well as similar and equivalent techniques, DNA sequences which encode Neutrophil Inhibitory Factor from other animal, fungal, bacterial or viral source may be isolated and used to express recombinant Neutrophil Inhibitory Factor.

Should immunoreactive material be expressed from an expression library, the expression vectors described above, or derivatives thereof, can be used for expression of recombinant protein with biological activity equivalent to that of the native protein. Such recombinant protein is useful in this invention.

Using one example of a Neutrophil Inhibitory Factor of the present invention, peptide fragments were produced and their amino acid sequences determined. This experiment is described in Example 9. The amino acid sequences obtained for the proteolytic fragments are set forth in FIG. 7.

An example of NIF has been cloned from a canine hookworm cDNA library as described in Example 10. Seven phage isolates were isolated for sequencing purposes. The nucleotide sequence for the cDNA of one of the isolated clones (clone 1FL) is depicted in FIG. 8 [SEQ. ID. NO. 32]. Deduced partial amino acid sequences for other of the isolated NIF isoform clones are depicted in FIG. 9 [SEQ. ID. NOS. 34 to 39].

According to one aspect, the present invention is directed to a DNA isolate which encodes a protein containing one or more of the following peptide sequences:

(1) His-Asn-Gly-Tyr-Arg-Ser-$X_1$-Leu-Ala-Leu-Gly-His-$X_2$-$X_3$-Ile-$X_4$ [SEQ. ID. NO. 1], wherein $X_1$ is Arg, Lys, or Asn; $X_2$ is Ile or Val; $X_3$ is Ser or Gly; and $X_4$ is Thr or Ser;

(2) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr [SEQ. ID. NO. 2], wherein $X_5$ is Phe or Tyr; $X_6$ is Arg, Ser, or Thr; $X_7$ is Lue or Met; $X_8$ is Glu or Lys; $X_9$ is Glu or Asp; $X_{10}$ is Ala or Ser; and $X_{11}$ is Lys or Arg;

(3) Gly-Glu-Gly-Val-Leu-Tyr-Arg-Ser [SEQ. ID. NO. 3];

(4) Ile-Ser-Asn-Phe-Ala-Asn-Leu-Ala-Trp-Asp-Arg-$X_{12}$-Glu-Lys-$X_{13}$-Gly-Cys-Ala-Val-$X_{14}$ [SEQ. ID. NO. 4], wherein $X_{12}$ is Thr or Ala, $X_{13}$ is Phe or Val; and $X_{14}$ is Val and or Ala; and (5) His-Val-Val-Cys-His-Tyr-Pro-Lys.

The DNA isolate may also include additional sequences which do not code for portions of the finished protein, such as introns, and/or sequences which code for intervening amino acid residues or peptides in addition to the above peptide sequences. According to an especially preferred aspect, the coding region of the DNA isolate has the nucleotide sequence and/or codes for a protein having the deduced amino acid sequence set forth in FIG. 8.

Isolation of NIF-like Proteins

By using the techniques described herein and other techniques in the art, NIF-like proteins may be isolated from any source, whether, animal, bacterial, fungal, viral or other source suspected of having a NIF. Such NIF-like proteins and nucleic acid sequences encoding them may be isolated by methods such as probing a genomic or cDNA library from the source suspected of having a NIF using oligonucleotide probes sufficiently complementary to a nucleic acid sequence encoding a NIF such as those sequences depicted in FIG. 8 [SEQ. ID. NO. 32] [SEQ. ID. NO. 33], and then isolating and expressing those nucleic acid sequences which hybridize to the probes as described herein. Such probes have a sufficient number of nucleotides to describe a unique sequence. Typically such probes will have at least about 12 nucleotides. One preferred group of probes include those of the sequences: 5'-CTCGAATTCT(GATC)GC(ATC)AT(ATC)-(CT)T(GATC)GG(ATC)TGGGC-3' [SEQ. ID. NO. 6] and 5'-CTCGAATTCTT(TC)TC-TGG(GA)AA(GA)CG(GA)TC(GA)AA-3' [SEQ. ID. NO. 7].

Alternatively, NIF-like proteins and nucleic acids coding for such proteins may be isolated by probing a sample of nucleic acid from a source suspected of having a NIF with an oligonucleotide probe having at least about 12 nucleotides which is complementary to a nucleic acid sequence known to encode a NIF, such as the sequence depicted in FIG. 8 and isolating those nucleic acid sequences, such as a gene, which are sufficiently complementary to the oligonucleotide probe to hybridize thereto. The isolated nucleic acid sequence may then be cloned and expressed using art techniques.

Expression of Recombinant Neutrophil Inhibitory Factor

The cDNA encoding Neutrophil Inhibitory Factor may be inserted into a replicable vector for expression, resulting in the synthesis of biologically active recombinant Neutrophil Inhibitory Factor. Many vectors are available for expression of heterologous proteins and selection of the appropriate vector will depend primarily on the desired properties of the host cell. Each of the available vectors contain various components specific to the host cell to be transformed. The vector components or control elements generally include, but are not limited to, one or more of the following: a signal sequence, an origin of replication, one or more marker genes, a promoter, an enhancer element and a transcription termination sequence. Once the expression vector containing the inhibitor is constructed, a suitable host cell is transfected or transformed with the expression vector, and recombinant Neutrophil Inhibitory Factor is purified either from the host cell itself or the host cell growth medium.

In general, the signal sequence may be a component of the vector, or it may be encoded by the Neutrophil Inhibitory Factor DNA that is inserted into the vector. If the native inhibitory factor is a secreted gene product (i.e., from the hookworm (or other source) cells), then the native pro-Neutrophil Inhibitory Factor from hookworm DNA may encode a signal sequence at the amino terminus of the polypeptide that is cleaved during post-translational processing of the polypeptide to form the mature Neutrophil Inhibitory Factor.

All vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacterial, yeast, insect and mammalian cells. The origin of replication from the plasmid pBR322 is suitable for most for most gram-negative bacteria, the 2 $\mu$ plasmid origin is suitable for yeast, the baculovirus origin is suitable for some insect cells (e.g., Sf9 cells; ATCC# CRL1711) and various viral origins (e.g., SV40, adenovirus) are useful for cloning vectors in mammalian cells.

Expression vectors should contain a selection gene, also termed a selectable marker. This gene encodes a protein necessary for the survival or growth of transformed host cells grown in selective culture medium. Host cells not transformed with the vector containing the selection gene will not survive in the culture medium. Typical selection genes encode proteins that (a) confer resistance to antibiotics or other toxins, e.g., ampicillin, neomycin or methotrexate, (b) complement auxotrophic deficiencies, or (c) supply critical nutrients not available from complex media.

Expression vectors contain promoters that are recognized by the host organism. Promoters are untranslated sequences located upstream (5') to the start codon of a structural gene (generally within about 100 to 1000 base pairs) that control the transcription and translation of a particular nucleic acid sequence, such as hookworm Neutrophil Inhibitory Factor, to which they are operably linked. A large number of promoters recognized by a variety of potential host cells are well known. These promoters are operably linked to DNA encoding the Neutrophil Inhibitory Factor by inserting the latter into the vector in a way such that the 5' terminus of the Neutrophil Inhibitory Factor DNA is in close linear proximity to the promoter.

Transcription of a DNA encoding the Neutrophil Inhibitory Factor of this invention by higher eukaryotes is often increased by inserting an enhancer sequence into the vector. (For example, see, Kriegler, M., 1991, *Gene Transfer and Expression*, pages 4–18, W. H. Freeman, New York). Enhancers are cis-acting elements of DNA, usually about 10–300 base pairs in length, that act on a promoter to increase its transcription. Enhancers are relatively orientation and position independent. Typically, one will use an enhancer from a eukaryotic cell virus for expression in mammalian cells. Examples include the SV40 enhancer, the cytomegalovirus early promoter enhancer and the adenovirus enhancers.

Expression vectors used in eukaryotic (i.e., non-bacterial) host cells will also contain sequences necessary for the termination of transcription and for stabilizing the mRNA. Such sequences are commonly available from the 5' end and, occasionally from the 3' untranslated regions of eukaryotic or viral DNAs.

Suitable host cells for the expression vectors described herein include bacterial, yeast, insect or mammalian cells. Preferred bacteria are *E. coli* strains, preferred yeast are *Saccharomyces cerevisiae* and *Pichia pastoris*, a preferred insect cell line is Sf9 (ATCC# CRL 1711) and preferred mammalian cell lines are COS-7 (ATCC# CRL 1651), CHO-K1 (ATCC# CCL 61) and HeLa (ATCC# CCL 2). These examples of host cells are illustrative rather than limiting. Preferably the host cell should secrete minimal amounts of proteolytic enzymes. Particularly suitable host cells for the expression of glycosylated Neutrophil Inhibitory Factor are derived from multicellular organisms. Such host cells are capable of complex post-translational processing and glycosylation activities of expressed proteins.

Host cells are transfected and preferably transformed with the above-described expression vectors of this invention and cultured in conventional nutrient media modified as appropriate for inducing promoters and selecting transformants. Transfection refers to the taking up of an expression vector by a host cell. Numerous methods of transfection are known to the ordinarily skilled artisan, for example, calcium phosphate coprecipitation, spheroplasting transformation and electroporation. Successful transfection is generally recognized when any indication of the operation of this vector occurs within the host cell. Transformation means introducing DNA into an organism so that the DNA is replicable, either as an extrachromosomal element or chromosomal integration. Depending on the host cell used, transformation is done using standard techniques appropriate to such cells (e.g., calcium chloride or electroporation for bacterial cells; spheroplasting or electroporation for yeast cells; calcium phosphate or electroporation for insect and mammalian cells).

The recombinant hookworm neutrophil inhibitor preferably is recovered from the culture medium as secreted polypeptide, although it may also be recovered from host cell lysates when directly expressed without a signal or secretory sequence. The expressed hookworm neutrophil inhibitor may be purified from culture medium or from cell lysates by a variety of separation techniques including, but not limited to, gel filtration, affinity and ion exchange chromatography, hydroxyapatite chromatography, C4 reverse-phase HPLC and preparative isoelectric chromatography.

Amino Acid Sequence Variants of the Neutrophil Inhibitory Factor

Amino acid sequence variants of the Neutrophil Inhibitory Factor are prepared by introducing nucleotide changes into the Neutrophil Inhibitory Factor DNA, isolated as described above. Such variants include substitutions of residues within the amino acid sequence of the Neutrophil Inhibitory Factor. Any combination of substitutions can be made to arrive at the final construct, provided that the final construct possesses certain desired characteristics. The desired characteristic includes, but is not limited to, an increased potency over the wild-type Neutrophil Inhibitory Factor. One possible method for preparing variants of the Neutrophil Inhibitory Factor is mutagenesis with base-specific chemical mutagens as described in detail by Pine and Huang (1987, Methods Enzymol. 154, 415–430). Once variant inhibitor DNAs have been constructed, variant recombinant forms of Neutrophil Inhibitory Factor may be synthesized utilizing expression systems as described above.

Preparation of Fragments of Neutrophil Inhibitory Factor

Another aspect of the present invention is directed to peptide fragments having neutrophil inhibitory activity which are prepared by proteolytic or chemical methods starting with the chromatographically pure Neutrophil Inhibitory Factor of the present invention.

Active peptide fragments, with or without sugar moieties, may be generated by using enzymatic or chemical techniques. Proteolytic cleavage can be accomplished by digestion of the inhibitor with one or more of the following enzymes: chymotrypsin, trypsin, leucine aminopeptidase, endoproteinase Glu-C, endoproteinase Lys-C, endoproteinase Arg-C, or endoproteinase Asp-N (Carrey, E. A., 1989 *Protein Structure. A Practical Approach*, pp. 117–143, T. E. Creighton, ed. IRL Press, New York). Chemical digestion of the inhibitor may be accomplished by cyanogen bromide, hydroxylamine, or 2-nitro-5-thiocyanobenzoate cleavage (Carrey, E. A., 1989, *ibid.*). Sugar moieties can be removed from either the peptide fragments or intact neutrophil inhibitory protein enzymatically with one or more of the following enzymes: glycopeptidase F, endoglycosidase H, endoglycosidase F, or endoglycosidase D as described by Keesey (Keesey, J., 1987 *Biochemica Information*, pp. 147–165, J. Keesey, ed., Boehringer Mannheim Biochemicals, Indianapolis). Alternatively, glycosylation of the intact inhibitor may be suppressed by expression of the protein in bacterial cells or by the inclusion of inhibitors of glycosylation in the eukaryotic cell culture growth medium. Inhibitors of glycosylation and their uses are described in the art (e.g., Keesey, J. 1987 *Biochemica Information*, pp. 135–141, J. Keesey, ed., Boehringer Mannheim Biochemicals, Indianapolis). Separation of active fragments from inactive fragments may be accomplished by conventional, low, medium, or high pressure chromatographic techniques known in the art.

Utility and Applications

The Neutrophil Inhibitory Factor of the present invention has potent neutrophil inhibitory activity and, thus, may be used as an inhibitor of neutrophil activity, including neutrophil activation, as well as for preventing or treating inflammatory conditions characterized by neutrophil activation.

Thus, the Neutrophil Inhibitory Factor will be useful in the treatment of inflammation in which neutrophils play a significant role. While applicants do not wish to be bound to any theory or mode of activity, it is believed that this compound will interfere with the inflammatory response which is set into action by neutrophil-endothelial cell interactions. Thus, where adhesion of neutrophils to the endothelium is prevented, the neutrophils will be unable to transmigrate to tissue to elicit a proinflammatory response with consequent tissue damage. Inhibition of neutrophil-neutrophil adhesion and/or aggregation by these compounds should also prevent microvascular occlusion. Thus, these compounds will be useful in treating a variety of clinical disorders, including shock, stroke, acute and chronic allograft rejection, vasculitis, autoimmune diabetes, rheumatoid arthritis, inflammatory skin diseases, inflammatory bowel disease, adult respiratory distress syndrome (ARDS), ischemia-reperfusion injury following myocardial infarction, in which neutrophil infiltration and activation has been implicated and acute inflammation caused by bacterial infection, such as sepsis or bacterial meningitis.

The ability of the Neutrophil Inhibitory Factor of the present invention to inhibit neutrophil activity makes it useful in inhibiting the physiological processes of inflammation, ischemia, and other neutrophil mediated tissue damage. The specific activities of the Neutrophil Inhibitory Factor in carrying out these related functions makes it particularly useful as therapeutic and/or diagnostic agents.

Neutrophil inhibitory activity may be demonstrated by various assays, including neutrophil adhesion to endothelial cells or plastic, homotypic neutrophil aggregation and hydrogen peroxide release by neutrophils. See Example 1.

Antibodies, both monoclonal and polyclonal, directed to Neutrophil Inhibitory Factor of the present invention are useful for diagnostic purposes and for the identification of concentration levels of the subject peptides in various biological fluids. To prepare the subject antibodies, any one of a number of conventional techniques which are known in the art can be employed. In one such technique, polyclonal antibodies are synthesized by injecting an animal (for example a rabbit) with one or more compounds of the invention. After injection, the animal naturally produces antibodies to these compounds. When the antibody concentration (or titer) reaches a sufficient level, antibody-containing blood, called antiserum, is then drawn from the animal, serum is prepared, and the compound-specific antibody is isolated from other antibodies in the serum by any one of a number of separation techniques (for example, affinity chromatography). Monoclonal antibodies may be prepared using the technique of Kohler and Milstein, Nature 256, 495–497 (1975) and other conventional techniques known to those skilled in the art. (See, e.g., Harlow and Lane, *Antibodies. A Laboratory Manual* (Cold Spring Harbor Laboratory, 1988) the disclosures of which is incorporated herein by reference).

An additional aspect of the present invention is directed to monoclonal antibodies which recognize Neutrophil Inhibitory Factor. Also considered as part of the present invention are hybridomas which synthesize such monoclonal antibodies. These hybridomas are produced by conventional techniques such as those described by Harlow and Lane, Id., the disclosures of which is incorporated herein by reference.

A further aspect of the present invention is directed to immunoassays using the antibodies against Neutrophil Inhibitory Factor. Depending on the particular use, one of various immunoassay formats may be selected. Suitable immunoassays are described by Harlow and Lane, Id. see especially pages 553 to 612. The disclosures of which are incorporated herein by reference. These immunoassays may be used as diagnostics such as to detect infection of a mammalian host by a parasitic worm, by assay for Neutrophil Inhibitory Factor from a parasitic worm in a tissue of the mammalian host. Also such immunoassays may be used in the detection and isolation of Neutrophil Inhibitory Factor from tissue homogenates, cloned cells and the like.

In another aspect of the present invention, the Neutrophil Inhibitory Factor (NIF) can be used in a test method to screen other compounds, such as small molecule peptide analogs, for neutrophil inhibitory activity. According to one embodiment, a binding assay is used to establish binding levels of detectably labelled NIF to neutrophils. Suitable detectable labels to be used for labelling NIF include conventionally used enzyme labels, radioactive isotopes and other labels known to those skilled in the art. According to one suitable assay protocol, labelled NIF and neutrophils are co-incubated in solution for a sufficient time to allow binding. Unbound labelled NIF is removed from bound NIF by methods such as centrifugation, filtration or other suitable methods and bound NIF is determined. According to an alternative protocol, neutrophils are immobilized on a plastic surface by natural adhesion or chemical fixation such as by glutaraldehyde or similar chemicals; the labelled NIF is co-incubated with the immobilized neutrophils and unbound NIF is removed by washing. Bound NIF is determined. According to a preferred alternative screening protocol, Mac-1 complexes from a detergent extract of human leukocytes are captured by anti-Mac-1 monoclonal antibodies that are immobilized to a plastic surface. Labeled NIF is co-incubated with the immobilized Mac-1 and unbound NIF is removed by washing. Bound NIF is determined. Compounds, such. as small molecule peptide analogs, are screened for neutrophil inhibitory activity according to the following protocol. Test compounds are preincubated in solution with neutrophils or immobilized Mac-1 and the preincubated solution brought into contact with labelled NIF. The effect of test compound on NIF-neutrophil binding or NIF-Mac-1 binding is then determined.

With suitable adjuvants NIF can be used as a vaccine against parasitic worm infections in mammals. Immunization with NIF vaccine may be used in both the prophylaxis and therapy of parasitic infections. NIF fragments and synthetic polypeptides having the amino acid sequence of NIF may also be used as vaccines. Disease conditions caused by parasitic worms may be treated by administering to an animal infested with these parasites substances which antagonize NIF. Compounds may be screened for their anti-NIF effect according to the screening method described herein above. Examples of such antihelminic agents include antibodies to NIF, both naturally occurring antibodies isolated from serum and polyclonal and monoclonal antibodies described hereinabove. Chemically synthesized compounds which act as inhibitors of NIF also are suitable antihelminic agents.

Formulations

The enriched compositions of the present invention may be formulated and used as tablets, capsules or elixirs for oral administration; suppositories for rectal administration; sterile solutions, suspensions for injectable administration; and the like. The dose and method of administration can be tailored to achieve optimal efficacy but will depend on such factors as weight, diet, concurrent medication and other factors which those skilled in the medical arts will recognize. Generally, an amount between 0.01 µg/kg to 100 mg/kg body weight/day is administered dependent upon the potency of the composition used.

The present invention also encompasses pharmaceutical compositions prepared for storage and subsequent administration which comprise a pharmaceutically effective amount of an enriched composition as described herein in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

In practicing the methods of the invention, the enriched compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, nasally or intraperitoneally, employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for the compositions of the present invention can range broadly depending upon the desired affects and the therapeutic indication. Typically, dosages will be between about 0.01 µg and 100 mg/kg, preferably between about 0.01 and 10 mg/kg, body weight. Administration is preferably parenteral, such as intravenous on a daily or as-needed basis.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Assays of Neutrophil Inhibitory Activity

The Neutrophil Inhibitory Factor of the present invention demonstrated activity in inhibiting neutrophil function as measured by neutrophil-HUVEC and neutrophil-plastic adhesion assays, homotypic neutrophil aggregation assay and hydrogen peroxide release assay. This inhibitory factor was isolated from hookworm tissue lysates as an enriched composition by a variety of methods including gel filtration chromatography, chromatography on hydroxyapatite and concanavalin A sepharose, C4 reverse-phase HPLC, Mono-Q ion exchange chromatography and preparative isoelectric focusing. The isolated factor appears to inhibit neutrophil adhesion to endothelial cell monolayers by inhibiting neutrophil activation.

(A) Cells and Reagents

Primary human umbilical vein endothelial cells (HUVEC), obtained from Clonetics (San Diego, Calif.), were maintained in EGM-UV medium (Clonetics) with 15% fetal bovine serum (FBS), in a 5% $CO_2$ atmosphere. HUVEC were passaged twice and used to seed fibronectin-coated 96 well microtiter plates (Collaborative Research, Bedford, Mass.) for adhesion assays.

The protease inhibitors E64, pepstatin A, chymostatin and APMSF were obtained from Calbiochem (La Jolla, Calif.).

Neutrophils were isolated using Mono-Poly resolving medium (ICN Biomedicals, Costa Mesa, Calif.) from either heparinized or citrated human blood following the instructions of the manufacturer. Neutrophils were resuspended in HSA buffer (RPMI1640 with 10 mM HEPES pH 7.4, 1.2 mM CaCl, 1.0 mM MgCl, 1% human serum albumin) at a concentration of $6.6 \times 10^6$ cells/mL and used within one hour after isolation.

Neutrophils were fluorescently labelled by the following procedure. The cells were washed once in Hank's balanced salt solution (HBSS) and resuspended at $1 \times 10^7$ cells/mL in HBSS containing 20 Mg/mL calcein (Molecular Probes; Eugene, Oreg.). The calcein was initially solubilized in 50 µl dry dimethylsulfoxide prior to its addition to the HBSS. Cells were incubated at 37° C. with occasional mixing by inversion. After 45 minutes incubation the cells were chilled on ice for 5 minutes and then washed twice with ice-cold HSA buffer. Labelled neutrophils were resuspended in HSA buffer at $1.3 \times 10^7$ cells/mL for use in adhesion assays.

(B) Neutrophil-HUVEC Adhesion Assays

Calcein-labelled neutrophils (175 µl at $1.32 \times 10^7$ cells/mL) were preincubated for 10 minutes at room temperature with 175 µl of test fraction (diluted in HSA buffer) in the presence of 160 nM phorbol 12-myristate 13-acetate (PMA; Sigma, St. Louis, Mo.). PMA is solubilized in dimethylsulfoxide at a stock concentration of 1.6 mM. A 96 well plate was used for this assay. One hundred microliters of this suspension was then aliquoted into each of three replicate wells that contained HUVEC monolayers. Neutrophils were incubated with the HUVEC monolayer for 30 minutes at 37° C. To remove non-adherent cells, wells were first filled with 250 µl HSA buffer, sealed with parafilm and then centrifuged inverted for 3 minutes at 75×g. Inverted plates were then placed on a rocking platform shaker for 5 minutes, after which contents were decanted off and wells were washed twice with 100 µl HSA buffer. Adherent neutrophils were lysed in 100 µl 0.1% (v/v) Triton X-100 (in 50 mM Tris HCl pH 7.4), and agitated for 10 minutes on a plate shaker. Twenty five microliters of the neutrophil/endothelial cell lysate was transferred to a 96 well microtiter plate that contained 100 µl of 50 mM Tris pH 7.4, and the wells were read at 530 nm (485 nm excitation) on a Cytofluor fluorometric plate reader (Millipore; Bedford, Mass.).

The hydroxyapatite pool preparation of hookworm Neutrophil Inhibitory Factor (see Example 1(D)) inhibited neutrophil adhesion to HUVEC monolayers with an $IC_{50}$ of about 10 nM.

(C) Neutrophil-Plastic Adhesion Assay

Neutrophils (20 µl at $6.6 \times 10^6$ cells/mL) were incubated with 5 µL PMA (0.8 µM) for 5 minutes at room temperature in a 0.5 mL polypropylene test tube. Twenty microliters of test fraction, diluted in HSA buffer, was added and the suspension was mixed gently. Aliquots of 10 µl of this suspension were added in triplicate to microtiter wells of 60-well HCA (Terasaki) plates (Nunc, Naperville, Ill.). Neutrophils were incubated 5 minutes at 37° C. and non-adherent cells were removed by submerging the plate 6 times in HBSS.

Adherent neutrophils were quantitated by counting under an inverted light microscope. Binding was quantitated visually. PMA-activated neutrophils spread and adhere tightly to polystyrene plastic. Non-activated neutrophils (i.e., in the absence of PMA) remain round and translucent and do not adhere tightly to plastic. Adherent neutrophils were larger, rhomboid in shape and more opaque, with a granular appearance. In the absence of Neutrophil Inhibitory Factor, greater than 80% of PMA-activated neutrophils rapidly and irreversibly bound plastic, underwent shape change and were not removed by the gentle wash procedure. Moreover, fractions containing the Ancylostoma Neutrophil Inhibitory Factor exhibited a profound inhibitory effect on plastic binding by activated neutrophils.

The hydroxyapatite pool preparation of hookworm Neutrophil Inhibitory Factor (see Example 1(D)) inhibited neutrophil adhesion to plastic in this assay with an $IC_{50}$ of about 10 nM.

(D) Homotypic Neutrophil Aggregation

Neutrophil aggregation was performed at 37° C. in a Scienco dual channel aggregometer (Morrison, Colo.). Neutrophils (190 µl at $6.6 \times 10^6$ cells) were preincubated with 200 µl test fraction (diluted in HSA Buffer) in a glass cuvette (Scienco) for 2 minutes at room temperature. Ten microliters of PMA were added to initiate aggregation (80 nM final). The inhibition of neutrophil aggregation was measured at the maximum aggregation response 5 minutes after the addition of PMA.

The hydroxyapatite pool preparation of Neutrophil Inhibitory Factor (see Example 1(D)) inhibited neutrophil adhesion with an $IC_{50}$ of about 10 nM.

(E) Hydrogen Peroxide Release Assay

Neutrophils ($6.6 \times 10^6$ cells/mL) were incubated with test fractions in Release Assay Buffer (HBSS with 25 mM glucose, 10% FBS, 200 µg/mL phenol red, 32 µg/mL horseradish peroxidase) for 5 minutes at 37° C. Incubation vessels consisted of 1.5 mL plastic test tubes that were precoated with HBSS containing 50% FBS at 37° C. for 60 minutes; coated tubes were washed twice with 0.15 M NaCl before use. FMLP (Sigma; St. Louis, Mo.) at a final concentration of 250 µM was added and the neutrophil/test compound suspension was incubated at 37° C. for 60 minutes. Cells were pelleted by centrifugation at 8000×g for 3 minutes and 200 µl of supernatant was transferred to a 96 well microtiter plate. Ten microliters of 1 N. NaOH was added to each well and absorbance was read at 610 nm with a Molecular Devices ThermoMax plate reader. Hydrogen peroxide concentrations were determined by using a standard curve. Data points were done in duplicate.

The hydroxyapatite pool preparation of hookworm Neutrophil Inhibitory Factor inhibited hydrogen peroxide release from neutrophils with an $IC_{50}$ of about 10 nM.

Example 2

Isolation of Native Neutrophil Inhibitory Factor From Hookworm Lysate (A) Preparation of Hookworm Lysate Frozen canine hookworms were obtained from Antibody Systems (Bedford, Tex.). Hookworms were stored at −70° C. until used for homogenate.

Hookworms were homogenized on ice in homogenization buffer [0.02M Tris-HCl pH 7.4, 0.05 M NaCl, 0.001 M $MgCl_2$, 0.001 M $CaCl_2$, $1.0 \times 10^{-5}$M dithiothreitol, $1.0 \times 10^{-5}$ M E-64 Protease Inhibitor (CAS 66701-25-5), $1.0 \times 10^{-6}$M pepstatin A (isovaleryl-Val-Val-4-amino-3-hydroxy-6-methyl-heptanoyl-Ala-4-amino-3-hydroxy-6-methylheptanoic acid, CAS 26305-03-3), $1.0 \times 10^{-5}$M chymostatin (CAS 9076-44-2), $2.0 \times 10^{-5}$M APMSF (amidinophenylmethylsulfonyl fluoride-HCl), 5% (v/v) glycerol) using a Tekmar Tissuemizer homogenizer. The protease inhibitors E64, pepstatin A, chymostatin, and APMSF were obtained from Calbiochem (La Jolla, Calif.). Approximately 3–6 mL of homogenization buffer was used to homogenize each gram of frozen worms (approximately 500 worms). Insoluble material was pelleted by two sequential centrifugation steps: $40,000 \times g_{max}$ at 4° C. for 20 minutes followed by $105,000 \times g_{max}$ at 4° C. for 40 minutes. The supernatant solution was clarified by passage through a 0.2 μm cellulose acetate filter (CoStar).

(B) Concanavalin A Sepharose Chromatography of Hookworm Lysate

Hookworm lysate (79 mL) was adsorbed to 16 mL of Concanavalin A Sepharose (Pharmacia) pre-equilibrated with Con A buffer [0.02 M Tris-HCl, pH 7.4, 1 M NaCl, 0.001 M $CaCl_2$, 0.001 M $MnSO_4$, $1 \times 10^{-5}$ M dithiotreitol] by recycling it through a 1.6×8 cm column at a flow rate of 3 mL/min (90 cm/hour) for 2 hours. The column was at room temperature (24° C.) while the reservoir of lysate was maintained on ice throughout the procedure. The column was subsequently washed with 80 mL of Con A buffer. The Con A buffer in the column was displaced with buffer containing 0.5 M methyl-alpha-mannopyranoside and flow stopped for 30 minutes. Flow was then restarted at a flow rate of 0.5 mL/min (15 cm/hour). Material that had inhibitory activity in neutrophil function assays was eluted with approximately three column volumes of Con A buffer containing 0.5 M methyl-alpha-mannopyranoside (CAS 617-04-09). The yield of neutrophil adhesion inhibitory activity in this step was approximately 38%.

FIG. 1 depicts Concanavalin A Sepharose chromatography of the hookworm lysate performed as described above. Absorbance at 280 nm was plotted as a function of time.

(C) Molecular Sieve Chromatography Using Superdex 200

Active fractions eluted from immobilized Concanavalin A (see step (B) above) and concentrated by ultrafiltration at 4° C. using an Amicon stirred cell equipped with a 10,000 dalton cut-off membrane (YM10), then 5–20 mL of the concentrate were loaded on a 2.6 cm×60 cm column of Superdex 200 prep (Pharmacia) attached in series with an identical column (combined dimensions of 2.6×120 cm). Both columns were pre-equilibrated with 0.01 M potassium phosphate, pH 7.35, 0.150 M NaCl, $1 \times 10^{-5}$ M dithiotreitol at 24° C. The chromatography was conducted at a flow rate of 1.5 mL/min; anti-adhesion activity typically eluted 395–410 mL into the run ($K_{av}$ of 0.46, see FIG. 2). This elution volume would be expected for a globular protein with a molecular mass of 50,000. The yield of neutrophil function inhibitory activity in this step was typically 70–80%. If the ionic strength of the chromatography buffer employed was decreased to 0.01 M sodium phosphate, pH 7.00 and 10% (v/v) glycerol added, the activity eluted substantially earlier ($K_{av}$=0.34) suggesting that under such conditions the protein either aggregates or changes its conformation (assuming a larger Stoke's radius).

Figure 2:
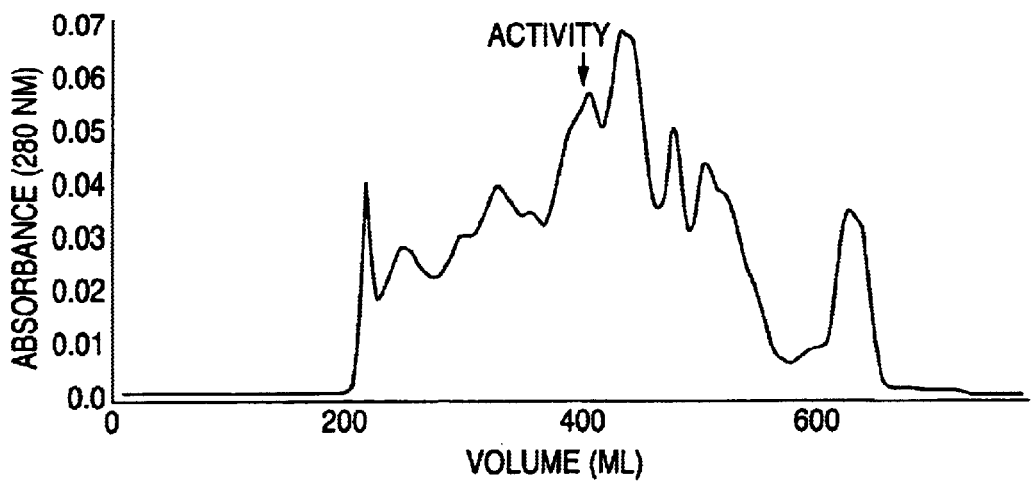
FIG. 2 depicts a chromatogram of Concanavalin A-purified hookworm lysate run on the Example 2(C) Superdex 200 column.

FIG. 2 depicts Superdex 200 Chromatography of Concanavalin A-Purified Hookworm Lysate. Absorbance at 280 nm is plotted versus elution volume. Active fractions eluted from immobilized Concanavalin A (see step (B) above) and concentrated by ultrafiltration at 4° C. using an Amicon stirred cell equipped with a 10,000 dalton cut-off membrane (YM10), then 5–20 mL of the concentrate were loaded on a 2.6 cm×60 cm column of Superdex 200 prep (Pharmacia) attached in series with an identical column (combined dimensions of 2.6×120 cm). Both columns were pre-equilibrated with 0.01 M potassium phosphate, pH 7.35, 0.150 M NaCl, $1 \times 10^{-5}$ M dithiotreitol at 24° C. The chromatography was conducted at a flow rate of 1.5 mL/min; activity eluted 395–410 mL into the run ($K_{av}$ of 0.46).

(D) Ceramic-Hydroxyapatite Chromatography

Material purified by molecular sieve chromatography was concentrated five-fold by ultrafiltration using an Amicon stirred cell equipped with a 10 kilodalton cut-off membrane at 4° C. and then diluted ten-fold with water. The desalted sample was loaded on a 0.8×10 cm column of ceramic hydroxyapatite ("HA") (Pentax, American International Chemical, Inc., Natick, Mass., 2 μm) equilibrated with 0.001 M potassium phosphate, pH 7.00, $1 \times 10^{-5}$ M $CaCl_3$, $1.0 \times 10^{-5}$ M dithiothreitol at 24° C. The loading was conducted at a flow rate of 0.8 mL/min (95.5 cm/hour). The column was developed with a 50 mL linear gradient of potassium phosphate ranging from 0.001 M to 0.0375 M at a flow rate of 0.5 mL/minute. Neutrophil inhibitory activity eluted sharply at 0.025 M potassium phosphate and then trailed to 0.0325 M potassium phosphate (fractions 37 to 48). The yield of activity in this step was approximately 48%.

Figure 3:
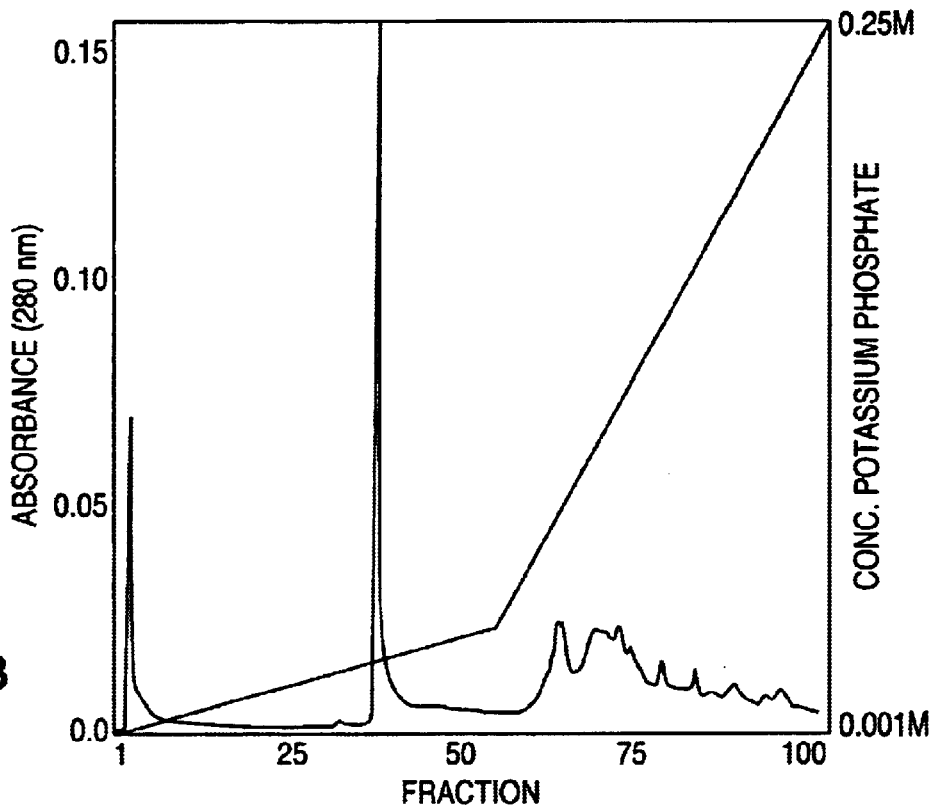
FIG. 3 depicts a chromatogram of the Concanavalin A Sepharose/Superdex purified hookworm lysate run on the Example 2(D) ceramic hydroxyapatite column.

FIG. 3 depicts Ceramic Hydroxylapatite Chromatography of Superdex/Concanavalin A-Purified Hookworm lysate plotting absorbance at 280 nm and potassium phosphate concentration versus fraction number. Neutrophil inhibitory activity eluted in fractions 37 to 48.

(E) Reverse Phase HPLC

Hookworm lysate fractionated by chromatography on Concanavalin A Sepharose, Superdex, and ceramic hydroxylapatite (~100 μg) was loaded on to a 0.48×15 cm column of 300 Å C4 (Vydac) which was then developed with a linear gradient of 0–60% acetonitrile in 0.1% trifluoroacetic acid at 1 mL/minute with a rate of 1% change in acetonitrile/minute. Neutrophil inhibitory activity typically elutes between 41 and 45% acetonitrile, the activity corresponding with a broad peak.

Figure 4:
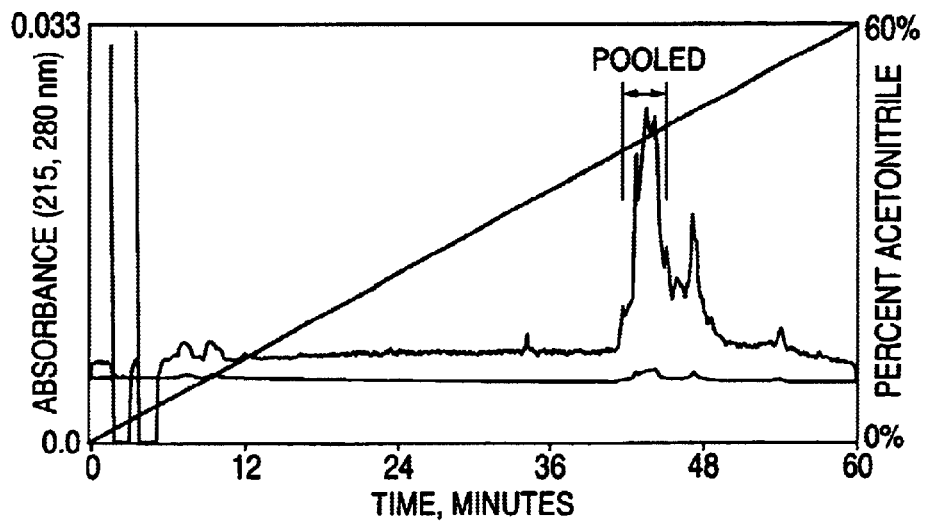
FIG. 4 depicts a chromatogram from reverse phase HPLC of hookworm lysate isolated by Concanavalin A Sepharose, Superdex 200 and hydroxyapatite chromatography as described in Example 1(E).

FIG. 4 depicts the results of reverse phase HPLC of the Neutrophil Inhibitory Factor. Inhibitory activity eluted between 43 and 45% acetonitrile, the activity corresponding with a broad peak at 43–45 minutes.

TABLE I

Summary of Example Purification

| FRACTIONATION STEP | PROTEIN (mg) | PERCENT ACTIVITY | SPECIFIC ACTIVITY | FOLD PURIF. |
|---|---|---|---|---|
| EXTRACTION | 528 | 100 | 0.2 | 1 |
| ConA ELUATE | 21.7 | 38 | 1.8 | 9 |
| SUPERDEX POOL | 1.5 | 25 | 16.7 | 88 |
| HYDROXYAPATITE POOL | 0.3 | 12 | 40.0 | 200 |

Example 3

Isolation of the Neutrophil Inhibitory Factor From Hookworm Lysate Using Preparative Isoelectric Focusing Hookworm lysate was partially fractionated and desalted by molecular sieve chromatography on a 2.6 cm×60 cm column of Superdex 200 prep (Pharmacia) attached in series with an identical column (combined dimensions of 2.6×120 cm). Both columns were pre-equilibrated with 0.01 M sodium phosphate, pH 7.00, 10% (v/v) glycerol at 24° C. Adhesion inhibiting fractions eluting at 350–370 mL were diluted to 55 mL by the addition of 1.4 mL of 40% Biolyte 3–10 ampholyte (BioRad) and 10% (v/v) glycerol. This mixture was focused with a constant power of 12 W for 5 hours at 4° C. in a Rotofor preparative isoelectric focusing prep cell (BioRad). Twenty fractions were harvested; inhibitory activity was detected in fractions 6–9, corresponding to an isoelectric point of 4.5. The overall yield of inhibitory activity for this step was approximately 30%.

Example 4
Ion Exchange Chromatography

Hookworm lysate fractionated by molecular sieve chromatography on Superdex 75 (Pharmacia) was mixed with an equal volume of Mono Q buffer [0.02 M Tris-HCl, pH 7.5] and loaded on to a 0.5×5.0 cm Mono Q anion exchange column (Pharmacia) equilibrated with Mono Q buffer at a flow rate of 1 mL/minute (306 cm/hour). The column was then developed with a linear gradient of 0–0.5 M NaCl in column buffer at 0.5 mL/minute (153 cm/hour). Neutrophil inhibitory activity consistently eluted at 0.4 M NaCl. The overall yield of inhibitory activity for this isolation was about 2–5%.

Example 5
SDS-Polyacrylamide Gel Electrophoresis

The protein composition of hookworm lysate and fractionated lysate was analyzed by sodium dodecyl sulfate polyacrylamide gel electrophoresis (SDS-PAGE) (LaemmLi, U.K. 1970, Nature 227, 680) after silver staining (Morrisey, J. H. 1981, Anal. Biochem. 117, 307). Samples were mixed with an equal volume of 20% glycerol, 5% SDS, and 0.125 M Tris-HCl, pH 6.8 and placed in a boiling water bath for 5 minutes. Samples were subsequently applied onto 10% SDS polyacrylamide slab gels of 0.75 mm thickness and subjected to electrophoresis for 2 hours at constant voltage (125 V).

Figure 5:
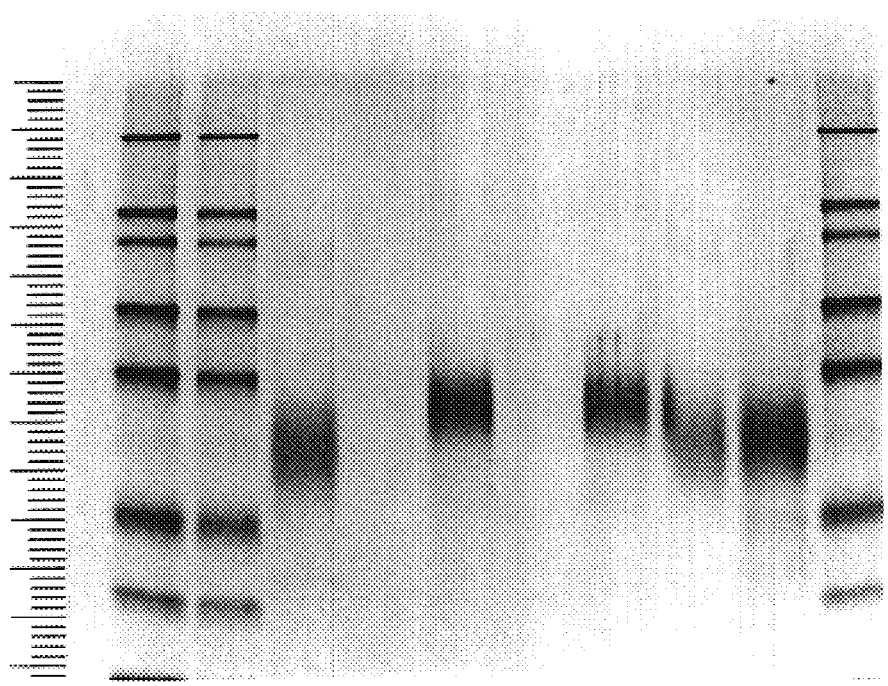
FIG. 5 depicts a gel pattern run using SDS-gel electrophoresis of the HPLC isolate and certain molecular weight standards.

FIG. 5 depicts the results of SDS polyacrylamide gel electrophoresis. Samples were applied to a 10% polyacrylamide slab gel (Novex, La Jolla, Calif.). Lanes 1–10, left to right, are (1) molecular weight standards; (2) molecular weight standards; (3) HPLC pool of HA fractions #37–41, non-reduced; (4) blank; (5) HPLC pool of HA fractions #37–41, reduced; (6) blank, (7) HPLC pool of HA fractions #37–41, reduced, (8) HPLC pool of HA fractions #37–41, non-reduced; (9) HPLC pool of HA trailing fractions #42–48, non-reduced, (10) molecular weight standards. The molecular weight standards used were: myosin, 200,000 (rabbit muscle); beta-galactosidase, 116,300 (E. coli); phosphorylase b, 97,400 (rabbit muscle); bovine serum albumin, 66,300; glutamic dehydrogenase, 55,400, (bovine liver); carbonic anhydrase, 31,000, (bovine erythrocyte); trypsin inhibitor, 21,500, (soybean).

Following the last step of the isolation procedure (reverse phase HPLC) only a single diffuse band with an apparent molecular weight ranging from 33,000 to 47,000 was observed upon SDS-PAGE (see FIG. 5). When 50 mM dithiothreitol was added to the sample prior to boiling, the diffuse band migrated with an estimated molecular weight of 43,000 to 54,000.

Example 6
Laser-Desorption Time-of-Flight Mass Spectrometry of the Isolated Neutrophil Inhibitory Factor The estimated mass for the NIF isolated as described in Example 2(E) was determined using laser-desorption time-of-flight mass spectrometry.

A 1 µl aliquot of the sample was diluted with an equal volume of a saturated solution of 3,5-dimethozy-4-hydroxycinnamic acid dissolved in 30% aqueous $CH_3CN$, 0.1% TFA. The diluted sample was spotted onto a copper sample stage and allowed to air dry. Mass analysis was performed using a Shimadzu LAMS-50KS laser desorption time of flight mass spectrometer (Shimadzu Corp., Kyoto, Japan). Ionization of the sample was accomplished by focusing 500 laser pulses (355 nm, pulse width<5 nsec) from a Nd-YAG laser (Spectra-Physics, Inc., Mt. View, Calif.) onto the sample stage. The resulting ions were accelerated into the mass spectrometer by a 5 kV potential. Calibration of the instrument was accomplished using standard proteins of known mass.

Figure 6:
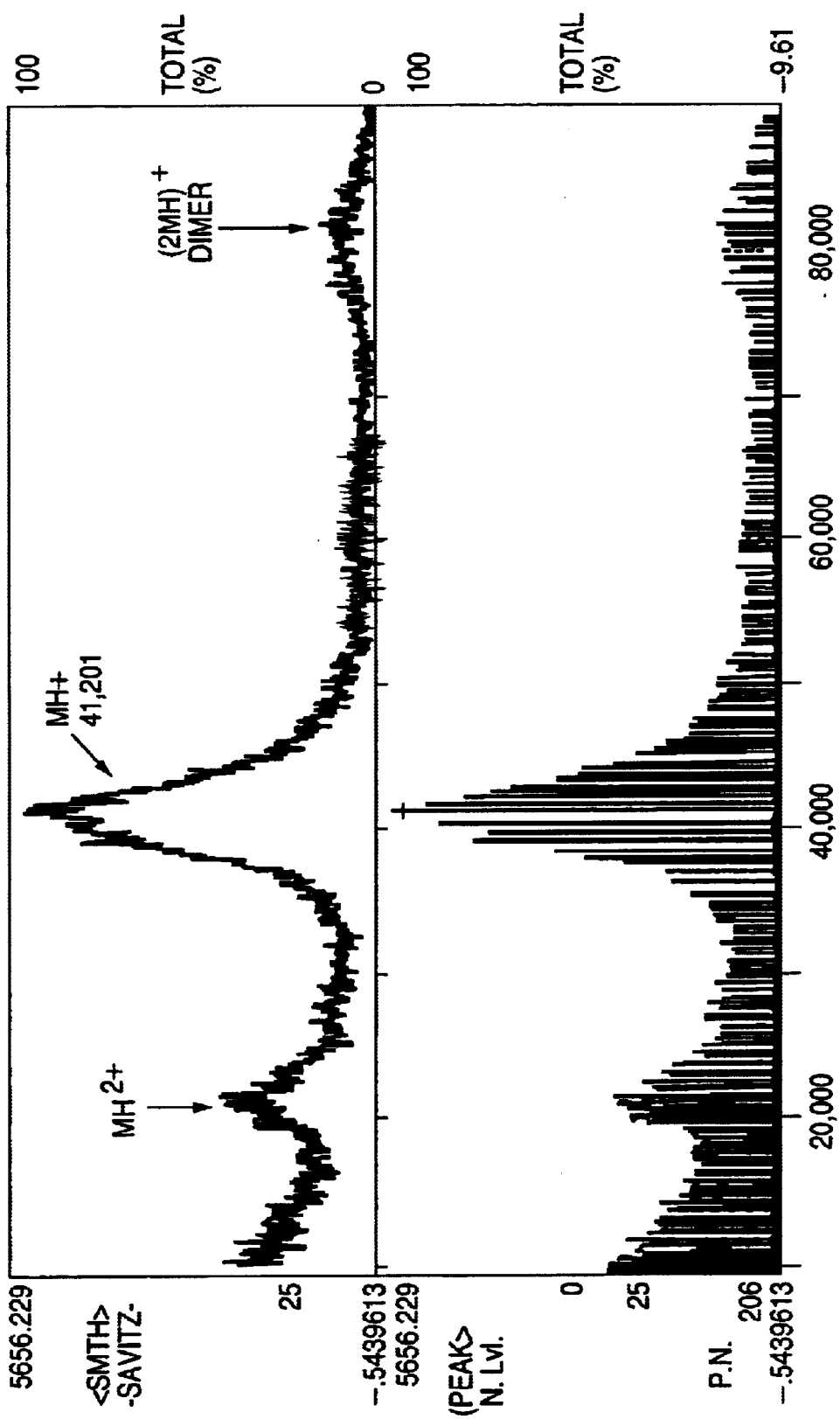
FIG. 6 depicts laser-desorption time-of-flight mass spectrometry of the purified Neutrophil Inhibitory Factor of the present invention.

FIG. 6 depicts the results of laser-desorption time-of-flight mass spectrometry of the isolated neutrophil adhesion inhibitor. Five picomoles of the purified neutrophil function inhibitor was analyzed with a laser desorption time-of-flight mass spectrometer. The estimated mass was determined as 41,200. A small fraction of the sample had a mass of 82,400; this was interpreted to be a dimer.

Example 7
Neutrophil Inhibitory Factor is a Glycoprotein

Purified NIF (prepared according to Example 2(E)) (~2 µg) was electrophoresed in a 10% SDS polyacrylamide gel and the resolved protein transferred by Western blotting (Towbin, et al., 1979 Proc. Natl. Acad. Sci. (USA) 76, 4350–4354) to a Zeta-Probes® nitrocellulose membrane (BioRad, Emeryville, Calif.). The membrane was treated as described in the instructions to the GlycoTrack™ Kit (Oxford GlycoSystems, Rosedale, N.Y.) to oxidize carbohydrates to aldehydes which were then reacted with biotin-hydrazide leading to incorporation of biotin into any carbohydrate present. Biotinylated carbohydrate was subsequently detected by reaction with a streptavidin-alkaline phosphatase conjugate. Visualization was achieved using a substrate which reacts with alkaline phosphatase bound to glycoproteins on the membrane, forming a colored precipitate. Neutrophil Inhibitory Factor was stained using this method, demonstrating that it contained carbohydrate and is therefore a glycoprotein.

Example 8
Organic Extraction of the Hookworm Lysate

One milliliter of hookworm homogenate known to have inhibitory activity in the neutrophil-plastic adhesion assay was extracted by vortexing 1 minute with 1 mL of a chloroform/methanol (2:1) mixture in a 15 mL glass Corex test tube. The organic layer was removed and dried under a stream of nitrogen gas. Residual lipids were resuspended in 0.5 mL HSA assay buffer by sonication for 2 minutes (Branson Model 1200, Danbury, Conn.). Resuspended lipids had no inhibitory activity in the neutrophil-plastic adhesion assay when tested at a final dilution of 1:2.

Example 9
Production and Determination of the Amino Acid Sequence of Peptide Fragments of Neutrophil Inhibitory Factor Samples of NIF were obtained as described in Example 2. Two separate volumes, each containing approximately 10 µg NIF, were first degassed on a Speed Vac until the samples were frozen and then lyophilized. The dried samples were resuspended in 50 mM N-ethylmorpholine, pH 8.5, and digested with either endoproteinase AspN (Boehringer Mannheim, Indianapolis, Ind.), Lys C (Boehringer Mannheim, Indianapolis, Ind.) or trypsin (Worthington, Freehold, N.J.) at a substrate to enzyme ratio of 25:1. Incubation was at ambient temperature for 24 hours and a small amount of isopropanol was added to the digestion mix to prevent microbial contamination. At the end of the digestion, the samples were degassed on a Speed Vac and dried by lyophilizing. The digestion mixtures were resuspended in 6M guanidine/HCl for fractionation of peptides by reversed phase HPLC (RP HPLC). Peptides were isolated by RP HPLC on a ToyoSoda 120T C18 (4.5×250 mm) column using an LKB HPLC system with Kratos (ABI, Foster City, Calif.) detectors. The column was developed with a linear gradient of acetonitrile in 0.1% trifluoroacetic acid (TFA). The gradient was from 5 to 54% acetonitrile over 120 minutes at a flow rate of 0.5 mL/minute. Peptide peaks monitored by $A_{206}$ and $A_{280}$, were collected using an LKB SuperRac with calibrated peak detection. The collected fractions were neutralized with ammonium carbonate, 20 μg SDS was added, and the fractions dried under $N_2$ before sequencing. Peptides were sequenced on a 470A/120A/900A gas phase sequencer (ABI, Foster City, Calif.). Residue identification was performed manually by analysis of the HPLC chromatograms and quantification of the PTH residues was performed by online analysis on the 900A computer. Cysteine residues were not detected in this analysis because the protein had not been alkylated. In experiments in which the protein was digested with trypsin, the protein was alkylated with vinylpyridine before fragmentation, thereby permitting the detection of cysteine in the tryptic fragments. Aspartic acid and tryptophan residues were identified but not quantitated because background peaks overlapped the PTH residues in the HPLC elution. The initial yields ranged from 1 pmole to 10 pmole and the repetitive yield was usually between 92 and 95%. FIG. 7 depicts the amino acid sequences that were obtained from the proteolytic fragments [SEQ. ID. NOS. 13 to 31]. In FIG. 7, positions enclosed in parentheses were not determined with absolute certainty. Abbreviations for amino acids beginning with a capital letter were observed in higher yield and are preferred in these cases. The abbreviation Xxx indicates an undetermined amino acid at that position, since no specific amino acid was identified during Edman degradation of the peptide. See Scarborough et al. *J. Biol. Chem* 266:9359, 1991.; Perin et al.,*J. Biol. Chem.* 266:3877, 1991.

Example 10

Cloning and Sequencing of Neutrophil Inhibitory Factor from Hookworm

NIF was cloned from a canine hookworm cDNA library, constructed as follows: Total RNA was isolated from whole hookworms by guanidium thiocyanate extraction (McDonald et al., Meth. Enzymol. 152:219 (1987)). Poly (A)+ RNA was purified from 500 μg of total hookworm RNA using oligo d(T) cellulose affinity. chromatography (PolyA Quik; Stratagene, La Jolla, Calif.). Double stranded cDNA was synthesized from poly(A)+ RNA using random hexamer primers and avian myoblastosis virus (AMV) reverse transcriptase (Amersham, Arlington Hills, Ill.). cDNA fragments larger than 1 kilobase pairs were purified on a 6% polyacrylamide gel and ligated to EcoRI linkers (Stratagene) using standard procedures. Linkered cDNA was ligated into lambda gt10 (Stratagene, La Jolla, Calif.) and packaged using Gigapack Gold II (Stratagene).

Double stranded cDNA probes for hookworm NIF were generated by polymerase chain reaction from hookworm RNA using primers derived from NIF peptide sequences. The sequences obtained for two NIF peptides (see FIG. 7), T-20 (Leu-Ala-Ile-Leu-Gly-Trp-Ala-Arg) [SEQ. ID. NO. 14] and T-22-10 (Leu-Phe-Asp-Arg-Phe-Pro-Glu-Lys) [SEQ. ID. NO. 15], were used to design primers 30.2 and 43.3.RC, respectively. The sequences of 30.2 and 43.3.RC were 5'-CTCGAATTCT(GATC)GC(ATC)AT(ATC)(CT)T (GATC)-GG(ATC)TGGGC-3' [SEQ. ID. NO. 6] and 5'-CTCGAATTCTT(TC)TCTGG(GA)AA-(GA)CG(GA) TC(GA)AA-3' [SEQ. ID. NO. 7], respectively. Bracketed positions represent redundant nucleotides. Single stranded cDNA was synthesized by priming 1 μg of hookworm poly(A)+ RNA (preparation described above) with random hexanucleotides and extending with AMV reverse transcriptase (Amersham, Arlington Hills, Ill.). One twentieth of the reaction product was amplified using the PCR GeneAmp kit (Perkin Elmer, Norwalk, Conn.), with 400 pmol of each of 30.1 and 43.RC (manufactured by Research Genetics, Huntsville, Ala.), on a Perkin Elmer DNA Thermal Cycler. PCR conditions were: cycles 1–2, denaturation at 94° C. for 2 minutes, annealing at 58° C. for 2 minutes and elongation at 72° C. for 2 minutes; cycles 3–42, denaturation at 94° C. for 45 seconds, annealing at 58° C. for 45 seconds and elongation at 72° C. for 2 minutes. The ~430 base pair amplification product, referred to as the 30.2/43.3.RC fragment, was separated from reaction contaminants by electroelution from a 6% polyacrylamide gel (Novex, San Diego, Calif.). The 30.2/43.3.RC fragment was labelled with [a-$^{32}$P]-dCTP (Amersham) using random primer labelling (Stratagene, La Jolla, Calif.); labelled DNA was separated from unincorporated nucleotides using a ChromaSpin-10 column (Clontech, Palo Alto, Calif.).

Prehybridization and hybridization conditions were 6×SSC (SSC: 150 mM NaCl, 15 mM trisodium citrate), 0.02 M sodium phosphate pH 6.5, 5×Denhardt's solution, 0.5% (w/v) SDS, 0.01 M EDTA, 100 μg/mL sheared, denatured salmon sperm DNA, 0.23% dextran sulfate, 50% formamide. Prehybridization and hybridization were at 42° C., and the filters were washed for 20 minutes with 0.2×SSC at 60° C. after two prewashes with 2×SSC for 15 minutes. The filters were exposed overnight to X-ray film with two intensifying screens at –70° C.

Approximately 300,000 recombinant phage of the random primed hookworm library (unamplified) were screened with the 30.2/43.3.RC NIF PCR fragment. About 120 recombinant phage hybridized to this probe, of which seven were isolated for nucleotide sequencing analysis. Double stranded sequencing was effected by subcloning the EcoRI cDNA fragments contained in these phage isolates into pBluescript II vector (Stratagene, La Jolla, Calif.). DNA was sequenced using the Sequenase version 2.0 kit (U.S. Biochemical, Cleveland, Ohio) and synthetic oligonucleotide primers.

The NIF phage isolates contained DNA that encoded polypeptides that bore striking resemblance to the amino acid sequences obtained for purified NIF (see FIG. 7). FIG. 8 depicts the nucleotide sequence of the coding region of Neutrophil Inhibitory Factor cDNA (clone 1FL) (SEQ. ID. NO. 32) and its predicted amino acid sequence [SEQ. ID. NO. 33]. A single isolate, NIF-1FL, encoded an open reading frame of 825 nt, initiating with a methionine and terminating with a TGA stop codon (FIG. 8). The NIF polypeptide encoded by NIF-1FL is 274 amino acid residues with a calculated molecular weight of 30,680 daltons. FIG. 9 depicts the alignment of the predicted amino acid sequences of several Neutrophil Inhibitory Factor isoform clones. Each line of sequence represents the corresponding sequence segments of the various clones isolated. Each segment is identified by its clone designation (e.g., 1FL (SEQ. ID. NO. 33), 3P (SEQ. ID. NO. 34), 2FL (SEQ. ID. NO. 35), 3FL (SEQ. ID. NO. 36), 4FL (SEQ. ID. NO. 37), 6FL (SEQ. ID. NO. 38) and 1P (SEQ. ID. NO. 39). The complete amino acid sequence of clone 1FL is listed in standard three-letter amino acid code at the top of each sequence segment. Clones having the same amino acid in a given position as clone 1FL are denoted by ".". Amino acid substitutions are indicated by the appropriate three-letter code. "- - -" indicates a space inserted to maintain alignment of the sequences. The carboxy termini of the 1FL and 1P sequences are denoted by an asterisk. The other six NIF phage isolates encoded partial NIF polypeptides; that is they did not contain either an N-terminal methionine residue or a C-terminal stop codon, as compared to the NIF-1FL polypeptide (SEQ. ID. NO. 33)(FIG. 9). These partial NIF isolates comprised six predicted NIF isoforms that were significantly similar to, but not identical to the prototypical NIF-1FL polypeptide.

Example 11
Expression of Functional Recombinant Neutrophil Inhibitory Factor by Mammalian Cells
(A) Expression The segment of DNA encoding the NIF-1FL isoform was amplified from the original |gt10 isolate DNA using unique primers for the 5'- and 3'-ends of the coding region.

The 5'-primer was composed of a restriction endonuclease site (EcoR1), a consensus ribosome binding site (Kozak, M., Cell 44: 283 (1986)), the ATG initiation codon of NIF and the succeeding 6 codons of the gene. The 3'-primer was composed of a unique nucleotide sequence to the 3'-side of the TGA termination codon of NIF and a restriction endonuclease site (EcoR1). The nucleotide sequences of the 5'- and 3'-primers were 5'-ACC-GAA-TTC-ACC-ATG-GAG-GCC-TAT-CTT-GTG-GTC [SEQ. ID. NO. 8] and 5'-CTG-GAA-TTC-TCG-CTT-ACG-TTG-CCT-TGG-C [SEQ. ID. NO. 9], respectively.

Five microliters of the lambda plaque suspended in 1 mL dilution buffer were used as template DNA. Amplification was accomplished using the PCR GeneAmp kit (Perkin Elmer, Norwalk, Conn.), with 400 pmol of each of the 5'- and 3'-primers (manufactured by Research Genetics), on a Perkin Elmer DNA Thermal Cycler. The PCR conditions were: cycle 1, denaturation at 97° C. for 1 minute, primer annealing for 1 minute at 37° C., ramp from 37° C. to 72° C. in 2 minutes, and amplification for 2 minutes at 72° C.; cycles 3 and 4, denaturation at 94° C. for 1 minute, primer annealing for 1 minute at 37° C., ramp from 37° C. to 72° C. in 2 minutes, and amplification for 2 minutes at 72° C.; cycles 5 through 34, denaturation at 94° C. for 1 minute, primer annealing for 1 minute at 45° C., and amplification for 2 minutes at 72° C.

The amplification product (887 bp) was separated from reaction contaminants using a ChromaSpin 400 column (Clontech Laboratories, Inc. Palo Alto, Calif.). The ends of the amplification product were trimmed with the restriction endonuclease EcoR1 and the resulting fragment of DNA (875 bp) ligated into EcOR1-digested plasmid pSG5 (Stratagene, La Jolla, Calif.) using standard techniques. The resulting ligation mixture was used to transform SURE™ competent cells (Stratagene, La Jolla, Calif.).

An isolate containing the 875 bp insert in the proper orientation (5'-end of the coding region proximal to the pSG5 SV40 promoter) was grown in 250 mL Circle Grow™ (Biolo, San Diego, Calif.) with 50 mg/mL ampicillin and plasmid DNA was prepared using a Magic Maxi Prep™ DNA purification system (Promega, Madison, Wis.). Ten micrograms of purified plasmid DNA was transferred into $3.5 \times 10^6$ COS7 cells (ATCC No. CRL 1651) by electroporation (0.4 cm electroporation cell, 325 V, 250 F, infinite resistance, 0.5 mL cells at $7 \times 10^6$/mL in Hepes buffered saline, pH 7.0, 4° C.). After electroporation the cells were allowed to stand on ice for 2 to 3 minutes before dilution with 14 mL warm DMEM:RPMI 1640 (1 to 1 ratio) supplemented with 10% fetal bovine serum prewarmed to 37° C. The cells were placed in 100 mm cell culture dishes and incubated at 37° C. with 8% $CO_2$. Cell culture supernatant fluid was removed at 1, 2 and 3 days after plating and assayed for NIF activity.

(B) Detection and Quantitation of Neutrophil Inhibitory Factor Activity in Cell Culture Medium 15 mL of cell culture fluid was harvested from electroporated COS7 cells (pSG5/NIF1FLCR1). When assayed directly using the neutrophil-plastic adhesion assay (Example 1(C)), this fluid exhibited neutrophil inhibitory activity to dilutions as great as 1:8. An $IC_{50}$ at approximately 1:14 was determined using the hydrogen peroxide release assay (Example 1(E)). No activity was observed using cell culture fluid harvested from COS7 cells electroporated with a control expression plasmid (pCAT; Promega, Madison, Wis.).

(C) Fractionation of Neutrophil Inhibitory Factor Activity by Chromatography on Immobilized Concanavalin A Five mL of COS7(pSG5/NIF1FLCR1) cell culture fluid was mixed with an equal volume 0.02 M bis Tris-propane-HCl, pH 7.3, 1 M NaCl, 0.001 M $CaCl_2$, 0.001 M $MnSO_4$ and loaded onto a one mL column of Concanavalin A Sepharose (Pharmacia, Piscataway, N.J.) equilibrated with the same buffer. The sample was cycled through the column in a closed loop for 1 hour at 2 mL/minute at 20° C. The column was subsequently washed with 5 mL of 0.02 M bis Tris-propane-HCl, pH 7.3, 1 M NaCl, 0.001 M $CaCl_2$, 0.001 M $MnSO_4$. The buffer resident in the column was displaced with buffer containing 0.5 M methyl-alpha-mannopyranoside and flow stopped for 15 minutes. Flow was restarted at 1 mL/minute and approximately 11 mL of sugar-containing eluate collected. The eluate was dialyzed 18 hours against 1 liter 10 mM potassium phosphate, pH 7.35, 150 mM NaCl at 4° C. and concentrated to 1.1 mL using an Amicon centrifugal concentrator equipped with a 10,000 molecular weight cut-off membrane (CentriPrep 10, Amicon, Beverly, Mass.). When assayed by the neutrophil-plastic adhesion assay (Example 1(C)), this sample exhibited substantial activity at a dilution of 1:16, indicating that a significant portion of the neutrophil function inhibitor activity present in the cell culture fluid binds to immobilized Concanavalin A. This behavior is identical to that observed for crude extracts of Ancylostoma caninum (Example 2(B)) and is consistent with the inhibition resulting from the synthesis and secretion from transfected mammalian COS7 cells of a glycoprotein that acts as an inhibitor of neutrophil function.

As a control, 5 mL of COS7 cell culture medium from cells electroporated in the absence of DNA was chromatographed on Concanavalin A Sepharose in the same manner as described above. No activity was observed after Concanavalin A-Sepharose chromatography using the neutrophil-plastic adhesion assay. (Example 1(C)).

(D) Fractionation of Neutrophil Inhibitory Factor Activity by Anion Exchange Chromatography using POROS II Q/M.

Five mL of COS7(pSG5/NIF1FLCR1) cell culture fluid was dialyzed 18 hours against one liter of 10 mM bis Tris-propane-HCl, pH 7.0 at 4° C. and loaded at 3 mL/minute onto a 0.46×10 cm column of Poros II Q/M (PerSeptive Biosystems, Inc., League City, Tex.) equilibrated with the same buffer. The column was washed with one column volume of equilibration buffer and developed with a linear gradient of sodium chloride from 0 to 0.5 M over 14.4 column volumes collecting 2 mL fractions. Significant activity in the neutrophil-plastic adhesion assay (Example 1(C)) was detected in fractions 17 and 18, corresponding to about 0.45 M NaCl. When fractions were concentrated twenty-fold using centrifugal concentrators equipped with a 10,000 MWCO membrane (Amicon Micro-Con 10, Beverly, Mass.), substantial activity was found in fractions 16–19.

Neutrophil inhibitory factor present in extracts from Ancylostoma caninum elutes likewise from an anion exchange column (Mono Q, Pharmacia, Piscataway N.J.) at 0.4 M NaCl (Example 4).

Example 12

Expression of Functional Recombinant Neutrophil Inhibitory Factor in Pichia pastoris (A) Description of the Pichia shuttle/expression vector The Pichia strain GTS115 (his4)(Stroman, D. W. et al., U.S. Pat. No. 4,855,231 (Aug. 8, 1989)) and the E. coli-Pichia shuttle vectors pHILS1 and pHILD5 referred to hereafter are part of the Pichia yeast expression system licensed from the Phillips Petroleum Company (Bartlesville, Okl.). All of the Pichia manipulations were performed essentially as described for Saccharomyces cerevesiae in Gene Expression Technology, pp.231–471, Academic Press, New York, (D. V. Goeddel, edit. 1991) and in Stroman, D. W. et al., U.S. Pat. No. 4,855,231 (Aug. 8, 1989).

The pHIL7SP8 vector used to direct expression of NIF in P. pastoris was assembled from pHILS1 and pHILD5 and from synthetically generated fragments. The pHIL7SP8 plasmid contained the following elements cloned onto pBR322 sequences:

1) 5' AOX1, about 1000 bp segment of the P. pastoris alcohol oxidase 5' untranslated and promoter sequences (see Stroman, D. W. et al., U.S. Pat. No. 4,855,231 (Aug. 8, 1989) the disclosure of which is incorporated herein by reference).

2) the PHO1 P. pastoris secretion signal.

3) a 19-amino acid synthetic pro-sequence fused to the PHO1 signal. This pro-sequence represents one of the two 19-aa pro-sequences designed by Clements et al.,(1991. Gene, 106:267–272) on the basis of the yeast alpha-factor leader sequence.

4) a synthetic multi-cloning site 5) 3' AOX1, about 256 bp segment of the aox1 terminating sequence (see Stroman, D. W. et al., U.S. Pat. No. 4,855,231 (Aug. 8, 1989) the disclosure of which is incorporated herein by reference).

6) P. pastoris histidinol dehydrogenase gene, his4, contained on a 2.4 kb fragment to complement the defective his4 gene in the host GTS115 (see Stroman, D. W. et al., U.S. Pat. No. 4,855,231 (Aug. 8, 1989) the disclosure of which is incorporated herein by reference).

7) Region of 3' AOX1 untranslated DNA sequence, which together with the 5' AOX1 region is necessary for site-directed integration (see Stroman, D. W. et al., U.S. Pat. No. 4,855,231 (Aug. 8, 1989) the disclosure of which is incorporated herein by reference).

(B) Construction of pHIL7SP-NIc1/pHIL7SP-NIc10 and Expression in Pichia

The segment of DNA encoding NIF was PCR-amplified from a sub-clone of NIF-1FL in BluescriptII (Stratagene, La Jolla, Calif.) using unique primers for the 5'- and 3'-ends of the coding region.

The 5'-primer contained no restriction endonuclease sites and corresponded to the region beginning at the 5'-end of proteolytically processed NIF and the succeeding 7 codons. The codon for the first residue of the mature NIF (SEQ. ID. NO. 41) was altered from AAT to AAC (both codons translate to asparagine). The 3'-primer was composed of 8 codons at the 3' end of the coding region, a TAA stop replacing the TGA stop of the natural gene, and three unique restriction endonuclease sites (HindIII, SpeI, and BqlII). The sequences of the 5'- and 3'-primers used were 5'-AAC-GAA-CAC-AAC-CTG-AGG-TGC-CCG [SEQ. ID. NO. 10] and 5'-CCT-CCT-CCT-AGA-TCT-AAG-CTT-ACT-AGT-TTA-TAA-CTC-TCG-GAA-TCG-ATA-AAA-CTC [SEQ. ID. NO. 11], respectively.

Amplification was accomplished using 100 pmol of each primer, 2 units of Vent polymerase in 1X Vent buffer (New England Biolabs, Beverly, Mass.), and 0.2 mM of each of dATP, dCTP, dGTP, and dTTP. One hundred nanograms of BluescriptII-containing NIF-1FL [SEQ. ID. NO. 40] were used as template DNA. The PCR conditions were the same for all ten cycles: denaturation at 95° C. for 1 minute, primer annealing at 60° C. for 1 minute, and amplification for 1.5 minutes at 72° C. The amplification product was purified as described above and digested with BglII.

The amplification product was then ligated into StuI-BglII cleaved pHIL7SP8 using standard methods. The ligation mixture was used to transform E.coli WK6, and ampicillin resistant clones were obtained on ampicillin plates. Based on restriction and DNA sequence analysis, correct insert sequences in two of the resulting plasmid clones, pHIL7SP-NIlc1 and pHIL7SP-NI1c10, were selected to transform the P.pastoris yeast strain GTS115 (his4). These vectors were digested with either Not1 (targeting integration to the expression cassette in the AOX1 region) or Sal1 (targeting integration to the HIS4 locus). The 4 restricted DNA preparations were introduced individually into Pichia by electroporation, essentially as described by Becker, D. and Guarente, L., Methods in Enzymology, vol. 194, pp. 182–189 (1991). Briefly, the cells were grown in YEPD medium at 30° C. to an $OD_{600}$ of 1.3 to 1.5. The cells were pelleted at 4° C. (1500×g for 5 min) and resuspended in 500 mL ice cold sterile distilled water. The cells were pelleted as above and resuspended in 250 mL ice cold distilled water. After the cells were pelleted again, they were resuspended in 20 mL ice cold 1 M sorbitol. After a final pelleting the cells were resuspended in 1 mL ice cold 1 M sorbitol. Forty μL cells in 1 M sorbitol were mixed with 5 μL of linearized DNA and the mixture transferred to an ice cold 0.2 cm gap electroporation cuvette. After 5 minutes on ice, the cells were pulsed at 50 μF, 1.5 kV/cm, and 200 resistance. One mL of ice cold 1 M sorbitol was added to the cuvettes and 100 to 500 ul of the cell suspension were spread on minimal dextrose plates. The plates were incubated at 30° C. until colonies appeared. The transformation mix was plated on minimal dextrose (MD) medium to select for His+ transformants. Subsequent selection for NIF expression was performed in shake flask cultures in minimal medium containing methanol as described in Stroman, D. W. et al., U.S. Pat. No. 4,855,231 (Aug. 8, 1989)

(C) Detection and Quantitation of Neutrophil Inhibitory Activity in Cell Medium

Pichia cell supernatant (pHIL7SP-N1c10) was obtained by centrifugation for 15 minutes at $1,800 \times g_{max}$ from cells 48 hours following methanol induction and filtered through a 0.22 μm cellulose acetate membrane. The filtered cell supernatant solution was concentrated about 3-fold using centrifugal concentrators equipped with a 10,000 MWCO membrane (Amicon MicroCon 10, Beverly, Mass.) and desalted by gel filtration using a 1×10 cm column of G-25 Sephadex Superfine (Pharmacia, Piscataway, N.J.). Using the neutrophil-plastic adhesion assay (Example 1(C)), the desalted supernatant solution (diluted 2× by gel filtration)

exhibited neutrophil inhibitory activity to dilutions as great as 1:640. No activity was observed using cell supernatant solution similarly harvested and treated from Pichia cells expressing a recombinant anti-thrombotic protein devoid of neutrophil inhibitory activity.

(D) Purification of Neutrophil Inhibitory Factor from Pichia

Following methanol induction for 48 hours, 75 mL of Pichia cell supernatant (pHIL7SP-N1c10) 48 hours following methanol induction was obtained by centrifugation for 15 minutes at $1,800 \times g_{max}$ and filtered through a 0.22 μm cellulose acetate membrane. This was concentrated using an Amicon stirred UF cell equipped with a 10,000 molecular weight cut-off membrane (YM10) and then diluted with water (about 10-fold). This diafiltration process was repeated until the conductivity was reduced from 45 mS to 1 mS. The final volume of the concentrate was 25 mL.

This concentrate was dialyzed at 4° C. for 6 hours against one liter of 0.05 M bis Tris-propane-HCl, pH 7.0 to adjust the pH to neutrality, and then against two changes of one liter of 0.001 M potassium phosphate, pH 7.0.

Fifteen mL of the dialyzed cell supernatant was loaded onto a 0.8×15 cm column of ceramic hydroxyapatite (Pentax, 2 μm; American International Chemical, Inc., Natick, Mass.) equilibrated with 0.001 M potassium phosphate, pH 7.0 at a flow rate of 0.4 mL/min (48 cm/hour). The column was washed with one column volume of 0.001 M potassium phosphate, pH 7.0 and then developed with a linear gradient from 0.001 to 0.050 M potassium phosphate over 20 column volumes at a flow rate of 0.35 mL/min. Substantial neutrophil inhibitory activity eluted at approximately 0.02–0.035 M potassium phosphate in much the same fashion as observed for neutrophil inhibitory factor isolated from *Ancylostoma caninum* (Example 2(D)).

Fractions exhibiting substantial neutrophil inhibitory activity (assessed using the neutrophil-plastic adhesion assay (Example 1(C))) were combined and concentrated to about 3 mL using an Amicon centrifugal concentrator equipped with a 10,000 molecular weight cut-off membrane (CentriPrep 10, Amicon, Beverly, Mass.) and applied to a 1×25 cm C4 300 Å reverse phase column (5 μm particle size, Vydac, Hesperia, Calif.) equilibrated with 0.1% trifluoroacetic acid. The column was washed with four column volumes of equilibration buffer and then developed with a linear gradient of acetonitrile from 15 to 40% over 10 column volumes at a flow rate of 5 mL/min. A major complex peak absorbing at 214, 254, and 280 nm eluted at about 36–38% acetonitrile.

Fractions including and bracketing this peak were dried using a centrifugal evaporator to remove solvent and trifluoroacetic acid and rehydrated with 0.065 M potassium phosphate, pH 7.0, 0.08 M NaCl. The rehydrated fractions possessed substantial neutrophil inhibitory activity as judged by the neutrophil-plastic adhesion assay (Example 1(C)) and the hydrogen peroxide release assay (Example 1(E)).

Fractions with substantial activity were combined and sequenced by Edman degradation using a 470A/120A/900A gas phase sequencer (ABI, Foster City, Calif.) (See Example 9) and yielded the following sequence:

Asn-Glu-His-Asn-Leu-Arg-Xxx-Pro-Gln-Xxx-Gly-Thr-Glu-Met-Pro-Gly-Phe-Xxx-Asp-Ser-Ile-Arg-Leu-Gln-Phe-Leu-Ala-Met -His-Asn-Gly-Tyr-Arg-Ser-Lys-Leu-Ala-Leu-Gly-His-Ile-Ser-Ile-Thr-Glu-[SEQ. ID. NO. 12]. "Xxx" refers to an undetermined amino acid at that position, since no specific amino acid was identified during Edman degradation of the peptide.

This sequence matches the predicted N-terminal sequence of native NIF-1FL (SEQ. ID. NO. 41), the NIF isoform used in this construction construct (pHIL7SP-N1c10; see FIG. 8). The first position at which a residue was not detected is predicted to be a cysteine; cysteine residues could not be detected in this analysis because the protein had not been alkylated. The two other positions at which residues were not detected correspond to asparagine residues followed by either a serine or threonine one residue distant. This is a glycosylation consensus sequence [Asn-Xxx-(Ser/Thr)] and the fact that asparagine was not detected strongly suggests that these asparagines are glycosylated. The C4-purified preparation was estimated to have an $IC_{50}$ of about 5–10 nM in the hydrogen peroxide release assay (Example 1(E)).

Example 13

Determination of Specificity of the Neutrophil Inhibitory Factor

To test the specificity of the Neutrophil Inhibitory Factor of the present invention, and to confirm that it did not inhibit neutrophil activation by a general cytotoxic mechanism, the activity of the inhibitor was assessed in a non-neutrophil cell adhesion-based assay, platelet aggregation.

The effects of the hookworm Neutrophil Inhibitory Factor on blood platelet aggregation were examined. Platelet aggregation was performed with human platelet-rich plasma (PRP). PRP was stirred at 37° C. in an aggregometer (Scienco Model 247, Morrison, Col.) and aggregation was initiated by the addition of 10 $\mu$M ADP (Sigma, St. Louis, Mo.). Aggregation was monitored as a change in light transmittance, and is expressed as the initial rate of aggregation. A concentration of Neutrophil Inhibitory Factor of approximately 150 nM, a concentration that completely blocked neutrophil function as assessed by neutrophil-HUVEC and neutrophil-plastic adhesion assays, homotypic neutrophil aggregation and hydrogen peroxide release by neutrophils, had no inhibitory effect on ADP-induced aggregation of human platelets.

Example 14

Mac-1 Integrin is a Primary Receptor for Neutrophil Inhibitory Factor from Hookworm (A) Immunopreciptation of $^{125}$I-Labelled NIF Using Monoclonal Antibodies to Mac-1 in the Presence of Neutrophil Extract NIF purified from *Ancylostoma caninum* was radiolabeled using the following method. Approximately 30 $\mu$g NIF was labeled with 2 mCi $Na^{125}I$ (carrier free; Amersham, Arlington Hills, Ill.) using Enzymobeads (BioRad, Hercules, Calif.) Briefly, to a 1.5 mL eppendorf test tube was added 360 $\mu$L of the Enzymobead suspension together with 180 $\mu$L of a 1% beta-D-glucose solution, NIF and $Na^{125}I$. This mixture was allowed to react at room temperature for 30 minutes. Labeled NIF was separated from unbound $^{125}$I-iodine by desalting on a PD10-DG column (BioRad, Hercules, Calif.) using phosphate buffered saline (0.1 M sodium phosphate pH 7.2, 0.15 M sodium chloride) containing 1% bovine serum albumin as elution buffer. Radioactive fractions containing NIF were pooled. The specific activity of the $^{125}$I-NIF was 13.9 $\mu$Ci/$\mu$g.

Various leukocyte proteins were assessed for ability to capture NIF in immunoprecipitation experiments. Potential cellular receptors for NIF were selected from a detergent extract of leukocytes using specific monoclonal antibodies.

Leukocytes were prepared from human blood using Mono-poly (ICN, Biomedicals Inc., Costa Mesa, Calif.). The leukocyte cell pellet was resuspended in 1 mL resuspension buffer (20 mM Tris pH 7.5, 150 mM NaCl, 1 mM $CaCl_2$) followed by the addition of 1 mL extraction buffer (2% Triton X-100, 20 mM Tris pH 7.5, 150 mM NaCl, 1 mM CaCl$_2$). Cells were incubated on ice 30–60 minutes, vortexing briefly every 10 minutes. Cell debris was pelleted at 5000 g for 5 minutes at 4° C.

Monoclonal antibody-test protein complexes were formed by incubating 10 μg specific monoclonal antibody with 200 μL of leukocyte detergent extract at 4° C. for 4 hours. To this mixture was added 2.5 μL of the $^{125}$I-NIF and these reagents were incubated at 4° C. for 18 hours. Precipitation of the complex was effected by adding this mixture to a 1.5 mL eppendorf test tube containing 50 μL of protein G-sepharose (Pharmacia, Pistacaway N.J.; resuspended in TACTS 20 buffer (0.05% Tween 20, 20 mM Tris pH 8, 120 mM NaCl, 2 mM CaCl$_2$) with 1% bovine serum albumin) and gently agitating at 4° C. for 2 hours.

The protein G-sepharose beads were subsequently washed four times with TACTS 20 buffer. Fifty microliters of Laemmli sample buffer (Laemmli, U. K., 1970, Nature, 227:680–685) containing 5% b-mercaptoethanol was then added to the aspirated beads; this material was incubated at 100° C. for 10 minutes and loaded onto 4–12% gradient SDS-polyacrylamide gels (Novex, San Diego, Calif.) . Gels were dried after running and visualized by exposure to X-Omat film (Kodak, Rochester, N.Y.) in the presence Quanta III screens (Dupont, Wilmington, Del.) at –70° C. Size standards were $^{14}$C-Rainbow markers (Amersham, Arlington Hills, Ill.).

When monoclonal antibodies (MAb) directed to the Mac-1 integrin complex (OKM-1, ATCC# CRL8026; LM-2, ATCC# HB204) were used in these experiments, $^{125}$I-NIF was precipitated as evidenced by a band that migrated with an apparent molecular weight of approximately 41,000 daltons upon autoradiography. Precipitation of $^{125}$I-NIF was dependent on the presence of these antibodies as well as the presence of leukocyte extract. Furthermore, the precipitation of $^{125}$I-NIF was not observed in the presence of a one hundred fold molar excess of cold NIF. $^{125}$I-NIF did not precipitate when MAbs to other leukocyte integrins were used including MAbs directed against the VLA-4 (L25.3; Becton Dickinson, Sunnyvale, Calif.) and p150,95 (SHCL-3; Becton Dickinson, Sunnyvale, Calif.) integrin complexes. A relatively minor amount of $^{125}$I-NIF was observed when a MAb directed against the LFA-1 (TS1/22; ATCC# HB202) integrin complex was used. This was likely due to cross-reactivity of the anti-LFA-1 antibody with the related integrin complex Mac-1. These results demonstrate that Mac-1 is a cell-surface receptor for *Ancylostoma caninum* NIF on leukocytes.

(B) Precipitation of $^{125}$I-Mac-1 Using Biotinylated NIF

As another approach to identify NIF receptors on leukocytes, biotin-labeled NIF was used to precipitate NIF-associating proteins from a detergent extract of surface iodinated leukocytes.

NIF was biotinylated by conjugation to its carbohydrate moieties. Approximately 8 μg of NIF purified from hookworm (*Ancylostoma caninum*) lysates (hydroxyapatite eluate; see Example 2(D)) was oxidized with 50 mM NaIO$_4$ in 1 mL 0.1 M sodium acetate, pH 5.5. After 20 minutes at 4° C. the reaction was terminated with the addition of 100 μL 165 mM glycerol. Oxidized NIF was separated from other reaction products using a Microcon 10 concentrator (Amicon, Beverly, Mass.), and diluted into 100 μL 0.1 M sodium acetate, pH 5.5. Biotinylation was effected by the addition of 400 μL 6.25 mM biotin-LC-hydrazide (Pierce, Skokie, Ill.). The reaction was allowed to proceed for 18 hours at 4° C. Biotinylated NIF was worked up by buffer exchange into phosphate buffered saline (PBS; 0.1 M sodium phosphate, 0.15 M. sodium chloride, pH 7.2), using a Microcon 10 concentrator. To 250 μL of the concentrate was added an equal volume of glycerol, giving a final NIF-biotin concentration of approximately 16 μg/mL. This material was stored at –20° C.

The anti-CD18 integrin complex monoclonal antibodies LM-2 and OKM-1 (anti-Mac-1; ATCC #HB204 and CRL8026, respectively) and TS1/22 (anti-LFA-1; ATCC# HB202) were biotinylated using the protocol described above.

Cell surface iodination of human leukocytes was done using the following procedure. A total leukocyte fraction, prepared from 90 mL of fresh human blood using Mono-Poly density gradient separation (ICN Biomedical, Costa Mesa, Calif.), was suspended in 0.5 mL phosphate buffered saline. To the cell suspension was added 2 mCi Na$^{125}$I (carrier free; Amersham; Arlington Heights, Ill.), 60 μL 0.03% hydrogen peroxide and 100 μL lactoperoxidase at 2 mg/mL (BioRad; Hercules, Calif.). The reaction was allowed to proceed for 30 minutes at room temperature, with gentle agitation every two minutes. The reaction was terminated by the addition of 25 mM KI in PBS, and the cells were washed two times with PBS. The leukocyte cell pellet was resuspended in 1 mL resuspension buffer and leukocyte extract was prepared as described above in Example 14-(A).

Sixty microliters of NIF-biotin (16 μg/mL) was diluted with 40 μL resuspension buffer and incubated with 200 μL $^{125}$I-labeled leukocyte extract at room temperature for 6 hours. Precipitation of NIF-associating proteins from the leukocyte extract was effected by the addition of 100 μL streptavidin-agarose (Pharmacia; Piscataway, N.J.) to this mixture. Test tubes were agitated gently for 18 hours at 4° C. Beads were subsequently washed four times with 500 μL TACTS-20 buffer (0.05% Tween 20, 20 mM Tris pH 8, 120 mM NaCl, 2 mM CaCl$_2$), and associated proteins were solubilized with 50 μL sample buffer (5% β-mercaptoethanol) and analyzed by SDS-PAGE as described in Example 5. Control precipitations were performed in a similar manner with biotinylated monoclonal antibodies to Mac-1 and LFA-1.

Biotinylated NIF precipitated two $^{125}$I-labeled polypeptides that, when separated by 6% SDS-PAGE, had apparent molecular weights of about 170 kDa and about 95 kDa. These polypeptides comigrated on SDS-PAGE in this experiment with the two polypeptides that were precipitated by the anti-Mac-1 monoclonal antibodies LM-2 and OKM-1. This data strongly suggests that Mac-1 is a major receptor for NIF on leukocytes when considered with the results of the previous experiment (Example 14(A)), in which Mac-1 was shown to associate with NIF.

Example 15

Preparation of Native Neutrophil Inhibitory Factor from *Toxocara canis*

(A) Preparation of Toxocara Lysate

Frozen canine worms *Toxocara canis* were obtained from Antibody Systems (Bedford, Tex.) and were stored at –70° C. until homogenized. *Toxocara canis* were homogenized on ice in homogenization buffer [0.02M Tris-HCl pH 7.4, 0.05 M NaCl, 0.001 M MgCl$_2$, 0.001 M CaCl$_2$, 1.0×10$^{-5}$ M E-64 Protease Inhibitor (CAS 66701-25-5), 1.0×10$^{-6}$ M pepstatin A (isovaleryl-Val-Val-4-amino-3-hydroxy-6-methyl-heptanoyl-Ala-4-amino-3-hydroxy-6-methylheptanoic acid, CAS 26305-03-3), 1.0×10$^{-5}$ M chymostatin (CAS 9076-44-2), 2.0×10$^{-5}$M APMSF (amidinophenylmethylsulfonyl fluoride-HCl), 5% (v/v) glycerol] using an Ultra-Tarrax homogenizer (Janke and Kunkel, Stanfen, Germany). The protease inhibitors E64, pepstatin A, chymostatin, and APMSF were obtained from Calbiochem (La Jolla, Calif.).

Approximately 3–6 mL of homogenization buffer was used to homogenize each gram of frozen worm. Twenty-four grams of worms was used in total. Insoluble material was pelleted by two sequential centrifugation steps: 40,000×$g_{max}$ at 4° C. for 25 minutes followed by 105,000×$g_{max}$ at 4° C. for 1 hour. The supernatant solution was clarified by passage through glass wool and a 0.45 μm cellulose acetate filter (CoStar, Cambridge, Mass.).

(B) Concanavalin A Sepharose Chromatography of Toxocara Lysate

Toxocara canis lysate (68 mL) was absorbed to 26 mL of Concanavalin A Sepharose (Pharmacia, Piscataway, N.J.) pre-equilibrated with Con A buffer [0.02 M Tris-HCl, pH 7.4, 1 M NaCl, 0.001 M $CaCl_2$, 0.001 M $MnSO_4$] by recycling it through a 1.6×13 cm column at a flow rate of 4 mL/minute (119 cm/hour) for 2 hours. The column was at room temperature (24° C.) while the reservoir of lysate was maintained on ice throughout the procedure. The column was subsequently washed with 100 mL of Con A buffer. Material that had activity in anti-adhesion assays (see, Section (D) below) was eluted with approximately 3–5 column volumes of Con A buffer containing 0.5 M methyl-alpha-mannopyranoside (CAS 617-04-09) at a flow rate of 1 mL/minute (30 cm/hour). The eluted material was concentrated to 5 mL using an Amicon stirred ultrafiltration vessel equipped with a 10,000 molecular weight cutoff membrane, then diluted to 50 mL with deionized water, and reconcentrated to 2.3 mL using a centrifugal ultrafiltration unit with a 10,000 molecular weight cut-off (Polysciences, Inc., Warrington, Pa.) Material used for molecular sieve chromotography with Superdex columns (1.5 mL) was additionally concentrated to 0.5 mL using centrifugal ultrafiltration units with a 10,000 molecular weight cut-off (Amicon, Inc., Beverly, Mass.).

(C) Molecular Sieve Chromatography Using Superdex 200 HR

Material eluted from immobilized Concanavalin A (see step (B) above) and concentrated by ultrafiltration was loaded on a 1.0 cm×30 cm column of Superdex 200 HR (Pharmacia, Piscataway, N.J.). The column was pre-equilibrated with 0.01 M potassium phosphate, pH 7.35, and 0.15 M NaCl at 24° C. The chromatography was conducted at a flow rate of 0.25 mL/minute. Anti-adhesion activity eluted with an apparent molecular weight of approximately 20,000.

(D) Assay of Neutrophil Inhibitory Activity Isolated from Toxocara canis

Material eluted from Concanavalin A Sepharose with methyl alpha-mannopyranoside was assayed by the neutrophil-HUVEC adhesion assay (see Example 1(B)) and was found to inhibit the adhesion of neutrophils to endothelial cells. Adhesion inhibitory activity was also demonstrated using the neutrophil-plastic adhesion assay. (Example 1(C)).

Material purified by chromatography on both Concanavalin A Sepharose and Superdex 200 HR inhibited neutrophil adhesion in the neutrophil-adhesion assay (see Example 1(C)).

Example 16
In Vivo Characterization of Neutrophil Inhibitory Factor

Neutrophil Inhibitory Factor isolated from canine hookworms was tested in an animal model of acute inflammation. Peritoneal inflammation was induced in 150–250 gram Sprague-Dawley rats by an intraperitoneal injection of nine mL of 2% oyster glycogen in $H_2O$ (see Baron et al., *Journal of Immunological Methods*, 49:305, 1982; McCarron et al., *Methods in Enzymology*, 108:274, 1984; Feldman et al., *Journal of Immunology*, 113:329, 1974; Rodrick et al., *Inflammation*, 6:1, 1982; and Kikkawa et al., *Laboratory Investigation*, 30:76, 1974).

Figure 10:
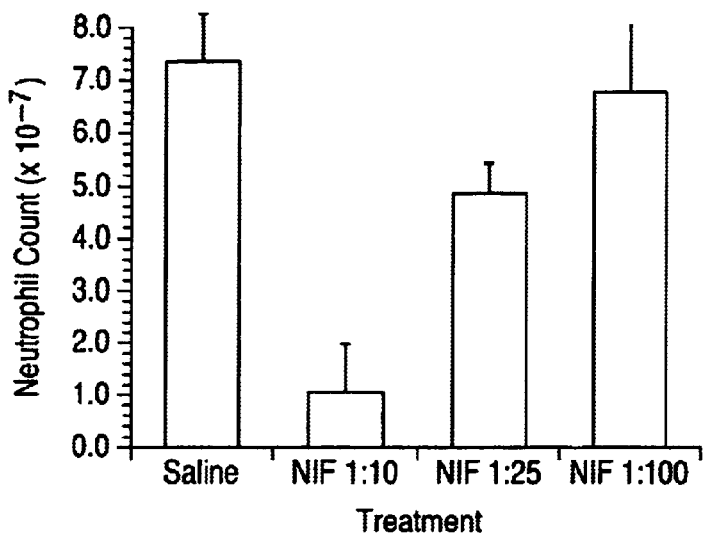
FIG. 10 depicts the anti-inflammatory effect of varied doses of Neutrophil Inhibitory Factor isolated from canine hookworms administered intraperitoneally in an animal model of inflammation.

NIF was prepared as described in Example 2. Lysate from approximately 20,000 hookworms (48.2 g wet weight) was prepared and chromatographed on ConA, Superdex, and hydroxyapatite (HA). The active fractions from two equivalent HA runs were combined to yield 41 mL of HA material. One mL of NIF solution (11 μg) was administered simultaneously with the glycogen by the intraperitoneal route or thirty minutes prior to glycogen administration by the intravenous route. Four hours later the peritoneal exudate was harvested by purging the peritoneal cavity with 30 mL of Hanks Balanced Salt Solution without $Ca^{++}$ or $Mg^{++}$ supplemented with 0.03% EDTA and blood cells were counted on a Celldyn 3000 (Abbott Laboratories, North Chicago, Ill.) automated multiparameter differential cell counting instrument. The major cellular component in the exudate was neutrophils. FIG. 10 depicts the effects of varying doses of Neutrophil Inhibitory Factor isolated from canine hookworms on neutrophil infiltration in peritoneal inflammation in rats induced by interperitoneal infusion with glycogen. Glycogen (9 mL) and Neutrophil Inhibitory Factor (1 mL) were injected simultaneously by intraperitoneal route. FIG. 10 shows the results of six independent experiments. NIF caused a dose dependent inhibition of neutrophil infiltration to the rat peritoneal cavity in response to glycogen.

Figure 11:
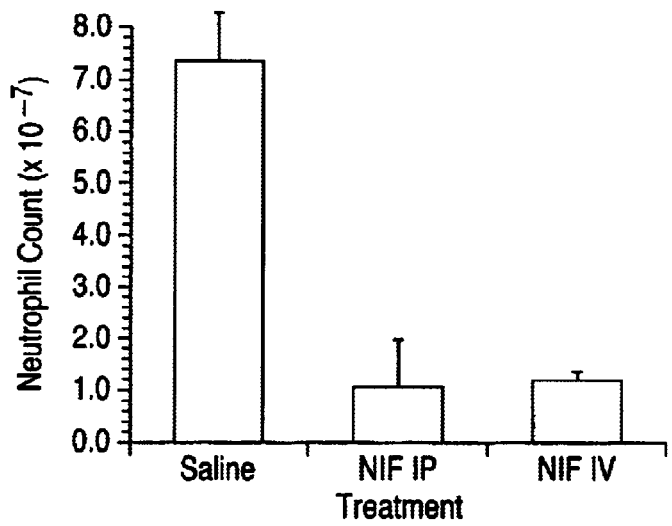
FIG. 11 depicts the anti-inflammatory effect of Neutrophil Inhibitory Factor isolated from canine hookworms administered either intraperitoneally or intravenously in an animal model of inflammation.

A second study was performed to determine if intravenous administration of NIF could prevent glycogen-induced rat peritoneal inflammation. In one set of rats, NIF and glycogen were administered by the intraperitoneal route as previously described. In a second group of rats, 1 μg of NIF was administered intravenously thirty minutes prior to the intraperitoneal infusion of glycogen. A third group of animals received glycogen and NIF treatment was replaced with saline. Four hours later the peritoneal exudate was collected and blood cells were counted. FIG. 11 depicts the effect of Neutrophil Inhibitory Factor isolated from canine hookworms on neutrophil infiltration in peritoneal inflammation in rats induced by intraperitoneal infusion of glycogen. Neutrophil Inhibitory Factor (1 mL) was injected by intraperitoneal route in conjunction with intraperitoneal infusion of glycogen, or by intravenous route thirty minutes prior to infusion of glycogen. FIG. 11 represents a summary of the six independent experiments for the intraperitoneal administration of NIF and the results of the single experiment for the intravenous administration of NIF. These results demonstrate that NIF, when administered by either the intraperitoneal or intravenous route, was effective in the prevention of peritoneal inflammatory response in glycogen-stimulated rats.

Example 17
Inhibition of Neutrophil-Mediated Inflammation In Vivo by Recombinant Neutrophil Inhibitory Factor The in vivo anti-inflammatory properties of recombinant NIF (rNIF) were tested in a rat ear inflammation assay (adapted from Young et al., 1984).

In this assay, inflammation was induced in the rat ear by topical administration of arachidonic acid. Sprague-Dawley rats (250g) were anesthetized with pentobarbital (initial dose of 65 mg/kg intraperitoneal; Anpro Pharmaceutical, Arcadia, Calif.); rats were maintained at a surgical plane of anesthesia for the duration of the experiment (4 hours). A catheter was inserted into the femoral vein of the anesthetized rat. One hundred microliters of recombant NIF (produced in *Pichia pastoris*; see Example 12) [SEQ. ID. NO. 119] at a concentration of 20 mg/mL in PBS was injected via the catheter.

Control rats received 100 µL sterile 0.14 M NaCl. Five minutes after the IV administration of rNIF, arachidonic acid (Sigma, St. Louis, Mo.; diluted 1:1 with acetone to a final concentration of 500 mg/mL) was applied to the right ear in three 10 µL applications each to the inside and the outside of the ear. The right ear thus received a total dose of 30 mg arachidonic acid. The left ear, used as a background control, received a total of 60 µL acetone. Four hours after administration of arachidonic acid the rat was sacrificed with $CO_2$.

Neutrophil infiltration into the arachidonic acid-treated ear tissue was quantitated indirectly by determining myeloperoxidase activity. A tissue sample was obtained from the center of each ear using a 7 mm skin punch (Miltex; Lake Success, N.Y.). The tissue sample was cut into small pieces and added to a 16×100 mm test tube that contained 0.5 mL HTAB buffer (0.5% hexadecyltrimethylammonium bromide in 50 mM sodium phosphate, pH 6.4; HTAB was purchased from Sigma, St. Louis, Mo.). The ear tissue was homogenized for 20 seconds using an Ultra-Turrax (Janke and Kunkel; Staufen, Germany) at high speed. Insoluble matter was removed from the homogenate by centrifugation at 14,000×g for 10 minutes followed by filtration through Nytex gauze. Myeloperoxidase determinations were done in triplicate in 96 well polystyrene plates (Costar; Cambridge, Mass.). Twenty five microliters of HTAB-solubilized ear tissue was added to each well, and to this was added 100 µL of substrate solution. Substrate solution comprised two components: 1) 0.012% $H_2O_2$ in 0.1 M sodium acetate pH 4.5 and 2) 0.3 mg/mL 3,3',5,5'-tetramethylbenzidine in 10% HCl, combined immediately prior to use at a ratio of 0.125:1. After ten minutes the reaction was stopped by the addition of 125 µL 1 M $H_2SO_4$. Samples were quantitated calorimetrically at 450 nm and background was read at 650 nm. A standard curve was generated using human leukocyte myeloperoxidase (Sigma; St. Louis, Mo.).

Figure 12:
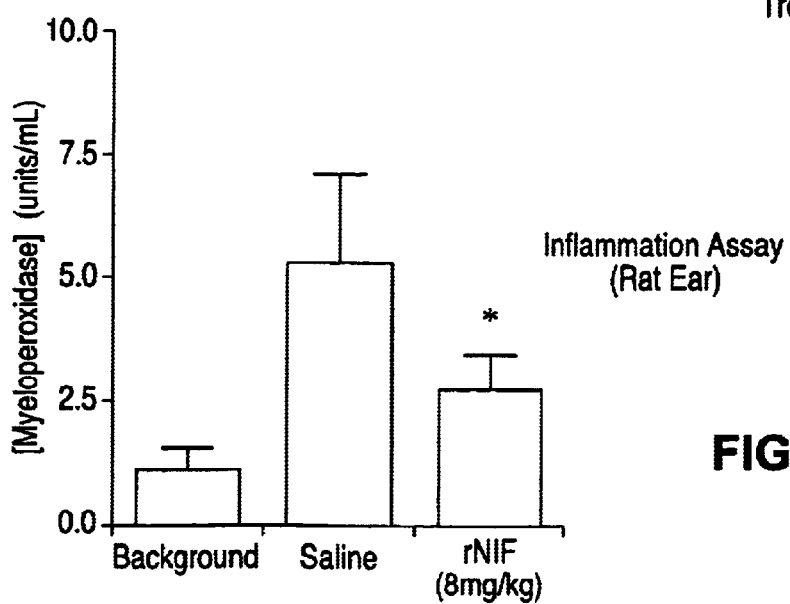
FIG. 12 depicts the anti-inflammatory effect of recombinant Neutrophil Inhibitory Factor produced in *Pichia pastoris* administered in vivo in an animal model of inflammation.

Recombinant NIF had a protective effect on arachidonic acid-induced neutrophil infiltration into ear tissue. FIG. 12 shows that ear tissue from rats that received rNIF had a mean of 1.6 myeloperoxidase units/mL (MU/mL) whereas ears from rats that received saline had a mean of 4.1 MU/mL, when background myeloperoxidase activity is subtracted (n=10 in each group). One myeloperoxidase unit will produce an increase in absorbance at 470 nm of 1.0 per minute at pH 7.0 and 25° C., calculated from the initial rate of reaction using guaiacol as substrate (Desser, R. K., et al., Arch. Biochem, Biophys. 148:452 (1972)). Neutrophil infiltration was thus reduced ~60% in rats that received rNIF (8 mg/kg IV); there is a significant difference at the 95% confidence level between rats that received NIF and rats that received saline (Student's t test). These results are consistent with the demonstration that hookworm-derived NIF prevented neutrophil infiltration into the peritoneal cavity of rats in response to glycogen (see Example 16). These data further provide evidence that rNIF acts as a potent anti-inflammatory agent in vivo.

Example 18
The Use of Neutrophil Inhibitory Factor DNA Sequences to Isolate Neutrophil Inhibitory Factor-Related Proteins NIF cDNA sequences are used as probes to isolate DNA sequences that encode proteins that are functionally and structurally related to NIF.

Genomic DNA or cDNA libraries are formed using standard procedure (for example see Molecular Cloning. A Laboratory Manual. Sambrook, J., Fritsch, E. F., and Maniatis, T. 2nd Ed. Cold Spring Harbor Laboratory Press, CSH, N.Y. 1989). These libraries may be from any animal, fungal, bacterial or viral source, such as *Ancylostoma caninum*, other Ancylostoma species, other helminths and mammals including human placental tissue.

Such libraries are screened for useful clones by nucleic acid hybridization using NIF cDNA sequences isolated from Ancylostoma as probe. For example, NIF cDNA fragments of about 100–2000 base pairs labeled for detection by standard procedure (for example, see Molecular Cloning. A Laboratory Manual. Sambrook, J., Fritsch, E. F., and Maniatis, T. 2nd Ed. Cold Spring Harbor Laboratory Press, CSH, N.Y. 1989) is hybridized with a library from another tissue or another species under conditions of variable stringency. More preferably, however, reduced stringency hybridization conditions are utilized (eg 6×SSC [SSC is 150 mM NaCl, 15 mM trisodium citrate], 0.02 M sodium phosphate pH 6.5, 5×Denhardt's solution, 0.5% (w/v) SDS, 0.01 M EDTA, 100 µg/mL sheared, denatured salmon sperm DNA, 0.23% dextran sulfate, 20–30% formamide at 42° C. for 18 hours). Also, more preferably, reduced stringency conditions are used to wash filters after hybridization (0.5 to 2×SSC at 45–60° C. for 20 minutes after two prewashes with 2×SSC for 15 minutes).

Alternatively, oligonucleotide probes of less than about 100 nucleotides that are based on NIF amino acid sequence are used as probe to screen cDNA libraries. More preferably, primers have the following characteristics: limited degeneracy; adherence to codon usage preferences of the particular species from which the library is constructed and they target sequences that are conserved among the seven Ancylostoma NIF isoforms. Oligonucleotide probes are preferably hybridized under conditions of low stringency (eg 6×SSC, 0.02 M sodium phosphate pH 6.5, 5×Denhardt's solution, 0.5% (w/v) SDS, 0.01 M EDTA, 100 µg/mL sheared, denatured salmon sperm DNA, 0.23% dextran sulfate, 0–20% formamide at 42° C. for 18 hours). Filters are preferably washed under conditions of low stringency (2×SSC at 23–45° C. for 20 minutes after two prewashes with 2×SSC for 15 minutes).

Alternatively, complementary DNA probes are generated to identify NIF-related proteins using polymerase chain reaction. Single stranded oligonucleotide DNA primers of 20–100 nucleotides are derived from the sequence of Ancylostoma NIF. More preferably, primers have the following characteristics: limited degeneracy; adherence to codon usage preferences of the particular species from which the library is constructed and primers that target sequences which are conserved among the seven *Ancylostoma* NIF isoforms.

Single stranded cDNA template is generated using poly $(A)^+$ or total RNA prepared from cells of the tissue or organism to be screened. Approximately 1 µg of RNA is primed with either random hexanucleotides or oligo d(T) and extended with AMV reverse transcriptase (all reagents from Amersham). One twentieth of this reaction product is amplified using an appropriate DNA polymerase (eg Taq polymerase), with 400 pmol each of a sense and antisense primer, on an appropriate thermocycler. A wide variety of polymerase chain reaction conditions are employed, but initial experiments preferably involve relatively low stringency annealing and elongation steps. Preferred conditions are: cycles 1–3, denaturation at 94° C. for 1 minute, annealing at 37° C. for 1 minute and elongation at 72° C. for two minutes. The ramp time between annealing and elongation steps is extended to at least 2 minutes for these cycles; cycles 4–40, denaturation at 94° C. for 1 minute, annealing at 45° C. for 1 minute and elongation at 72° C. for two minutes. In subsequent experiments, annealing temperature is increased until a single product resulted from amplification with each primer pair. Amplification products from individual amplification reactions are used as hybridization probes to screen genomic DNA or cDNA libraries constructed from the tissue or species from which PCR was effected. DNA or cDNA from any recombinant plaque or colony that hybridizes to these amplification products is selected for further analyses.

NIF-related complementary DNAs isolated using the techniques described above are subjected to nucleotide sequence analysis using the procedure of dideoxy sequencing (Sanger et al, 1977, Proc. Natl. Acad. Sci. USA 74:5463–5467). Isolates containing open reading frames (i.e., initiating with a methionine and terminating with a TAA, TGA or TAG stop codon) are inserted into suitable vectors for protein expression in either bacterial, yeast, insect or mammalian cells. Expression systems comprise vectors designed to secrete recombinant protein (i.e., fusion of cDNA isolate open reading frame with a known secretion signal sequence for that cell type) into the culture medium. Vectors lacking a homologous secretion signal sequence are also used for expression. Either conditioned media or cell lysate, depending on the expression system used, is tested for inhibitory activity using one or more of the following criteria for neutrophil activation: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis.

Proteins that are structurally related to NIF and that are inhibitory in one or more of these neutrophil function assays would be considered to belong to the NIF family of related molecules.

Example 19

Expression of Functional Recombinant NIF in *E. coli*

DNA for the NIF-1FL coding region, (SEQ. ID. NO.32) initiating at the codon that corresponds to the N-terminal methionine, is inserted into an *E. coli* expression vector. Examples of such vectors are given in Balbas, P. and Bolivar, F., 1990 (Methods in Enzymology, 185:14–37). The DNA is inserted into the *E. coli* expression vector using methods similar to the methods of insertion of the NIF-1FL coding region into mammalian and yeast expression vectors described in Examples 11 and 12, respectively. PCR oligonucleotide primers are designed to generate an amplification product that contains the NIF-1FL coding region. As was described in connection for the methods for insertion of NIF-1FL into mammalian and yeast expression vectors (see Examples 11 and 12, respectively), primers are engineered so that this fragment contains 5' and 3' restriction sites that are compatible with insertion into the selected expression vector. The expression construct is preferably engineered so that the recombinant NIF will be secreted into the cytoplasm and not the periplasmic space. This may be accomplished by omitting an *E. coli* secretion signal from the construct.

*E. coli* cells are transformed with the NIF-1FL expression vector construct using standard methods. (See, e.g., Molecular Cloning A Laboratory Manual, Sambrook, J. Fritsch, E. F. and Maniatis, T., Second Edition, Cold Spring Harbor Laboratory Press, 1989, 1.74–1.84). Cells are grown in appropriate media (e.g. Luria Broth; see Molecular Cloning. A Laboratory Manual, Sambrook, J. Fritsch, E. F. and Maniatis, T., Second Edition, Cold Spring Harbor Laboratory Press, 1989, A.1) and harvested before they reach the stationary phase of growth.

The majority of the recombinant NIF should be present in the cytoplasm in the form of insoluble and functionally inactive aggregates. The solubilization and refolding of the recombinant protein present in these aggregates may be accomplished using known methods such as those reviewed in detail in Kohno et al., 1990 (Methods in Enzymology, 185:187–195). Refolded recombinant NIF may be separated from unfolded recombinant NIF and other reaction products using a number of standard chromatographic techniques, including C4 reverse phase HPLC (see, e.g., Example 2(E)). Refolded recombinant NIF is tested for functional activity using the neutrophil function assays described in Example 1.

This recombinant NIF is not glycosylated.

```
(1) GENERAL INFORMATION:

(iii) NUMBER OF SEQUENCES:          41

(2) INFORMATION FOR SEQ ID NO:    1:

(i) SEQUENCE CHARACTERISTICS:
          (A) LENGTH:                 16 AMINO ACIDS
          (B) TYPE:                   AMINO ACID
          (D) TOPOLOGY:               LINEAR (ii) MOLECULE TYPE:               PEPTIDE (ix) FEATURE:
          (D) OTHER INFORMATION:
               Xaa in location 7 is Arg, Lys, or Asn; Xaa in
               location 13 is Ile or Val; Xaa in location 14
               is Ser or Gly; and Xaa in location 16 is Thr
               or Ser.

(xi) SEQUENCE DESCRIPTION: SEQ ID NO: 1:

His Asn Gly Tyr Arg Ser Xaa Leu Ala Leu Gly His Xaa Xaa Ile Xaa
 1               5                  10                  15
```

(2) INFORMATION FOR SEQ ID NO: 2:

(i) SEQUENCE CHARACTERISTICS:
       (A) LENGTH:           22 AMINO ACIDS
       (B) TYPE:             AMINO ACID
       (D) TOPOLOGY:         LINEAR (ii) MOLECULE TYPE:       PEPTIDE (ix) FEATURE:
       (D) OTHER INFORMATION:
           Xaa in location 1 is Phe or Tyr; Xaa in
           location 4 is Arg, Ser, or Thr; Xaa in location
           11 is Leu or Met; Xaa in location 12 is Glu or
           Lys; Xaa in location 16 is Glu or Asp; Xaa in
           location 17 is Ala or Ser; and Xaa in location
           19 is Lys or Arg.

(xi) SEQUENCE DESCRIPTION: SEQ ID NO: 2:

Xaa Ala Pro Xaa Ala Ser Lys Met Arg Tyr Xaa Xaa Tyr Asp Cys Xaa
1               5                   10                  15

Xaa Glu Xaa Ser Ala Tyr
        20

(2) INFORMATION FOR SEQ ID NO: 3:

(i) SEQUENCE CHARACTERISTICS:
       (A) LENGTH:           8 AMINO ACIDS
       (B) TYPE:             AMINO ACID
       (D) TOPOLOGY:         LINEAR (ii) MOLECULE TYPE:       PEPTIDE (xi) SEQUENCE DESCRIPTION: SEQ ID NO: 3:

Gly Glu Gly Val Leu Tyr Arg Ser
1               5

(2) INFORMATION FOR SEQ ID NO: 4:

(i) SEQUENCE CHARACTERISTICS:
       (A) LENGTH:           20 AMINO ACIDS
       (B) TYPE:             AMINO ACID
       (D) TOPOLOGY:         LINEAR (ii) MOLECULE TYPE:       PEPTIDE (ix) FEATURE:
       (D) OTHER INFORMATION:
           Xaa in location 12 is Thr or Ala, Xaa in
           location 15 is Phe or Val; and Xaa in location
           20 is Val or Ala.

(xi) SEQUENCE DESCRIPTION: SEQ ID NO: 4:

Ile Ser Asn Phe Ala Asn Leu Ala Trp Asp Arg Xaa Glu Lys Xaa Gly
1               5                   10                  15

Cys Ala Val Xaa
        20

(2) INFORMATION FOR SEQ ID NO: 5:

(i) SEQUENCE CHARACTERISTICS:
       (A) LENGTH:           8 AMINO ACIDS
       (B) TYPE:             AMINO ACID
       (D) TOPOLOGY:         LINEAR (ii) MOLECULE TYPE:       PEPTIDE (xi) SEQUENCE DESCRIPTION: SEQ ID NO: 5:

His Val Val Cys His Tyr Pro Lys
1               5

(2) INFORMATION FOR SEQ ID NO: 6:

(i) SEQUENCE CHARACTERISTICS:
        (A) LENGTH:           28
        (B) TYPE:             NUCLEIC ACID
        (C) STRANDEDNESS:    SINGLE
        (D) TOPOLOGY:        LINEAR (ii) MOLECULE TYPE:       NUCLEIC (ix) FEATURE:
        (D) OTHER INFORMATION:
            "N" represents G, A, T or C; "H" represents
            A or T or C; "Y" represents C or T.

(xi) SEQUENCE DESCRIPTION: SEQ ID NO: 6:

CTCGAATTCT NGCHATHYTN GGHTGGGC                                      28

(2) INFORMATION FOR SEQ ID NO: 7:

(i) SEQUENCE CHARACTERISTICS:
        (A) LENGTH:           29
        (B) TYPE:             NUCLEIC ACID
        (C) STRANDEDNESS:    SINGLE
        (D) TOPOLOGY:        LINEAR (ii) MOLECULE TYPE:       NUCLEIC (ix) FEATURE:
        (D) OTHER INFORMATION:
            "Y" represents C or T; "R" represents G or A.

(xi) SEQUENCE DESCRIPTION: SEQ ID NO: 7:

CTCGAATTCT TYTCTGGRAA RCGRTCRAA                                    29

(2) INFORMATION FOR SEQ ID NO: 8:

(i) SEQUENCE CHARACTERISTICS:
        (A) LENGTH:           33
        (B) TYPE:             NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 8:

ACCGAATTCA CCATGGAGGC CTATCTTGTG GTC                            33

(2) INFORMATION FOR SEQ ID NO: 9:

(i) SEQUENCE CHARACTERISTICS:
        (A) LENGTH:           28
        (B) TYPE:             NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 9:

CTGGAATTCT CGCTTACGTT GCCTTGGC                                      28

(2) INFORMATION FOR SEQ ID NO: 10:

(i) SEQUENCE CHARACTERISTICS:
        (A) LENGTH:           24
        (B) TYPE:             NUCLEIC ACID
        (C) STRANDEDNESS:    SINGLE
        (D) TOPOLOGY:        LINEAR

```
        (ii) MOLECULE TYPE:              NUCLEIC (xi) SEQUENCE DESCRIPTION: SEQ ID NO: 10:

AACGAACACA ACCTGAGGTG CCCG                                              24

(2) INFORMATION FOR SEQ ID NO:    11:

(i) SEQUENCE CHARACTERISTICS:
            (A) LENGTH:                  54
            (B) TYPE:                    NUCLEIC ACID
            (C) STRANDEDNESS:            SINGLE
            (D) TOPOLOGY:                LINEAR (ii) MOLECULE TYPE:              NUCLEIC (xi) SEQUENCE DESCRIPTION: SEQ ID NO: 11:

CCTCCTCCTA GATCTAAGCT TACTAGTTTA TAACTCTCGG AATCGATAAA ACTC             54

(2) INFORMATION FOR SEQ ID NO:    12:

(i) SEQUENCE CHARACTERISTICS:
            (A) LENGTH:                  45 AMINO ACIDS
            (B) TYPE:                    AMINO ACID
            (D) TOPOLOGY:                LINEAR (ii) MOLECULE TYPE:              PEPTIDE (ix) FEATURE:
            (D) OTHER INFORMATION:
                Xaa in locations 7, 10 and 18 refers to any of
                the 20 naturally occuring amino acids, since no
                specific amino acid was identified during Edman
                degradation of the peptide.

(xi) SEQUENCE DESCRIPTION: SEQ ID NO: 12:

Asn Glu His Asn Leu Arg Xaa Pro Gln Xaa Gly Thr Glu Met
 1               5                  10

Pro Gly Phe Xaa Asp Ser Ile Arg Leu Gln Phe Leu Ala Met
 15                  20                  25

His Asn Gly Tyr Arg Ser Lys Leu Ala Leu Gly His Ile Ser
         30                  35                  40

Ile Thr Glu
         45

(2) INFORMATION FOR SEQ ID NO:    13:

(i) SEQUENCE CHARACTERISTICS:
            (A) LENGTH:                  17 AMINO ACIDS
            (B) TYPE:                    AMINO ACID
            (D) TOPOLOGY:                LINEAR (ii) MOLECULE TYPE:              PEPTIDE (xi) SEQUENCE DESCRIPTION: SEQ ID NO: 13:

Ser Ala Phe Glu Leu Asp Ile Thr Asn Asn Gly Asn Gly Val Leu
 1               5                  10                  15

Met Arg (2) INFORMATION FOR SEQ ID NO:    14:

(i) SEQUENCE CHARACTERISTICS:
            (A) LENGTH:                  8 AMINO ACIDS
            (B) TYPE:                    AMINO ACID
            (D) TOPOLOGY:                LINEAR (ii) MOLECULE TYPE:              PEPTIDE
```

(xi) SEQUENCE DESCRIPTION: SEQ ID NO: 14:

Leu Ala Ile Leu Gly Trp Ala Arg
1               5

(2) INFORMATION FOR SEQ ID NO:    15:

(i) SEQUENCE CHARACTERISTICS:
        (A) LENGTH:              8 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 15:

Leu Phe Asp Arg Phe Pro Glu Lys
1               5

(2) INFORMATION FOR SEQ ID NO:    16:

(i) SEQUENCE CHARACTERISTICS:
        (A) LENGTH:              9 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 16:

Leu Glu Met Asp Cys Glu Ala Glu Lys
1               5

(2) INFORMATION FOR SEQ ID NO:    17:

(i) SEQUENCE CHARACTERISTICS:
        (A) LENGTH:              13 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 17:

Val Gly Thr Pro Cys Gly Asp Cys Ser Asn Tyr Thr Lys
1               5                   10

(2) INFORMATION FOR SEQ ID NO:    18:

(i) SEQUENCE CHARACTERISTICS:
        (A) LENGTH:              10 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 18:

Asp Glu Asn Ile Tyr Ile Phe Glu Asn Ser
1               5                   10

(2) INFORMATION FOR SEQ ID NO:    19:

(i) SEQUENCE CHARACTERISTICS:
        (A) LENGTH:              10 AMINO ACIDS
        (B) TYPE:                AMINO ACID
        (D) TOPOLOGY:            LINEAR (ii) MOLECULE TYPE:          PEPTIDE (ix) FEATURE:
        (D) OTHER INFORMATION:
            Xaa is Glu or His.

(xi) SEQUENCE DESCRIPTION: SEQ ID NO: 19:

Asp Glu Asn Ile Tyr Ile Phe Glu Asn Xaa
1               5                   10

(2) INFORMATION FOR SEQ ID NO:    20:

(i) SEQUENCE CHARACTERISTICS:
          (A) LENGTH:                11 AMINO ACIDS
          (B) TYPE:                  AMINO ACID
          (D) TOPOLOGY:              LINEAR (ii) MOLECULE TYPE:             PEPTIDE (ix) FEATURE:
          (D) OTHER INFORMATION:
               Xaa in location 3 is His or Gln; Xaa in
               location 10 is Arg or Gly; and Xaa in location
               11 is Ala or Tyr.

(xi) SEQUENCE DESCRIPTION: SEQ ID NO: 20:

Asp Ile Xaa Val Tyr Phe Ile Gly Gln Xaa Xaa
1               5                   10

(2) INFORMATION FOR SEQ ID NO:    21:

(i) SEQUENCE CHARACTERISTICS:
          (A) LENGTH:                14 AMINO ACIDS
          (B) TYPE:                  AMINO ACID
          (D) TOPOLOGY:              LINEAR (ii) MOLECULE TYPE:             PEPTIDE (xi) SEQUENCE DESCRIPTION: SEQ ID NO: 21:

Asp Phe Ala Pro Arg Ala Ser Lys Met Arg Tyr Leu Glu Tyr
1               5                   10

(2) INFORMATION FOR SEQ ID NO:    22:

(i) SEQUENCE CHARACTERISTICS:
          (A) LENGTH:                19 AMINO ACIDS
          (B) TYPE:                  AMINO ACID
          (D) TOPOLOGY:              LINEAR (ii) MOLECULE TYPE:             PEPTIDE (ix) FEATURE:
          (D) OTHER INFORMATION:
               Xaa in location 10 is Phe or Ala.

(xi) SEQUENCE DESCRIPTION: SEQ ID NO: 22:

Asp Tyr Ile Tyr Tyr Gln Leu Tyr Pro Xaa Pro Met Ala His
1               5                   10

Lys Met Arg Tyr Leu
15

(2) INFORMATION FOR SEQ ID NO:    23:

(i) SEQUENCE CHARACTERISTICS:
          (A) LENGTH:                15 AMINO ACIDS
          (B) TYPE:                  AMINO ACID
          (D) TOPOLOGY:              LINEAR (ii) MOLECULE TYPE:             PEPTIDE (ix) FEATURE:
          (D) OTHER INFORMATION:
               Xaa in locations 2, 9, and 14 refers to any of
               the 20  naturally occurring amino acids, since
               no specific amino acid was identified during
               Edman degradation of the peptide.

-continued (xi) SEQUENCE DESCRIPTION: SEQ ID NO: 23:

Asp Xaa Met Gly Leu Gln Phe Leu Xaa Met His Asn Gly Xaa Arg
1               5                   10                  15

(2) INFORMATION FOR SEQ ID NO:    24:

(i) SEQUENCE CHARACTERISTICS:
              (A) LENGTH:              16 AMINO ACIDS
              (B) TYPE:                AMINO ACID
              (D) TOPOLOGY:            LINEAR (ii) MOLECULE TYPE:             PEPTIDE (ix) FEATURE:
              (D) OTHER INFORMATION:
                   Xaa in location 10 is Met, Gln or Asn; and Xaa
                   in locations 11 and 15 refers to any of the 20
                   naturally occurring amino acids, since no
                   specific amino acid was identified during Edman
                   degradation of the peptide.

(xi) SEQUENCE DESCRIPTION: SEQ ID NO: 24:

Asp Ala Met Arg Leu Gln Phe Leu Ala Xaa Xaa Asn Gly Tyr Xaa Gly
1               5                   10                  15

(2) INFORMATION FOR SEQ ID NO:    25:

(i) SEQUENCE CHARACTERISTICS:
              (A) LENGTH:              11 AMINO ACIDS
              (B) TYPE:                AMINO ACID
              (D) TOPOLOGY:            LINEAR (ii) MOLECULE TYPE:             PEPTIDE (xi) SEQUENCE DESCRIPTION: SEQ ID NO: 25:

Asp Ile Ser Asn Phe Ala Asn Leu Ala Trp Asp
1               5                   10

(2) INFORMATION FOR SEQ ID NO:    26:

(i) SEQUENCE CHARACTERISTICS:
              (A) LENGTH:              30 AMINO ACIDS
              (B) TYPE:                AMINO ACID
              (D) TOPOLOGY:            LINEAR (ii) MOLECULE TYPE:             PEPTIDE (xi) SEQUENCE DESCRIPTION: SEQ ID NO: 26:

Asp Glu Asn Lys Tyr Ile Phe Glu Asn Ser Asn Asn Ile Ser Glu
1               5                   10                  15

Ala Ala Leu Lys Ala Met Ile Ser Gly Ala Lys Gly Ala Phe Asn
                20                  25                  30

(2) INFORMATION FOR SEQ ID NO:    27:

(i) SEQUENCE CHARACTERISTICS:
              (A) LENGTH:              7 AMINO ACIDS
              (B) TYPE:                AMINO ACID
              (D) TOPOLOGY:            LINEAR (ii) MOLECULE TYPE:             PEPTIDE (xi) SEQUENCE DESCRIPTION: SEQ ID NO: 27:

Ala Met Ile Ser Trp Ala Lys
1               5

(2) INFORMATION FOR SEQ ID NO:    28:

```
        (i) SEQUENCE CHARACTERISTICS:
            (A) LENGTH:              18 AMINO ACIDS
            (B) TYPE:                AMINO ACID
            (D) TOPOLOGY:            LINEAR (ii) MOLECULE TYPE:           PEPTIDE (ix) FEATURE:
            (D) OTHER INFORMATION:
                Xaa in location 1 refers to any of the 20
                naturally occurring amino acids, since no
                specific amino acid was identified during Edman
                degradation of the peptide.

(xi) SEQUENCE DESCRIPTION: SEQ ID NO: 28:

Xaa Ala Tyr Ala Val Val Asn Leu Pro Leu Gly Glu Ile Ala Pro
 1               5                  10                  15

Glu Ala Ile (2) INFORMATION FOR SEQ ID NO:   29:

(i) SEQUENCE CHARACTERISTICS:
            (A) LENGTH:              8 AMINO ACIDS
            (B) TYPE:                AMINO ACID
            (D) TOPOLOGY:            LINEAR (ii) MOLECULE TYPE:           PEPTIDE (ix) FEATURE:
            (D) OTHER INFORMATION:
                Xaa in locations 1 and 4 refers to any of the
                20 naturally occurring amino acids, since no
                specific amino acid was identified during Edman
                degradation of the peptide; and Xaa in location
                8 is Leu or Ile.

(xi) SEQUENCE DESCRIPTION: SEQ ID NO: 29:

Xaa Phe Tyr Xaa Phe Arg Glu Xaa
 1               5

(2) INFORMATION FOR SEQ ID NO:   30:

(i) SEQUENCE CHARACTERISTICS:
            (A) LENGTH:              31 AMINO ACIDS
            (B) TYPE:                AMINO ACID
            (D) TOPOLOGY:            LINEAR (ii) MOLECULE TYPE:           PEPTIDE (ix) FEATURE:
            (D) OTHER INFORMATION:
                Xaa in locations 17, 18, and 20 refers to any
                of the 20 naturally occurring amino acids,
                since no specific amino acid was identified
                during Edman degradation of the peptide.

(xi) SEQUENCE DESCRIPTION: SEQ ID NO: 30:

Gly Ala Phe Asn Leu Asn Leu Thr Glu Glu Gly Glu Gly Val
 1               5                  10

Leu Tyr Xaa Xaa Asn Xaa Asp Ile Ser Asn Phe Ala Asn Leu
15                  20                  25

Ala Trp Asp
30

(2) INFORMATION FOR SEQ ID NO:   31:

(i) SEQUENCE CHARACTERISTICS:
            (A) LENGTH:              20 AMINO ACIDS
            (B) TYPE:                AMINO ACID
```

-continued

```
       (D) TOPOLOGY:              LINEAR (ii) MOLECULE TYPE:            PEPTIDE (ix) FEATURE:
       (D) OTHER INFORMATION:
           Xaa in locations 1, 2, 3, 9, and 10 refers to
           any of the 20 naturally occurring amino acids,
           since no specific amino acid was identified
           during Edman degradation of the peptide.

(xi) SEQUENCE DESCRIPTION: SEQ ID NO: 31:

Xaa Xaa Xaa Gly Val Leu Tyr Arg Xaa Xaa Leu Thr Ile Ser Asn Phe
 1           5                  10                  15

Ala Asn Leu Ala
        20

(2) INFORMATION FOR SEQ ID NO:   32:

(i) SEQUENCE CHARACTERISTICS:
       (A) LENGTH:                825
       (B) TYPE:                  NUCLEIC ACID
       (C) STRANDEDNESS:          SINGLE
       (D) TOPOLOGY:              LINEAR (ii) MOLECULE TYPE:            NUCLEIC (ix) FEATURE:
       (A) NAME/KEY:  Coding Sequence
       (B) LOCATION:  1...822

(xi) SEQUENCE DESCRIPTION: SEQ ID NO: 32:

ATG GAG GCC TAT CTT GTG GTC TTA ATT GCC ATT GCT GGC ATA GCT CAT      48
Met Glu Ala Tyr Leu Val Val Leu Ile Ala Ile Ala Gly Ile Ala His
 1               5                  10                  15

TCC AAT GAA CAC AAC CTG AGG TGC CCG CAG AAT GGA ACA GAA ATG CCC      96
Ser Asn Glu His Asn Leu Arg Cys Pro Gln Asn Gly Thr Glu Met Pro
             20                  25                  30

GGT TTC AAC GAC TCG ATT AGG CTT CAA TTT TTA GCA ATG CAC AAT GGT     144
Gly Phe Asn Asp Ser Ile Arg Leu Gln Phe Leu Ala Met His Asn Gly
         35                  40                  45

TAC AGA TCA AAA CTT GCG CTA GGT CAC ATC AGC ATA ACT GAA GAA TCC     192
Tyr Arg Ser Lys Leu Ala Leu Gly His Ile Ser Ile Thr Glu Glu Ser
 50                  55                  60

GAA AGT GAC GAT GAT GAC GAT TTC GGT TTT TTA CCC GAT TTC GCT CCA     240
Glu Ser Asp Asp Asp Asp Asp Phe Gly Phe Leu Pro Asp Phe Ala Pro
 65                  70                  75                  80

AGG GCA TCG AAA ATG AGA TAT CTG GAA TAT GAC TGT GAA GCT GAA AAA     288
Arg Ala Ser Lys Met Arg Tyr Leu Glu Tyr Asp Cys Glu Ala Glu Lys
                 85                  90                  95

AGC GCC TAC ATG TCG GCT AGA AAT TGC TCG GAC AGT TCT TCT CCA CCA     336
Ser Ala Tyr Met Ser Ala Arg Asn Cys Ser Asp Ser Ser Ser Pro Pro
            100                 105                 110

GAG GGC TAC GAT GAA AAC AAG TAT ATT TTC GAA AAC TCA AAC AAT ATC     384
Glu Gly Tyr Asp Glu Asn Lys Tyr Ile Phe Glu Asn Ser Asn Asn Ile
        115                 120                 125

AGT GAA GCT GCT CTG AAG GCC ATG ATC TCG TGG GCA AAA GAG GCT TTC     432
Ser Glu Ala Ala Leu Lys Ala Met Ile Ser Trp Ala Lys Glu Ala Phe
130                 135                 140

AAC CTA AAT AAA ACA AAA GAA GGA GAA GGA GTT CTG TAC CGG TCG AAC     480
Asn Leu Asn Lys Thr Lys Glu Gly Glu Gly Val Leu Tyr Arg Ser Asn
145                 150                 155                 160

CAC GAC ATA TCA AAC TTC GCT AAT CTG GCT TGG GAC GCG CGT GAA AAG     528
His Asp Ile Ser Asn Phe Ala Asn Leu Ala Trp Asp Ala Arg Glu Lys
                165                 170                 175
```

```
TTT GGT TGC GCA GTT GTT AAC TGC CCT TTG GGA GAA ATC GAT GAT GAA      576
Phe Gly Cys Ala Val Val Asn Cys Pro Leu Gly Glu Ile Asp Asp Glu
            180                 185                 190

ACC AAC CAT GAT GGA GAA ACC TAT GCA ACA ACC ATC CAT GTA GTC TGC      624
Thr Asn His Asp Gly Glu Thr Tyr Ala Thr Thr Ile His Val Val Cys
    195                 200                 205

CAC TAC CCG AAA ATA AAC AAA ACT GAA GGA CAG CCG ATT TAC AAG GTA      672
His Tyr Pro Lys Ile Asn Lys Thr Glu Gly Gln Pro Ile Tyr Lys Val
210                 215                 220

GGG ACA CCA TGC GAC GAT TGC AGT GAA TAC ACA AAA AAA GCA GAC AAT      720
Gly Thr Pro Cys Asp Asp Cys Ser Glu Tyr Thr Lys Lys Ala Asp Asn
225                 230                 235                 240

ACC ACG TCT GCG GAT CCG GTG TGT ATT CCG GAT GAC GGA GTC TGC TTT      768
Thr Thr Ser Ala Asp Pro Val Cys Ile Pro Asp Asp Gly Val Cys Phe
            245                 250                 255

ATT GGC TCG AAA GCC GAT TAC GAT AGC AAG GAG TTT TAT CGA TTC CGA      816
Ile Gly Ser Lys Ala Asp Tyr Asp Ser Lys Glu Phe Tyr Arg Phe Arg
            260                 265                 270

GAG TTA TGA                                                           825
Glu Leu
```

(2) INFORMATION FOR SEQ ID NO: 33:

(i) SEQUENCE CHARACTERISTICS:
        (A) LENGTH:              274 AMINO ACIDS
        (B) TYPE:                AMINO ACID
        (D) TOPOLOGY:          LINEAR (ii) MOLECULE TYPE:         PEPTIDE (xi) SEQUENCE DESCRIPTION: SEQ ID NO: 33:

```
Met Glu Ala Tyr Leu Val Val Leu Ile Ala Ile Ala Gly Ile Ala
1               5                   10                  15

His Ser Asn Glu His Asn Leu Arg Cys Pro Gln Asn Gly Thr Glu
            20                  25                  30

Met Pro Gly Phe Asn Asp Ser Ile Arg Leu Gln Phe Leu Ala Met
            35                  40                  45

His Asn Gly Tyr Arg Ser Lys Leu Ala Leu Gly His Ile Ser Ile
            50                  55                  60

Thr Glu Glu Ser Glu Ser Asp Asp Asp Asp Phe Gly Phe Leu
            65                  70                  75

Pro Asp Phe Ala Pro Arg Ala Ser Lys Met Arg Tyr Leu Glu Tyr
            80                  85                  90

Asp Cys Glu Ala Glu Lys Ser Ala Tyr Met Ser Ala Arg Asn Cys
            95                  100                 105

Ser Asp Ser Ser Ser Pro Pro Glu Gly Tyr Asp Glu Asn Lys Tyr
            110                 115                 120

Ile Phe Glu Asn Ser Asn Asn Ile Ser Glu Ala Ala Leu Lys Ala
            125                 130                 135

Met Ile Ser Trp Ala Lys Glu Ala Phe Asn Leu Asn Lys Thr Lys
            140                 145                 150

Glu Gly Glu Gly Val Leu Tyr Arg Ser Asn His Asp Ile Ser Asn
            155                 160                 165

Phe Ala Asn Leu Ala Trp Asp Ala Arg Glu Lys Phe Gly Cys Ala
            170                 175                 180

Val Val Asn Cys Pro Leu Gly Glu Ile Asp Asp Glu Thr Asn His
            185                 190                 195
```

```
Asp Gly Glu Thr Tyr Ala Thr Thr Ile His Val Val Cys His Tyr
            200                 205                 210

Pro Lys Ile Asn Lys Thr Glu Gly Gln Pro Ile Tyr Lys Val Gly
            215                 220                 225

Thr Pro Cys Asp Asp Cys Ser Glu Tyr Thr Lys Lys Ala Asp Asn
            230                 235                 240

Thr Thr Ser Ala Asp Pro Val Cys Ile Pro Asp Asp Gly Val Cys
            245                 250                 255

Phe Ile Gly Ser Lys Ala Asp Tyr Asp Ser Lys Glu Phe Tyr Arg
            260                 265                 270

Phe Arg Glu Leu
```

(2) INFORMATION FOR SEQ ID NO: 34:

(i) SEQUENCE CHARACTERISTICS:
        (A) LENGTH:           232 AMINO ACIDS
        (B) TYPE:             AMINO ACID
        (D) TOPOLOGY:         LINEAR (ii) MOLECULE TYPE:         PEPTIDE (xi) SEQUENCE DESCRIPTION: SEQ ID NO: 34:

```
Met Glu Leu Leu Leu Arg Lys Phe Leu Leu Leu Trp Leu Ser Gly
 1               5                  10                  15

Thr Phe Lys Arg Gly Arg Arg Leu Val Val Leu Ala Ala Ile Ala
            20                  25                  30

Gly Ile Ala His Ala Asn Glu His Asp Pro Thr Cys Pro Gln Asn
            35                  40                  45

Gly Glu Lys Met Glu Lys Gly Phe Asp Asp Ala Ile Arg Leu Lys
            50                  55                  60

Phe Leu Ala Met His Asn Gly Tyr Arg Ser Arg Leu Ala Leu Gly
            65                  70                  75

His Val Ser Ile Thr Glu Glu Ser Glu Asp Tyr Asp Leu Tyr Asp
            80                  85                  90

Leu Leu Tyr Ala Pro Arg Ala Ser Lys Met Arg Tyr Leu Lys Tyr
            95                  100                 105

Asp Cys Glu Ala Glu Lys Ser Ala Tyr Glu Ser Ala Lys Lys Cys
            110                 115                 120

Gln Thr Thr Ala Ser Ser Trp Glu Lys Tyr Asp Glu Asn Leu Gln
            125                 130                 135

Val Ile Glu Asp Pro Lys Asp Ile Asn His Ala Ala Leu Lys Ala
            140                 145                 150

Ile Ile Ser Trp Ala Thr Glu Ala Phe Asn Leu Asn Lys Thr Gly
            155                 160                 165

Glu Gly Val Val Tyr Arg Ser Ile Leu Asp Ile Ser Asn Phe Ala
            170                 175                 180

Asn Leu Ala Trp Asp Thr Arg Glu Lys Val Gly Cys Ala Val Val
            185                 190                 195

Lys Cys Ser Pro Arg Thr Thr His Val Val Cys His Tyr Pro Lys
            200                 205                 210

Lys Ser Arg Arg Lys Glu Asn Pro Ile Tyr Thr Thr Gly Asn Arg
            215                 220                 225

Cys Gly Gly Cys Ser Asp Tyr
            230
```

(2) INFORMATION FOR SEQ ID NO: 35:

(i) SEQUENCE CHARACTERISTICS:
        (A) LENGTH:            208 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 35:

Glu Ser Asp Asp Asp Tyr Glu Tyr Gly Phe Leu Pro Asp Phe Ala Pro
1               5                   10                  15

Arg Ala Ser Lys Met Arg Tyr Leu Glu Tyr Asp Cys Glu Ala Glu Lys
            20                  25                  30

Ser Ala Tyr Val Ser Ala Ser Asn Cys Ser Asn Ile Ser Ser Pro Pro
        35                  40                  45

Glu Gly Tyr Asp Glu Asn Lys Tyr Ile Phe Glu Asn Ser Asn Asn Ile
    50                  55                  60

Ser Glu Ala Ala Leu Lys Ala Met Ile Ser Trp Ala Lys Glu Ala Phe
65                  70                  75                  80

Asn Leu Asn Lys Thr Gly Glu Gly Val Leu Tyr Arg Ser Asn Leu Thr
                85                  90                  95

Ile Ser Asn Phe Ala Asn Leu Ala Trp Asp Thr Arg Glu Lys Phe Gly
            100                 105                 110

Cys Ala Val Val Asn Cys Pro Leu Gly Lys Pro Asp Ala Ile Ile Thr
        115                 120                 125

Asp Asp Glu Glu Asn Tyr Ala Thr Ala Ile His Val Val Cys His Tyr
    130                 135                 140

Pro Lys Ile Asn Lys Thr Glu Gly Gln Pro Ile Tyr Lys Val Gly Thr
145                 150                 155                 160

Pro Cys Asp Asp Cys Ser Glu Tyr Thr Lys Lys Ala Asp Asn Thr Thr
                165                 170                 175

Ser Ala Asp Pro Gln Cys His Pro Asp Ile Gly Val Cys Phe Ile Gly
            180                 185                 190

Ser Lys Gly Asp Tyr Asp Ser Lys Glu Phe Tyr Arg Phe Arg Glu Leu
        195                 200                 205

(2) INFORMATION FOR SEQ ID NO:    36:

(i) SEQUENCE CHARACTERISTICS:
        (A) LENGTH:            231 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 36:

Leu Leu Leu Ser Ser Ala Ala His Ser Asn Glu His Asn Pro Ile
1               5                   10                  15

Cys Ser Gln Asn Gly Thr Gly Met Phe Gly Phe Asn Asp Ser Met Arg
            20                  25                  30

Leu Lys Phe Leu Glu Met His Asn Gly Tyr Arg Ser Arg Leu Ala Leu
        35                  40                  45

Gly His Ile Ser Ile Thr Glu Glu Pro Glu Ser Tyr Asp Asp Asp
    50                  55                  60

Asp Tyr Gly Tyr Ser Glu Val Leu Tyr Ala Pro Ser Ala Ser Lys Met
65                  70                  75                  80

Arg Tyr Met Glu Tyr Asp Cys Glu Ala Glu Lys Ser Ala Tyr Lys Ser
                85                  90                  95

```
Ala Ser Ser Cys Ser Asp Ser Ser Ser Pro Glu Gly Tyr Asp Glu
            100                 105                 110

Asn Lys Tyr Ile Leu Glu Asn Ser Ser Asn Ile Ser Glu Ala Ala Arg
        115                 120                 125

Leu Ala Ile Leu Ser Trp Ala Lys Glu Ala Phe Asp Leu Asn Lys Thr
    130                 135                 140

Gly Glu Gly Val Leu Tyr Arg Ser Asn Leu Thr Ile Ser Asn Phe Ala
145                 150                 155                 160

Asn Leu Ala Trp Asp Thr Arg Glu Lys Phe Gly Cys Ala Val Ala Lys
                165                 170                 175

Cys Pro Leu Lys Asp Thr Ser Ala Thr Thr Ile His Val Val Cys His
            180                 185                 190

Tyr Pro Lys Ile Glu Gly Glu Glu Lys Glu Gly Lys Gln Ile Tyr Lys
            195                 200                 205

Val Gly Thr Pro Cys Gly Asp Cys Ser Glu Tyr Thr Lys Lys Ala Asp
    210                 215                 220

Asn Thr Thr Ser Thr Asp Pro
225                 230
```

(2) INFORMATION FOR SEQ ID NO:  37:

(i) SEQUENCE CHARACTERISTICS:
        (A) LENGTH:          224 AMINO ACIDS
        (B) TYPE:            AMINO ACID
        (D) TOPOLOGY:        LINEAR (ii) MOLECULE TYPE:        PEPTIDE (xi) SEQUENCE DESCRIPTION: SEQ ID NO: 37:

```
Leu Val Val Leu Ile Ala Ile Ala Gly Ile Ala His Ser Asn Glu His
1               5                   10                  15

Asn Leu Thr Cys Pro Gln Asn Gly Thr Glu Met Pro Gly Phe Asn Asp
            20                  25                  30

Ser Ile Arg Leu Gln Phe Leu Ala Met His Asn Gly Tyr Arg Ser Lys
        35                  40                  45

Leu Ala Leu Gly His Ile Ser Ile Thr Asp Glu Ser Glu Ser Glu Ser
    50                  55                  60

Asp Asp Glu Tyr Asp Tyr Trp Tyr Ala Pro Thr Ala Pro Thr Ala Ser
65                  70                  75                  80

Lys Met Arg Tyr Leu Glu Tyr Asp Cys Glu Ala Glu Lys Ser Ala Tyr
                85                  90                  95

Met Ser Ala Arg Asn Cys Ser Asp Ser Ser Pro Pro Glu Gly Asp
            100                 105                 110

Glu Asn Lys Tyr Ile Phe Glu Asn Ser Asn Ile Ser Glu Ala Ala
        115                 120                 125

Leu Lys Ala Met Ile Ser Trp Ala Lys Glu Ala Phe Asn Leu Asn Lys
    130                 135                 140

Thr Glu Glu Gly Glu Gly Val Leu Tyr Arg Ser Asn His Asp Ile Ser
145                 150                 155                 160

Asn Phe Ala Asn Leu Ala Trp Asp Thr Arg Glu Lys Phe Gly Cys Ala
                165                 170                 175

Val Val Asn Cys Pro Leu Gly Glu Ile Asp Gly Thr Thr Ile His Asp
            180                 185                 190

Gly Glu Thr Tyr Ala Thr Thr Ile His Val Val Cys His Tyr Pro Lys
            195                 200                 205

Met Asn Lys Thr Glu Gly Gln Pro Ile Tyr Lys Val Gly Lys Pro Cys
```

-continued

```
             210                 215                 220
```

(2) INFORMATION FOR SEQ ID NO:   38:

(i) SEQUENCE CHARACTERISTICS:
        (A) LENGTH:             146 AMINO ACIDS
        (B) TYPE:               AMINO ACID
        (D) TOPOLOGY:           LINEAR (ii) MOLECULE TYPE:         PEPTIDE (xi) SEQUENCE DESCRIPTION: SEQ ID NO: 38:

```
Met Lys Ser Tyr Leu Met Val Leu Ala Ala Val Ala Gly Ile Ala His
  1               5                  10                  15

Ala Asn Glu His Asp Leu Ile Cys Pro His Asn Glu Gly Glu Met Glu
                 20                  25                  30

Lys Gly Phe Asp Asp Ala Met Arg Leu Lys Phe Leu Ala Leu His Asn
             35                  40                  45

Gly Tyr Arg Ser Arg Leu Ala Leu Gly His Val Ser Ile Thr Glu Glu
         50                  55                  60

Ser Glu Asp Tyr Asp Leu Tyr Asp Leu Ser Tyr Ala Pro Thr Ala Ser
 65                  70                  75                  80

Lys Met Arg Tyr Leu Lys Tyr Asp Cys Glu Ala Glu Lys Ser Ala Tyr
                 85                  90                  95

Glu Ser Ala Lys Lys Cys Gln Thr Thr Ala Ser Ser Ser Thr Lys Tyr
                100                 105                 110

Asp Glu Asn Leu Gln Val Ile Glu Asp Pro Arg Asp Ile Asn His Ala
             115                 120                 125

Ala Leu Lys Ala Thr Ile Ser Trp Ala Thr Glu Ala Phe Asn Leu Asn
         130                 135                 140

Lys Thr
145
```

(2) INFORMATION FOR SEQ ID NO:   39:

(i) SEQUENCE CHARACTERISTICS:
        (A) LENGTH:             189 AMINO ACIDS
        (B) TYPE:               AMINO ACID
        (D) TOPOLOGY:           LINEAR (ii) MOLECULE TYPE:         PEPTIDE (xi) SEQUENCE DESCRIPTION: SEQ ID NO: 39:

```
Met Arg Leu Leu Arg Glu Ala Tyr Leu Val Val Leu Val Ala Ile Ala
  1               5                  10                  15

Gly Ile Ala His Ser Asn Glu His Asn Leu Thr Cys Pro Gln Asn Gly
                 20                  25                  30

Thr Glu Met Pro Asp Phe Ser Asp Ser Ile Arg Leu Gln Phe Leu Ala
             35                  40                  45

Met His Asn Gly Tyr Arg Ser Asn Leu Ala Leu Gly His Ile Gly Ile
         50                  55                  60

Ser Lys Glu Ser Ile Gly Asp Asp Tyr Asp Asp Tyr Tyr Tyr Phe
 65                  70                  75                  80

Tyr Ser Ser Tyr Ala Pro Met Ala Ser Lys Met Arg Tyr Leu Glu Tyr
                 85                  90                  95

Asp Cys Asp Ser Glu Arg Ser Ala Tyr Met Ser Ala Ser Asn Cys Ser
                100                 105                 110

Asp Ser Ser Pro Pro Glu Gly Tyr Asp Glu Asn Lys Tyr Ile Leu
             115                 120                 125
```

```
Glu Asn Ser Ser Asn Ile Asn Glu Ala Ala Arg Leu Ala Ile Ile Ser
    130                 135                 140

Trp Gly Lys Glu Ala Phe Asn Leu Asn Glu Thr Gly Glu Gly Val Leu
145                 150                 155                 160

Tyr Arg Ser Asn Leu Thr Ile Ser Asn Phe Ala Asn Leu Ala Trp Asp
                165                 170                 175

Thr Arg Glu Lys Phe Gly Cys Ala Val Val Lys Cys Pro
            180                 185
```

(2) INFORMATION FOR SEQ ID NO: 40:

(i) SEQUENCE CHARACTERISTICS:
        (A) LENGTH:          774 BASE PAIRS
        (B) TYPE:            NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 40:

```
AACGAACACA ACCTGAGGTG CCCGCAGAAT GGAACAGAAA TGCCCGGTTT CAACGACTCG      60

ATTAGGCTTC AATTTTTAGC AATGCACAAT GGTTACAGAT CAAAACTTGC GCTAGGTCAC     120

ATCAGCATAA CTGAAGAATC CGAAAGTGAC GATGATGACG ATTTCGGTTT TTTACCCGAT     180

TTCGCTCCAA GGGCATCGAA AATGAGATAT CTGGAATATG ACTGTGAAGC TGAAAAAAGC     240

GCCTACATGT CGGCTAGAAA TTGCTCGGAC AGTTCTTCTC CACCAGAGGG CTACGATGAA     300

AACAAGTATA TTTTCGAAAA CTCAAACAAT ATCAGTGAAG CTGCTCTGAA GGCCATGATC     360

TCGTGGGCAA AGAGGCTTT CAACCTAAAT AAAACAAAAG AAGGAGAAGG AGTTCTGTAC      420

CGGTCGAACC ACGACATATC AAACTTCGCT AATCTGGCTT GGGACGCGCG TGAAAAGTTT     480

GGTTGCGCAG TTGTTAACTG CCCTTTGGGA GAAATCGATG ATGAAACCAA CCATGATGGA     540

GAAACCTATG CAACAACCAT CCATGTAGTC TGCCACTACC CGAAAATAAA CAAAACTGAA     600

GGACAGCCGA TTTACAAGGT AGGGACACCA TGCGACGATT GCAGTGAATA CACAAAAAAA     660

GCAGACAATA CCACGTCTGC GGATCCGGTG TGTATTCCGG ATGACGGAGT CTGCTTTATT     720

GGCTCGAAAG CCGATTACGA TAGCAAGGAG TTTTATCGAT TCCGAGAGTT ATAA          774
```

(2) INFORMATION FOR SEQ ID NO: 41:

(i) SEQUENCE CHARACTERISTICS:
        (A) LENGTH:          257 AMINO ACIDS
        (B) TYPE:            AMINO ACID
        (D) TOPOLOGY:        LINEAR (ii) MOLECULE TYPE:       PEPTIDE (xi) SEQUENCE DESCRIPTION: SEQ ID NO: 41:

```
Asn Glu His Asn Leu Arg Cys Pro Gln Asn Gly Thr Glu Met Pro Gly
  1                 5                  10                  15

Phe Asn Asp Ser Ile Arg Leu Gln Phe Leu Ala Met His Asn Gly Tyr
                 20                  25                  30

Arg Ser Lys Leu Ala Leu Gly His Ile Ser Ile Thr Glu Glu Ser Glu
             35                  40                  45

Ser Asp Asp Asp Asp Asp Phe Gly Phe Leu Pro Asp Phe Ala Pro Arg
         50                  55                  60

Ala Ser Lys Met Arg Tyr Leu Glu Tyr Asp Cys Glu Ala Glu Lys Ser
 65                  70                  75                  80
```

-continued

| | | | | | | | | | | | |
|---|---|---|---|---|---|---|---|---|---|---|---|
| Ala | Tyr | Met | Ser | Ala | Arg | Asn | Cys | Ser | Asp | Ser | Ser | Pro | Pro | Glu |
| | | | | 85 | | | | | 90 | | | | 95 | |
| Gly | Tyr | Asp | Glu | Asn | Lys | Tyr | Ile | Phe | Glu | Asn | Ser | Asn | Asn | Ile | Ser |
| | | | | 100 | | | | | 105 | | | | 110 | | |
| Glu | Ala | Ala | Leu | Lys | Ala | Met | Ile | Ser | Trp | Ala | Lys | Glu | Ala | Phe | Asn |
| | | | 115 | | | | | 120 | | | | | 125 | | |
| Leu | Asn | Lys | Thr | Lys | Glu | Gly | Glu | Gly | Val | Leu | Tyr | Arg | Ser | Asn | His |
| | | | 130 | | | | | 135 | | | | 140 | | | |
| Asp | Ile | Ser | Asn | Phe | Ala | Asn | Leu | Ala | Trp | Asp | Ala | Arg | Glu | Lys | Phe |
| 145 | | | | | 150 | | | | | 155 | | | | | 160 |
| Gly | Cys | Ala | Val | Val | Asn | Cys | Pro | Leu | Gly | Glu | Ile | Asp | Asp | Glu | Thr |
| | | | | 165 | | | | | 170 | | | | | 175 | |
| Asn | His | Asp | Gly | Glu | Thr | Tyr | Ala | Thr | Thr | Ile | His | Val | Val | Cys | His |
| | | | | 180 | | | | | 185 | | | | 190 | | |
| Tyr | Pro | Lys | Ile | Asn | Lys | Thr | Glu | Gly | Gln | Pro | Ile | Tyr | Lys | Val | Gly |
| | | | | 195 | | | | | 200 | | | | 205 | | |
| Thr | Pro | Cys | Asp | Asp | Cys | Ser | Glu | Tyr | Thr | Lys | Lys | Ala | Asp | Asn | Thr |
| | | | 210 | | | | | 215 | | | | 220 | | | |
| Thr | Ser | Ala | Asp | Pro | Val | Cys | Ile | Pro | Asp | Asp | Gly | Val | Cys | Phe | Ile |
| 225 | | | | | 230 | | | | | 235 | | | | | 240 |
| Gly | Ser | Lys | Ala | Asp | Tyr | Asp | Ser | Lys | Glu | Phe | Tyr | Arg | Phe | Arg | Glu |
| | | | | 245 | | | | | 250 | | | | | 255 | |
| Leu | | | | | | | | | | | | | | | |

We claim:

1. An isolated DNA molecule which encodes a Neutrophil Inhibitory Factor comprising the amino acid sequence of FIG. 8 (SEQ. ID. NO. 33).

2. A method for producing a biologically active Neutrophil Inhibitory Factor which comprises the steps of culturing host cells having an expression vector which comprises a nucleic acid molecule which encodes a Neutrophil Inhibitory Factor wherein said Neutrophil Inhibitory Factor has neutrophil inhibitory activity and comprises an amino acid sequence of SEQ. ID. NO. 33 under conditions wherein said Neutrophil Inhibitory Factor is expressed, and isolating said Neutrophil Inhibitory Factor.

3. An isolated nucleic acid molecule which encodes a Neutrophil Inhibitory Factor (NIF) wherein said NIF comprises an amino acid sequence of SEQ. ID. NO. 33 and wherein said NIF has neutrophil inhibitory activity.

4. An isolated nucleic acid molecule comprising a nucleotide sequence encoding a Neutrophil Inhibitory Factor which (i) occurs in or is isolated from an *Ancylostoma* species of parasitic worm or (ii) is obtainable from an Ancylostoma species of parasitic worm wherein said protein (a) has neutrophil inhibitory activity and (b) comprises the amino acid sequence of SEQ. ID. NO. 12.

5. An isolated nucleic acid molecule comprising a nucleotide sequence encoding a Neutrophil Inhibitory Factor wherein said Neutrophil Inhibitory Factor (i) occurs in an Ancylostoma species of parasitic worm or is obtainable from an Ancylostoma species of parasitic worm (ii) has neutrophil inhibitory activity, and (iii) comprises an amino acid sequence which occurs in an Ancylostoma species of parasitic worm selected from the group consisting of:

(1) His-Asn-Gly-Tyr-Arg-Ser-$X_1$-Leu-Ala-Leu-Gly-His-$X_2$-$X_3$-Ile-$X_4$ (SEQ. ID. NO. 1) , wherein $X_1$ is Arg, Lys, or Asn; $X_2$ is Ile or Val; $X_3$ is Ser or Gly; and $X_4$ is Thr or Ser;

(2) $X_5$-Ala-Pro-$X_6$-Ala-Ser-Lys-Mat-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{12}$ is Lys or Arg;

(3) Gly-Glu-Gly-Val-Leu-Tyr-Arg-Ser (SEQ. ID. NO. 3);

(4) Ile-Ser-Asn-Phe-Ala-Asn-Leu-Ala-Trp-Asp-$X_{12}$-Arg-Glu-Lys-$X_{13}$-Gly-Cys-Ala-Val-$X_{14}$ (SEQ. ID. NO. 4), wherein $X_{12}$ is Thr or Ala; $X_{13}$ is Phe or Val; and $X_{14}$ is Val or Ala; and (5) His-Val-Val-Cys-His-Tyr-Pro-Lys (SEQ. ID. No. 5).

6. The nucleic acid molecule of any of claim 3, 4 or 5 further comprising a promoter operably linked to the nucleic acid molecule.

7. An expression vector comprising the nucleic acid molecule of any of claim 3, 4 or 5 operably linked to control sequences recognized by a host cell transformed with the vector.

8. A host cell transformed with the vector of claim 7.

9. An isolated nucleic acid molecule comprising the nucleotide sequence of SEQ. ID. NO. 32.

10. An isolated nucleic acid molecule comprising the nucleotide sequence of SEQ. ID. NO. 40.

11. An isolated nucleic acid molecule comprising a nucleotide sequence encoding the amino acid sequence of SEQ. ID. NO. 33.

12. An isolated nucleic acid molecule comprising a nucleotide sequence encoding the amino acid sequence of SEQ. ID. NO. 41.

13. An expression vector comprising an isolated nucleic acid molecule having a nucleic acid sequence consisting essentially of the nucleic acid sequence of FIG. 8 (SEQ. ID. NO. 32).

14. An expression vector comprising an isolated nucleic acid molecule having a nucleic acid sequence consisting essentially of the nucleic acid sequence of SEQ. ID. NO. 40.

15. An expression vector comprising an isolated nucleic acid molecule having a nucleic acid sequence which encodes an amino acid sequence consisting essentially of the amino acid sequence of FIG. 8 (SEQ. ID. NO. 33).

16. An expression vector comprising an isolated nucleic acid molecule having a nucleic acid sequence which encodes an amino acid sequence consisting essentially of the amino acid sequence of SEQ. ID. NO. 41.

17. An expression vector comprising an isolated nucleic acid molecule having the nucleotide sequence of SEQ. ID. NO. 32.

18. An expression vector comprising an isolated nucleic acid molecule having the nucleotide sequence of SEQ. ID. NO. 40.

19. An expression vector comprising an isolated nucleic acid molecule having a nucleotide sequence which encodes the amino acid sequence of SEQ. ID. NO. 33.

20. An expression vector comprising an isolated nucleic acid molecule having a nucleotide sequence which encodes the amino acid sequence of SEQ. ID. NO. 41.

21. A host cell which contains the expression vector or any of claims 13 to 20.

22. The host cell of claim 21 which is a CHO cell.

23. An isolated nucleic acid molecule encoding an amino acid sequence for a Neutrophil Inhibitory Factor (NIF) wherein said NIF:

(a) occurs in an Ancylostoma species or is obtainable from a NIF which occurs in an Ancylostoma species;

(b) has neutrophil inhibitory activity; and (c) comprises an amino acid sequence selected from the group consisting of SEQ. ID. NOs. 1, 2, 3, 4, and 5.

24. An isolated nucleic acid molecule which encodes an amino acid sequence for a Neutrophil Inhibitory Factor (NIP) where said NIF:

(a) is obtainable from an Ancylostoma species;

(b) has neutrophil inhibitory activity; and (c) comprises an amino acid sequence selected from the group consisting of SEQ. ID. NOs. 1, 2, 3, 4, and 5 which occurs in an Ancylostoma species.

25. An isolated nucleic acid molecule which encodes an amino acid sequence for a Neutrophil Inhibitory Factor (NIF) where said NIF:

(a) is obtainable from an Ancylostoma species;

(b) has neutrophil inhibitory activity; and (c) comprises SEQ. ID. NOs. 1 to 5.

26. An isolated nucleic acid molecule which encodes an amino acid sequence for Neutrophil Inhibitory Factor (NIF) wherein said NIF:

(a) is isolated from an Ancylostoma species;

(b) bas neutrophil inhibitory activity; and (c) comprises an amino acid sequence selected from the group consisting of (i) His-Asn-Gly-Tyr-Arg-Ser-$X_1$-Leu-Ala-Leu-Gly-His-$X_2$-$X_3$-Ile-$X_4$ (SEQ. ID. NO. 1), wherein $X_1$ is Arg, Lys, or Asn; $X_2$ is Ile or Val; $X_3$ is Ser or Gly; and $X_4$ is Thr or Ser;

(ii) $X_5$-Ala-Pro-$X_6$-Ala-Ser-Lya-Mat-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lye or Arg;

(iii) Gly-Glu-Gly-Val-Leu-Tyr-Arg-Ser (SEQ. ID. NO. 3);

(iv) Ile-Ser-Asn-Phe-Ala-Asn-Leu-Ala-Trp-Asp-$X_{12}$-Arg-Glu-Lye-$X_{13}$-Gly-Cys-Ala-Val-$X_{14}$ (SEQ. ID. NO. 4), wherein $X_{12}$ is Thr or Ala; $X_{13}$ is Phe or Val; and $X_{14}$ is Val or Ala; and (v) His-Val-Val-Cys-His-Tyr-Pro-Lys (SEQ. ID. NO. 5).

27. An isolated nucleic acid molecule which encodes a Neutrophil Inhibitory Factor (NIF) wherein said NIF:

(a) occurs in or is obtainable from an Ancylostoma species;

(b) has neutrophil inhibitory activity;

(c) includes an amino acid sequence selected from the group consisting of (i) His-Asn-Gly-Tyr-Arg-Ser-$X_1$-Leu-Ala-Lau-Gly-His-$X_2$-$X_3$-Ile-$X_4$ (SEQ. ID. NO. 1), wherein $X_1$ is Arg, Lys, or Asn; $X_2$ is Ile or Val; $X_3$ is Ser or Gly; and $X_4$ is Thr or Ser;

(ii) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lys or Arg;

(iii) Gly-Glu-Gly-Val-Leu-Tyr-Arg-Ser (SEQ. ID. NO. 3);

(iv) Ile-Ser-Asn-Phe-Ala-Asn-Leu-Ala-Trp-Asp-$X_{12}$-Arg-Glu-Lys-$X_{13}$-Gly-Cys-Ala-val-$X_{14}$ (SEQ. ID. NO. 4), wherein $X_{12}$ is Thr or Ala; $X_{13}$ is Phe or Val; and $X_{14}$ is Val or Ala; and (v) His-Val-Val-Cya-His-Tyr-Pro-Lys (SEQ. ID. NO. 5; which sequence is obtainable from an Ancylostoma species.

28. An isolated nucleic acid molecule which encodes an amino acid sequence for Neutrophil Inhibitory Factor (NIF) wherein said NIF:

(a) has neutrophil inhibitory activity; and (b) comprises the following amino acid sequences (i) His-Asn-Gly-Ty-Arg-Ser-$X_1$-Leu-Ala-Leu-Cly-gis-$X_2$-$X_3$-Ile-$X_4$ (SEQ. ID. NO. 1), wherein $X_1$ is Arg, Lys, or Asn; $X_2$ is Ile or Val; $X_3$ is Ser or Gly; and $X_4$ is Thr or Ser;

(ii) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lys or Arg;

(iii) Gly-Glu-Gly-Val-Leu-Tyr-Arg-Ser (SEQ. ID. NO. 3);

(iv) Ile-Ser-Asn-Phe-Ala-Asn-Leu-Ala-Trp-Asp-$X_{12}$-Arg-Glu-Lys-$X_{13}$-Gly-Cys-Ala-Val-$X_{14}$, (SEQ ID. NO. 4), wherein $X_{12}$ is Thr or Ala; $X_{13}$ is Phe or Val; and $X_{14}$ is Val or Ala; and (v) His-Val-Val-Cys-His-Tyr-Pro-Lys (SEQ. ID. NO. 5);

which sequences are obtainable from an Ancylostoma species.

29. An isolated nucleic acid molecule which encodes an amino acid sequence for Neutrophil inhibitory Factor (NIF) wherein said NIF has neutrophil inhibitory activity; and wherein said nucleic acid molecule (a) is obtainable from an Ancylostoma species; and (b) encodes an amino acid sequence selected from the group consisting of (i) His-Asn-Gly-Tyr-Arg-Ser-$X_1$-Leu-Ala-Leu-Gly-His-$X_2$-$X_3$-Ile-$X_4$ (SEQ. ID. NO. 1), wherein $X_1$ is Arg, Lys, or Asn; $X_2$ is Ile or Val; $X_3$ is Ser or Gly, and $X_4$ is Thr or Ser;

(ii) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lys or or Arg;
(iii) Gly-Glu-Gly-val-Leu-Tyr-Arg-Ser (SEQ. ID. NO. 3);

(iv) Ile-Ser-Asn-Phe-Ala-Asn-Leu-Ala-Trp-Asp-$X_{12}$-Arg-Glu-Lys-$X_{13}$-Gly-Cys-Ala-Val-$X_{14}$ (SEQ. ID. NO. 4), wherein $X_{12}$ is Thr or Ala; $X_{13}$ is Phe or Val; and $X_{14}$ is Val or Ala; and (v) His-Val-Val-Cys-His-Tyr-Pro-Lys (SEQ. ID. NO. 5).

30. An isolated nucleic acid molecule which encodes an amino acid sequence for Neutrophil Inhibitory Factor (NIF) wherein said NIF has neutrophil inhibitory activity; and wherein said isolated nucleic acid (a) is isolated from an Ancylostema species; and (b) encodes an amino acid sequence selected from the group consisting of (i) His-Asn-Gly-Tyr-Arg-Ser-$X_1$-Leu-Ala-Leu-Gly-His-$X_2$-$X_3$-Ile-$X_4$ (SEQ. ID. NO. 1), wherein $X_1$ is Arg, Lys, or Asn; $X_2$ is Ile or Val; $X_3$ is Ser or Gly; and $X_4$ is Thr or Ser;

(ii) $X_5$-Ala-Pro-$X_6$-Ala-Ser-Lys-Met-Arg-Tyr-$X_7$-$X_8$-Tyr-Asp-Cys-$X_9$-$X_{10}$-Glu-$X_{11}$-Ser-Ala-Tyr (SEQ. ID. NO. 2), wherein $X_5$ is Phe or Tyr; $X_6$ is Arg, Ser, or Thr; $X_7$ is Leu or Met; $X_8$ is Glu or Lys; $X_9$ is Glu or Asp; $X_{10}$ is Ala or Ser; and $X_{11}$ is Lys or Arg;

(iii) Gly-Glu-Gly-Val-Leu-Tyr-Arg-Ser (SEQ. ID. No. 3);

(iv) Ile-Ser-Asn-Phe-Ala-Asn-Leu-Ala-Trp-Asp-$X_2$-Arg-Glu-Lye-$X_{13}$-Gly-Cys-Ala-Val-$X_{14}$ (SEQ. ID. NO. 4), wherein $X_{12}$ is Thr or Ala, $X_{13}$ is Phe or Val; and $X_{14}$ is Val or Ala; and (v) His-Val-Val-Cys-His-Tyr-Pro-Lys (SEQ. ID. NO. 5).

31. An expression vector comprising an isolated nucleic acid molecule of any of claims 23 to 30 operably linked to control sequences recognized by a host cell transformed with the vector.

32. A host cell transformed with an expression vector of claim 31.

33. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule is selected from the isolated nucleic acid molecules of claims 23 to 30.

34. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby the Neutrophil Inhibitory Pactor is expressed and said Neutrophil Inhibitory Factor is secreted and isolating the Neutrophil Inhibitory Factor secreted by the host cells, wherein said isolated nucleic acid molecule is selected from the isolated nucleic acid molecules of claims 23 to 30.

* * * * *